(12) United States Patent
Sachs et al.

(10) Patent No.: US 11,478,630 B2
(45) Date of Patent: Oct. 25, 2022

(54) DEVICES, SYSTEMS AND METHODS FOR THERAPEUTIC MUSCLE STIMULATION

(71) Applicants: Dan Sachs, Minneapolis, MN (US); Orhan Soykan, Lino Lakes, MN (US)

(72) Inventors: Dan Sachs, Minneapolis, MN (US); Orhan Soykan, Lino Lakes, MN (US)

( * ) Notice: Subject to any disclaimer, the term of this patent is extended or adjusted under 35 U.S.C. 154(b) by 0 days.

(21) Appl. No.: 16/954,999

(22) PCT Filed: Dec. 17, 2018

(86) PCT No.: PCT/US2018/066096
§ 371 (c)(1),
(2) Date: Jun. 17, 2020

(87) PCT Pub. No.: WO2019/126080
PCT Pub. Date: Jun. 27, 2019

(65) Prior Publication Data
US 2020/0391021 A1 Dec. 17, 2020

Related U.S. Application Data

(60) Provisional application No. 62/607,297, filed on Dec. 18, 2017.

(51) Int. Cl.
*A61N 1/04* (2006.01)
*A61N 1/36* (2006.01)

(52) U.S. Cl.
CPC ......... *A61N 1/0452* (2013.01); *A61N 1/0456* (2013.01); *A61N 1/0492* (2013.01);
(Continued)

(58) Field of Classification Search
CPC .. A61N 1/0452; A61N 1/0456; A61N 1/0492; A61N 1/36031; A61N 1/36016; A61N 1/36132; A61N 1/36139
See application file for complete search history.

(56) References Cited

U.S. PATENT DOCUMENTS 4,390,023 A    6/1983  Rise
7,257,448 B2   8/2007  Crowe et al.
(Continued)

FOREIGN PATENT DOCUMENTS

AU    2018392315 A1    7/2020
CA       3096853 A1    6/2019
(Continued)

OTHER PUBLICATIONS

Giggins, et al., Neuromuscular electrical stimulation exercise: a potential alternative to conventional exercise in the management of type 2 diabetes, *The British Journal of Diabetes*, 17(2):46-51 (2017).
(Continued)

*Primary Examiner* — Carl H Layno
*Assistant Examiner* — Anh-Khoa N Dinh
(74) *Attorney, Agent, or Firm* — Schwegman Lundberg & Woessner, P.A.

(57) ABSTRACT

Devices, systems and methods are described for providing muscle contraction stimulation therapy to treat myriad diseases, including heart failure, Type 2 diabetes, and peripheral vascular disease using a skin patch or implantable stimulator that includes a multiplicity of electrodes, a processor, a stimulation circuit, one or more sensors and programming for a patient interface unit, wherein the processor is programmed to control selection of a subset of the multiplicity of electrodes and of operation of the stimulation circuit responsive to an indication of an adverse physiologic response. The indication of patient discomfort may be determined by monitoring a physiologic parameter of the subject using the one or more sensors, by direct input from the subject via the patient interface unit programming, or a combination thereof.

35 Claims, 26 Drawing Sheets

(52) U.S. Cl.
CPC ..... *A61N 1/36031* (2017.08); *A61N 1/36132* (2013.01); *A61N 1/36139* (2013.01)

(56) References Cited

U.S. PATENT DOCUMENTS

| | | | |
|---|---|---|---|
| 8,145,318 B2 | 3/2012 | Van Herk et al. | |
| 8,209,030 B2 | 6/2012 | Minogue et al. | |
| 8,285,381 B2 | 10/2012 | Fahey | |
| 8,620,439 B2 | 12/2013 | Lee et al. | |
| 8,892,210 B2 | 11/2014 | Fahey | |
| 8,909,334 B2 | 12/2014 | Kolen et al. | |
| 9,126,039 B2 | 9/2015 | Fahey | |
| 9,302,104 B2 | 4/2016 | Fahey | |
| 2011/0190845 A1* | 8/2011 | Weisfeldt | A61B 5/4893 607/42 |
| 2012/0109233 A1* | 5/2012 | Lee | A61F 7/007 607/3 |
| 2013/0085420 A1 | 4/2013 | Feinstein | |
| 2016/0106994 A1* | 4/2016 | Crosby | A61N 1/36135 600/13 |

FOREIGN PATENT DOCUMENTS

| | | |
|---|---|---|
| CN | 111655325 A | 9/2020 |
| EP | 3727559 A1 | 10/2020 |
| JP | 2021506551 A | 2/2021 |
| WO | WO-2006/100609 A1 | 9/2006 |
| WO | WO-2017/132067 A2 | 8/2017 |
| WO | WO-2019/126080 A1 | 6/2019 |

OTHER PUBLICATIONS

International Search Report and Written Opinion dated May 23, 2019 in Int'l PCT Patent Appl. Serial No. PCT/US2018/066096.
Maffiuletti, et al., Effect of Gender and Obesity on Electrical Current Thresholds, *Muscle Nerve*, 8:1-6 (2011).
Nosaka, et al., Muscle Damage Induced by Electrical Stimulation, *Eur. J. Appl. Physiol.*, 111:2427-2437 (2011).
"European Application Serial No. 18830670.8, Response filed Feb. 1, 2021 to Communication pursuant to Rules 161 (1) and 162 EPC dated Jul. 30, 2020", 24 pgs.
"International Application Serial No. PCT/US2018/066096, International Preliminary Report on Patentability dated Jul. 2, 2020", 12 pgs.
"International Application Serial No. PCT/US2018/066096, Invitation to Pay Additional Fees dated Mar. 27, 2019", 11 pgs.

* cited by examiner

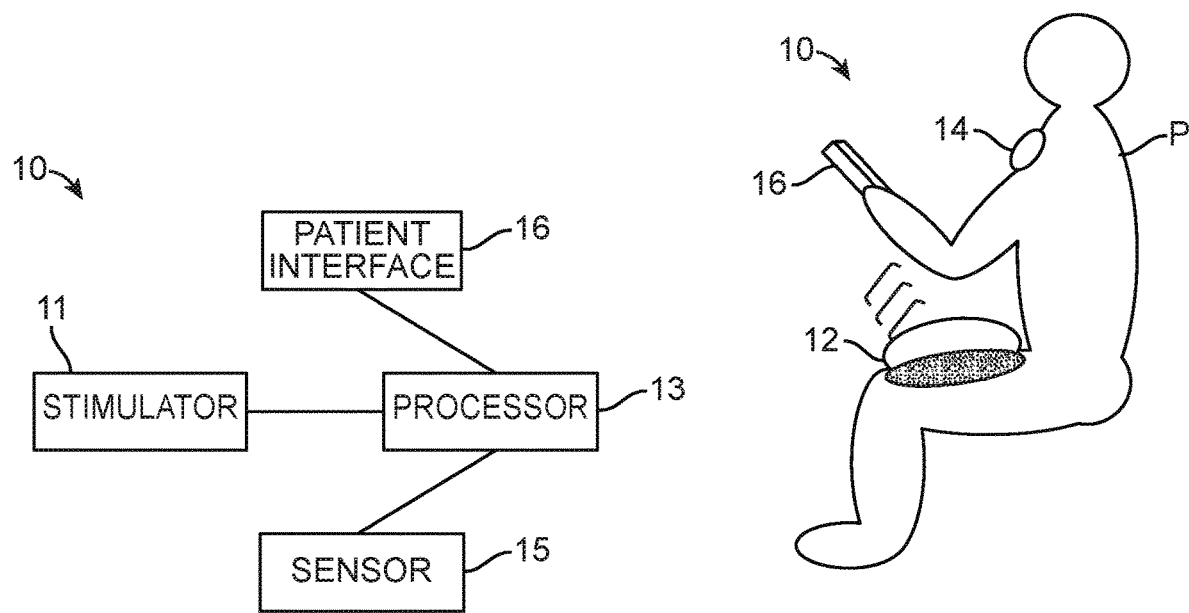
FIG. 1
FIG. 2
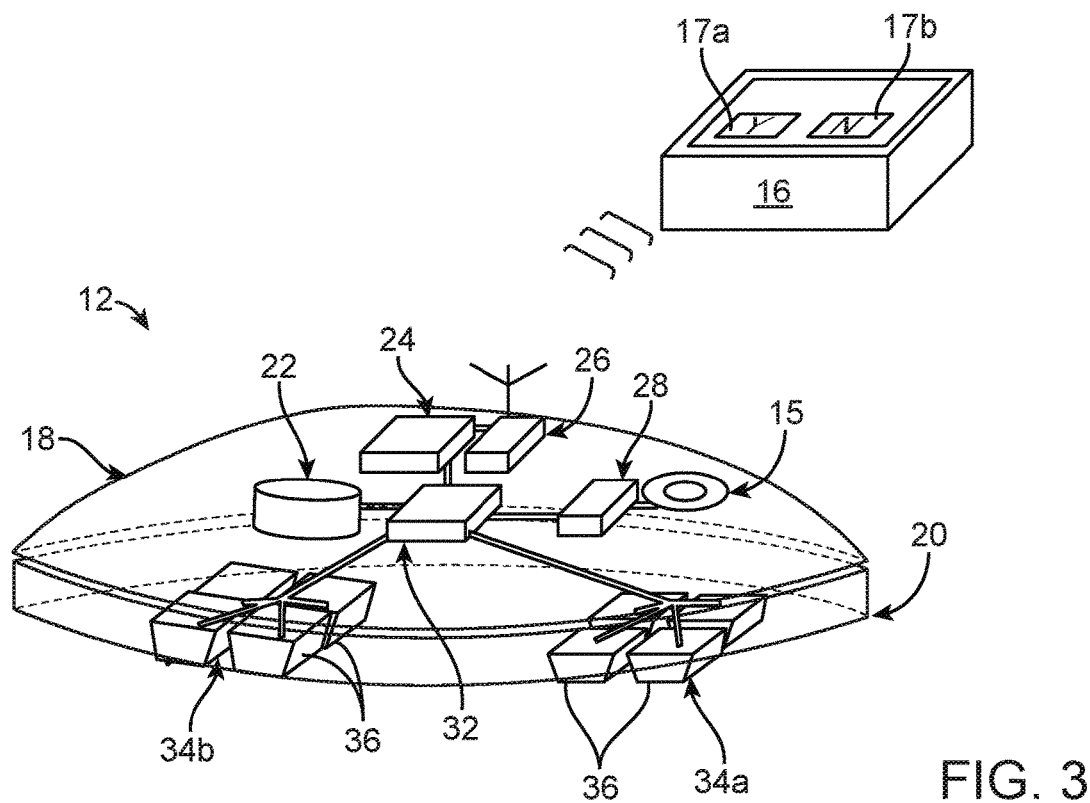
FIG. 3

Closeup of the Smart Phone screen while status info obtained via Blue Tooth is being displayed.

START, STOP, PROXIMAL PAIN and DISTAL PAIN are buttons for the user to push. Stim Amplitude, Accelerometer and Status are diagnostic data displays.

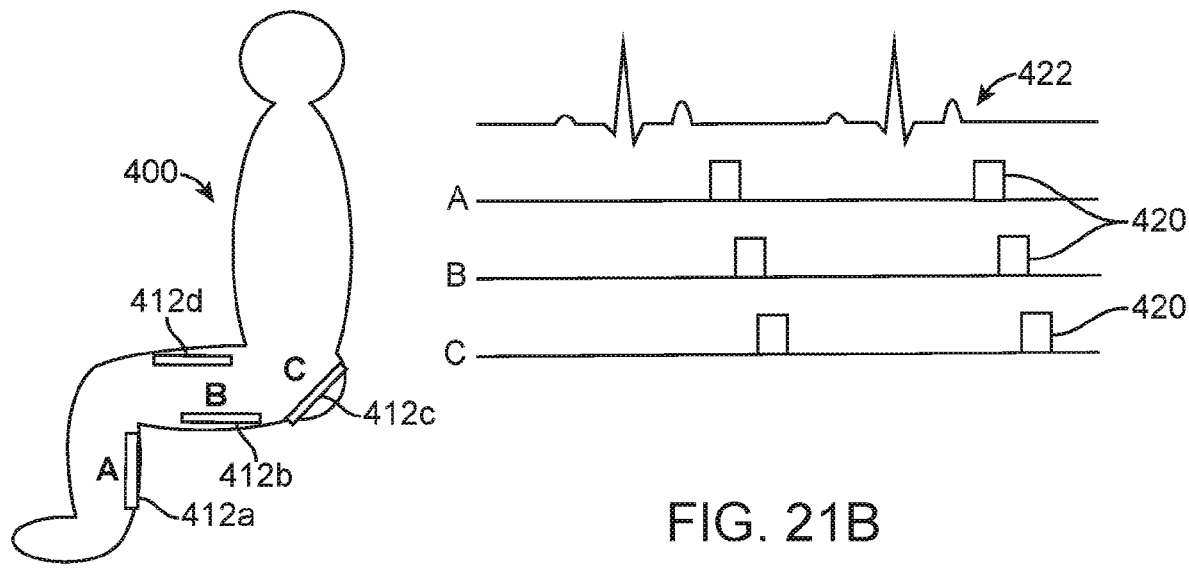
FIG. 21A
FIG. 21B
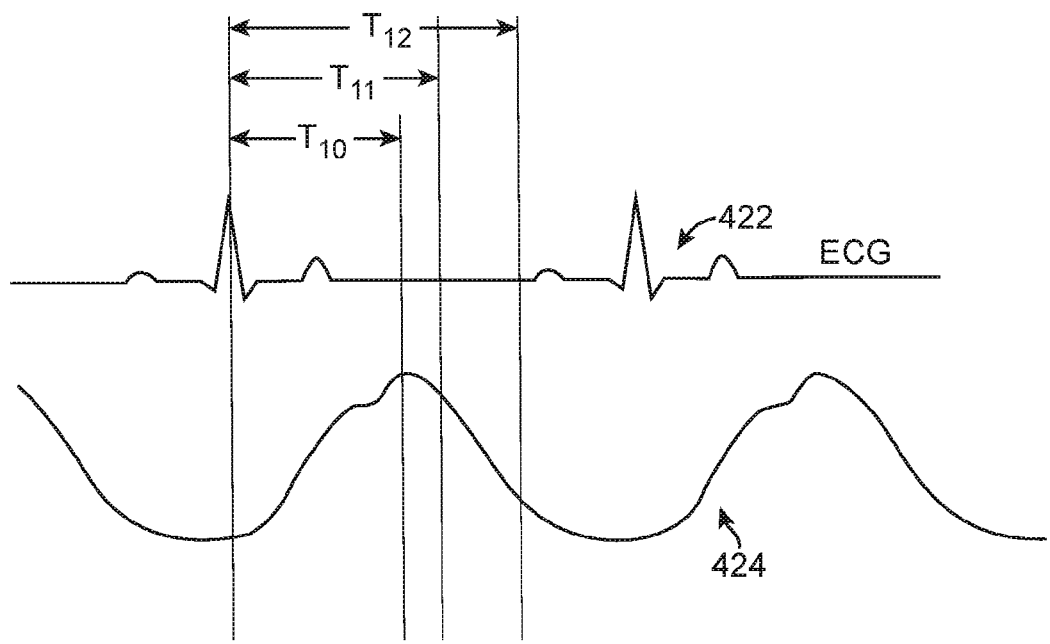
FIG. 22

DEVICES, SYSTEMS AND METHODS FOR THERAPEUTIC MUSCLE STIMULATION

CROSS-REFERENCE TO RELATED APPLICATIONS

This application is a national phase application under 35 U.S.C. 371 of PCT/US2018/066096, filed Dec. 17, 2018, which claims priority to U.S. Provisional Patent Application Ser. No. 62/607,297, filed Dec. 18, 2017, the entire contents of each of which are incorporated herein by reference.

FIELD OF THE INVENTION

The present application relates to medical devices and methods for stimulation muscles of the legs and other limbs to improve muscle tone, reduce atrophy, improve glucose uptake in Type 2 diabetics, and provide other health benefits. More specifically, this application relates to devices and methods for electrical modulation of nervous tissue to generate muscle contractions of skeletal muscles while reducing patient discomfort and improving patient safety.

BACKGROUND OF THE INVENTION

An overwhelming number of worldwide health problems stem from several common societal trends—an increasingly elderly population, an increasingly sedentary population, and an increasingly obese population. More and more people in modern society do not get even close to a sufficient amount of physical exercise, and this lack of exercise leads to myriad health problems, including obesity, non-alcoholic fatty liver disease, Type II diabetes, metabolic syndrome, heart conditions, heart failure, stroke, hypertension, joint conditions, arthritis, certain forms of cancer, and likely many other very significant health issues. Despite these epidemics, many people choose not to exercise, believe they cannot, or actually cannot adequately exercise, whether due to time constraints, poor motivation, or physical limitations.

Skeletal muscle is the largest organ in the human body. Of the many benefits that exercise provides, one critical set of benefits arises simply from the contraction of skeletal muscles in the body, especially the large muscles of the lower extremity, such as the gluteus, quadriceps, hamstrings and calf muscles. Contraction of skeletal muscle plays many roles in the skeletal system, including movement of bones, stabilization of joints, and remodeling of bone, cartilage, ligaments, and tendons. Chronic muscle contraction also may increase muscle strength, endurance, neural drive, motor control, and proprioception.

In addition, skeletal muscle plays an important role in the physiology of other organ systems. For example, contracting skeletal muscle improves cardiac fitness, impacts body temperature, pumps blood from the periphery to the trunk, helps circulate lymphatic fluid, decreases adipose tissue mass, regulates metabolism, and secretes of a variety of proteins, called myokines. Some of these myokines mainly affect muscle physiology, while others additionally affect other tissues and organs. Through secretion of myokines, skeletal muscle communicates with tissues throughout the body, such as the liver, fat, heart, brain and vasculature. Contracting lower limb muscles helps actively pump blood back to the heart, which then pumps that blood through the pulmonary artery to the lungs and through the aorta to the rest of the body. With the sedentary lifestyles that so many people in modern society live, by choice or due to physical limitation, muscle mass and muscle contraction are reduced.

Moreover, many chronic medical conditions are associated with a decline in muscle mass, muscle strength, and functional capacity, including type 1 diabetes, type 2 diabetes, obesity, hypogonadism in men, growth hormone deficiency, hyperthyroidism, neurodegenerative diseases, hypercortisolism, vitamin D deficiency, osteoporosis, rheumatoid arthritis, peripheral arterial disease, COPD, congestive heart failure, advanced kidney disease, cirrhosis, cancer, and HIV.

One method that has been studied for causing muscle contractions in subjects is neuromuscular electrical stimulation (NMES). NMES involves stimulating nerves proximal to or embedded within muscles for the purpose of causing muscle contraction. Researchers have found that using NMES devices to stimulate contraction of lower limb muscles can have significant positive effects on health. The patent literature describes a number of previously-known NMES systems that attempt to provide these benefits to patients. For example, U.S. Pat. No. 7,257,448 to Crowe et al. describes apparatus and methods for stimulating muscles, such as the hamstrings and quadriceps, to increase caloric consumption and improve fitness in which an individual electrodes in an array are selectively energized to induce muscle quivering, and operation of the apparatus is controlled by monitoring the cardiovascular response of the patient. That patent acknowledges that patient pain and discomfort can limit the utility of the described system, but does not address how to titrate the applied pulses to achieve sufficient muscle activation while avoiding patient discomfort.

U.S. Pat. No. 8,145,318 to Van Herk describes apparatus having an array of selectable electrodes coupled via a cross-switch to a stimulation signal generator and includes a sensor for detecting muscle activity, the output of which may be used by the patient to confirm electrode positioning and measure muscle tissue activity. U.S. Pat. No. 8,909,334 to Kolen et al. describes a similar system, in which a feedback system is used to assess the suitability of an electrical stimulation point to provide pain suppression via stimulation. Neither patent addresses reduction of patient discomfort caused by the stimulation or how to reduce such pain to improve patient compliance.

U.S. Pat. No. 8,209,030 to Minogue et al. describes a garment have a set of fixed-size replaceable selectively actuable electrodes, wherein the garment is configured to provide reproducible positioning when disposed on a patient's leg. U.S. Pat. No. 8,620,439 to Lee et al. describes an abdominal muscle stimulation system that includes an EMG sensor and other sensors, the outputs of which are used to compute a fatigue index for adjusting the stimulation regime.

U.S. Pat. No. 8,285,381 to Fahey describes a muscle stimulation system having an array of selectable electrodes coupled to stimulation generator, further including a plurality of sensors that provide feedback that assists in electrode selection, adjusting stimulation parameters and further may prevent the occurrence of undesirable conditions, such as temperature hotspots that may lead to burns of comatose or sedated patients. U.S. Pat. Nos. 8,892,210 and 9,302,104, both to Fahey, describe improvements to the system of the preceding patent, including methods and apparatus for optimizing stimulation parameters and/or stimulation location. U.S. Pat. No. 9,126,039, also to Fahey describes a muscle stimulation system including switching, cooling or analgesic systems, whereby the impedance of the patient's tissue is modified to adjust current density and thereby reduce patient discomfort.

While the benefits of NMES are recognized in the literature, previously-known systems have not overcome the recognized disadvantages of NMES systems in causing patient discomfort that adversely affects patient compliance and widespread use of such systems.

For example, an article entitled "Neuromuscular Electrical Stimulation Exercise: A Potential Alternative To Conventional Exercise In The Management Of Type 2 Diabetes," by Giggins et al., British Journal of Diabetes, (2017) 17(2):46-51, describes the results of a study in which NMES stimulation was used as a substitute for physical exercise for relatively healthy patients suffering from Type 2 diabetes, and produced significant improvements in body composition and fasting blood glucose levels. However, as indicated in that article, only male participants were recruited for the study because pilot testing demonstrated that NMES was not well-tolerated by overweight/obese female patients. Thus, while the foregoing article shows that NMES holds promise for treating Type 2 diabetes, the disadvantages of previously-known NMES systems have shown such systems to be unsuitable for large groups of the intended target population that could benefit from such treatments.

Similarly, an article entitled "Effect Of Gender And Obesity On Electrical Current Thresholds," by Maffiuletti et al., Muscle & Nerve, (2011) 8:1-6, describes the effect of gender and obesity on the effectiveness of neuromuscular stimulation, noting that women tend to experience pain and discomfort at lower thresholds than men, and that current thresholds required to activate muscles are higher in obese than non-obese subjects, and that obese subject tend to have reduced current tolerance. Those findings highlight the disadvantages of previously known muscle stimulation systems, and emphasize the need for improved NMES systems that address such drawbacks, improve patient compliance, and expand the target population for NMES systems.

Finally, an article entitled, "Muscle Damage Induced By Electrical Stimulation," by Nosaka et al., Eur J Appl Physiol (2011) 111:2427-2437, describes the potential for NMES to cause muscle injury, including rhapdomyolysis, and cautions that the NMES regimes suitable for frail or elderly patients must be carefully titrated and monitored to obtain a benefit, as opposed to inducing injury.

Accordingly, while the foregoing studies are very promising, previously-known muscle stimulation devices and techniques have a number of drawbacks. One significant drawback, as noted above, is discomfort caused by the electrical stimulation. To reduce this discomfort, clinicians will typically first locate the motor point on the patient—where motor nerves supply the muscle—in order to direct electrical stimulation toward that target and thereby use the lowest amplitude of stimulation required to cause muscle contraction. However, patient discomfort from sensory nerves in the skin layer typically requires a trade-off between placing electrodes near the motor point and avoiding the stimulation of painful sensory nerves. Thus, it can be very challenging to adequately stimulate a motor point to achieve a full muscle contraction without causing pain in the patient. And as demonstrated by the literature, this situation can be particularly challenging in overweight patients, obese patients, patients with swelling of the limbs from chronic venous insufficiency or fluid retention, anxious patients, or patients who suffer from hyper-sensitivity of the peripheral or central nervous system.

With existing approaches to transcutaneous electrical stimulation, a relatively high current intensity (amplitude) is often required to penetrate layers of skin and subcutaneous fat. Traditional NMES may cause discomfort or even significant pain at the high current intensities required to generate strong muscle contractions in many individuals. This is due to inadvertent activation of sensory fibers located between the skin surface and the muscle's nerve supply, as well as muscular pain receptors and fibers. The degree of current intensity one can use is limited by patient discomfort. For some patients, the sensation of electrical stimulation is unbearable, and such patients reject NMES as a treatment option altogether. Others may have a low tolerance for the optimal amplitude or treatment duration, and so they will receive a suboptimal treatment, which may limit the effectiveness of the therapy.

Another shortcoming of currently available technologies is that treatment sessions are typically limited to 30-60 minutes per session, three times a week for 4-8 weeks. In other words, NMES is not used for long periods of time. In addition to pain, NMES also may cause other unwanted side effects, such as skin irritation, electrical skin damage, muscle damage, kidney damage, and/or physiologic decompensation related to stimulation, especially in sick or elderly patients.

NMES can work well for a subset of patients. However, the physiology of every patient differs from the next, sometimes in extreme ways. NMES typically involves delivering energy through multiple tissue layers to reach the target nervous tissue, and patients differ widely in skin impedance, weight, height, body composition, body fat percentage, muscle mass, water volume and many other physical characteristics. For example, if the goal is to transcutaneously modulate nervous tissue beneath a muscle, energy must pass through the epidermis, dermis, subcutaneous fat, fascia and muscle. The distance between the skin surface and the target nervous tissue may vary from patient to patient, and also for a given patient, depending on the degree of tissue edema, presence of muscle contraction (which makes a muscle shorter and thicker), limb position, and the location of the electrodes on the skin surface. For example, subcutaneous fat thickness varies by individual. Patients who are overweight or obese will have a thicker layer of subcutaneous fat than patients who are underweight or normal weight. Also, patients with varying levels of tissue edema (e.g., interstitial fluid due to heart failure, "third spacing" of fluid, kidney failure, malnutrition, iatrogenic volume overloading with IV fluids, inactivity, etc.) will have differing distances from the skin surface to the target nervous tissue. There is also patient-to-patient variability in anatomical dimensions, location and branching of nerves. Moreover, nerve diameter, location, branching, myelination, and density vary from one person to the next. Sensory and motor thresholds are influenced by age and gender. Nerve function also varies from patient to patient, and from one part of a patient's body to another part, due to the state of a given patient's health. Chronic immunologic disorders, such as multiple sclerosis, diabetes, Guillain-Barre Syndrome and cancer, can lead to nerve dysfunction, as can acute nerve injuries from trauma, irritation, or compression syndromes. Due to these many variables, energy delivery treatment for each patient needs to be adjusted to that patient's specific physiology to most effectively cause tolerable yet effective muscle contraction. Currently available NMES devices and methods do not account for this variability.

It therefore would be advantageous to have improved devices, systems and methods for stimulating muscle contractions in patients. Ideally, such devices, systems and methods are configured so they can be safely used by patients in the home and other locations.

It would also be desirable to provide systems and methods for conducting muscle contraction treatments that can be safely performed for extended durations, so that patients may benefit from more long term, ongoing muscle contraction therapy.

It further would be desirable to provide systems and methods for inducing muscle contractions that are highly customizable, so that patients with a wide variety of body types, compositions, physical ailments or impairments and the like could receive the therapy safely and with minimal or no pain or other side effects. Ideally, such devices, systems, and methods could adapt to changing positions of the patient so that the motor point is stimulated in a tolerable fashion even when its position changes during the therapy.

SUMMARY OF THE INVENTION

The present application describes devices, systems and methods for stimulating muscle contractions in a patient to attain or preserve one or more health benefits. As used in this disclosure, the word "patient" means any human or animal subject. In accordance with the principles of the invention, muscle contractions are induced by stimulating nerve tissue, which in various embodiments may be nerve trunk, nerve branch, terminal nerve ending, motor point, Golgi receptors, Golgi tendon organ, muscle spindles or any other nerve tissue. Nerve tissue may be embedded in other tissue, such as connective tissue, fascia, ligaments, muscle, cartilage, periosteum, and bone. In general, the embodiments described herein include one or more stimulators, one or more sensors, one or more patient interface units, and at least one processor for processing data from, and providing signals to, the other components.

The stimulators, for example, may take the form of electrodes located on a patch or garment applied to the skin, one or more implantable electrodes, a percutaneous lead with electrode(s), a magnetic nerve stimulator, an ultrasound nerve stimulator or similar structure. Sensors may include muscle contraction sensors, muscle condition sensors, vital signs sensors, skin contact sensors, therapy end-point sensors, motion sensors and/or the like. A typical embodiment constructed in accordance with the principles of the present invention may include at least a muscle contraction sensor and at least one other sensor for sensing a patient parameter, e.g., muscle fatigue, pain, etc.

In some embodiments, the stimulator(s), sensor(s), processor(s) and/or patient interface unit(s) may be combined together in one device. For example, in one embodiment, multiple stimulators, a sensor and a processor may be included in a skin patch, and the patient interface unit may communicate wirelessly with the skin patch. Such an embodiment also may include one or more separate sensors that are configured to be attached to other areas on the body, such as an electrocardiogram (ECG) device or an electromyogram (EMG) device placed spaced apart from the skin patch.

These and other aspects of systems and devices constructed in accordance with the present invention, and methods of use thereof, are described in further detail below with reference to the attached drawing figures.

BRIEF DESCRIPTION OF THE DRAWINGS

FIG. 1 is a schematic diagram of the components of a muscle contraction stimulation system according to one embodiment;

FIG. 2 is a schematic view of a patient wearing a skin patch embodiment of a muscle contraction stimulation system constructed in accordance with the principles of the present invention;

FIG. 3 is a perspective view of the internal components of the skin patch embodiment and patient interface unit of the muscle contraction stimulation system of FIG. 2;

FIGS. 21A and 21B are, respectively, a side view of a patient having multiple muscle contraction stimulation skin patches applied to his lower extremity, and an ECG tracing and a chart illustrating timing of a muscle contraction therapy;

FIG. 22 is an ECG tracing and a ballistocardiogram curve, illustrating timing windows for a muscle contraction stimulation in accordance with an aspect of the present invention;

FIG. 41A is a cross sectional view of the anatomy of a human leg, while

DETAILED DESCRIPTION OF THE INVENTION

Figure 4A:
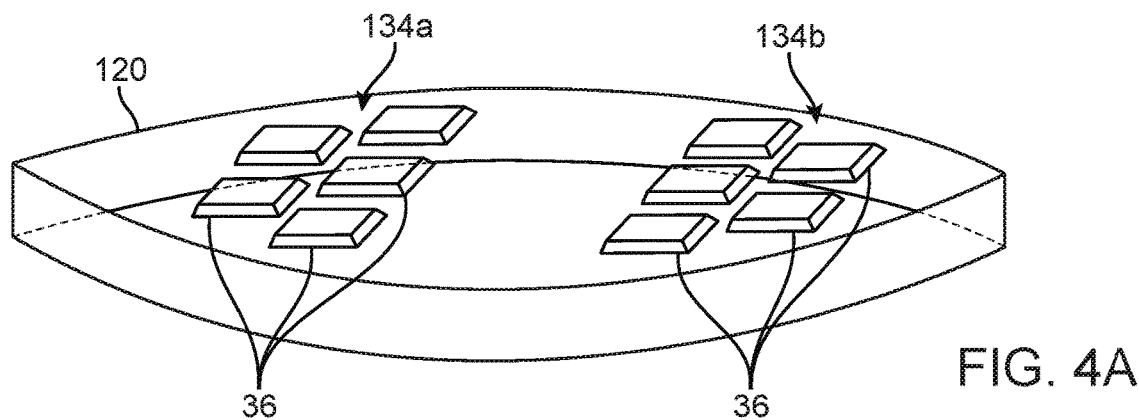
FIGS. 4A and 4B are bottom perspective views of two alternative embodiments of a disposable skin contacting electrode pad, either of which may be part of a skin patch portion of a muscle contraction stimulation system.

Unless defined otherwise, all technical and scientific terms used herein generally have the same meaning as commonly understood by one of ordinary skill in the relevant art.

The articles "a" and "an" are used herein to refer to one or to more than one (i.e., to at least one) of the grammatical object of the article. For example, "an element" means one element or more than one element.

The term "comprising" includes, but is not limited to, whatever follows the word "comprising." Use of the term indicates the listed elements are required or mandatory but that other elements are optional and may or may not be present.

The term "consisting of" includes and is limited to whatever follows the phrase "consisting of." The phrase indicates the limited elements are required or mandatory and that no other elements may be present.

The term "set" means one or more of the items from the same category.

"Microprocessor" is an electronic device that can be programmed to carry out certain tasks, including generating signals, collecting inputs, making decisions based on the inputs, and communicating with other devices in the system.

A "patient" is a human or animal subject. The patient can be an apparently healthy individual, an individual suffering from a disease, or an individual being treated for an acute condition or a chronic disease.

The term "electronics" refers to a set of electronic components including passive components such as resistors, capacitors, inductors, and crystals, active components such as amplifiers and transistors, as well as connectors, conductors and antennas.

"Electromyogram," or EMG, is an electrical signal that is generated by a skeletal muscle during a contraction that is either triggered by voluntary action or by electrical stimulation.

"Electrocardiogram," or ECG, is an electrical signal that is generated by the cardiac muscle during a contraction that is either triggered by voluntary action or by electrical stimulation.

"Electroencephalogram," or EEG, is an electrical signal that is generated by the brain during its normal function.

"Mechanomyogram," or MMG, is an electrical signal that is proportional to the physical motion that is generated by a muscle.

"Ballistocardiogram," is an electrical signal that is proportional to the physical motion of the tissue at various parts of the body resulting from the pulsatile flow of blood following a heartbeat.

"Electrodes" are conductive or semi-conductive elements that are used for delivery of electrical currents to tissues of humans and animals and/or for sensing of electrical signals generated by tissues of humans and animals, such as the electrocardiogram, electromyogram and electroencephalogram.

"Electrical noise" or "noise" is an undesirable signal that is superimposed on another signal of interest.

"Accelerometer" is a device that produces an electrical signal that is proportional to the physical acceleration of the device. Such devices may respond to physical activity in one, two or three-dimensions or rotations around any or all three axes.

"Temperature sensor" is a device that produces an electrical signal that is proportional to the physical temperature of device. It can be semi-conductive, thermocouple, resistance temperature detector ("RTDs") or thermistor.

"Tissue impedance" is a measure of the resistance that the tissue presents when an electrical signal is forced upon it. Impedance consists of a complex quantity including a real and an imaginary component corresponding to in phase and out phase components respectively.

As described above, neuromuscular electrical stimulation (MMES) has a number of disadvantages as a treatment modality because it can cause any number of adverse physiologic responses. MMES treatments may be painful, and it may be difficult to stimulate clinically significant muscle contraction without also inducing pain in the patient. Patients may have delicate skin that can be irritated, burned, or otherwise compromised. The patients are often elderly and/or have illnesses that may be exacerbated by NMES. Excessive NMES may cause muscle ischemia, edema, or breakdown (rhabdomyolysis). Thus, current systems and methods for providing NMES typically are not self-administered for prolonged periods of time by a patient or used at home or outside of a clinic or hospital by individuals with co-comorbidities, as any of a number of side effects may occur. Examples of side effects that may be caused by unsupervised NMES include physiologic decompensation (arrhythmia, hypotension, hypertension, tachycardia, bradycardia, tachypnea, hypoventilation, fever, hypothermia), skin injury, hypoglycemia, hyperkalemia, rhabdomyolysis, kidney damage, and unwanted muscle contractions while walking, driving, or performing other activities with which muscle contractions may interfere. Prolonged NMES will also eventually lead to muscle fatigue and deterioration. In summary, an adverse physiologic response may include one or more of the following: pain, muscle pain, skin pain, nerve pain, skin irritation, skin burning, skin injury, skin compromise, exacerbation of a chronic illness or illnesses, exacerbation of a co-morbidity or co-morbidities, muscle ischemia, muscle edema, muscle fatigue, muscle deterioration, rhabdomyolysis, physiologic decompensation, arrhythmia, hypotension, hypertension, tachycardia, bradycardia, tachypnea, hypoventilation, fever, hypothermia, hypoglycemia, hyperkalemia, hypocalcemia, serum electrolyte disturbance, kidney damage, cardiac ischemia, compromised cardiac output, shortness of breath, sleep disturbance, or unwanted muscle contractions while performing other activities with which muscle contractions may interfere.

The present application describes devices, systems and methods for stimulating muscle contractions in a patient, by stimulating one or more target nerve tissues that innervate one or more target muscles. The embodiments described herein generally include a stimulator, a sensor, a patient interface unit, and a processor. Each of these four components is described in greater detail below for multiple alternative embodiments, including devices that are applied externally to the skin and/or include implantable components. In general the devices, systems and methods described herein provide for muscle contraction therapy that may be applied for prolonged periods of time per therapy session (for example 1-8 hours), permit more frequent therapy sessions, longer courses of therapy, and more convenient therapy, for example administered and/or controlled at least in part by the patient in his/her home or other convenient location. This convenience and the longer, thus more effective, treatment regimens, are achieved by building in features to target stimulation, to minimize patient pain, provide more effective nerve tissue stimulation and thus muscle contraction, alter shape of electrical field to adjust to patient movement, and to monitor for side effects and adverse events and automatically adjust the electrical field shape, pause stimulation, or shut off the system as needed to promote safety.

For use in the LAMES systems of the present invention, expected stimulation parameters include the use of frequencies in a range of 2-10 Hz for non-tetanic pulse trains or 20-100 Hz for tetanic pulse trains, with amplitudes sufficient to induce muscle contractions and pulse durations of between 0.2 and 1 milliseconds. It is contemplated that preferred pulse shape should be either sinusoidal or square wave shaped, charge-balanced and include a duty cycle selected to achieve a desired pulse contraction goal without excessive fatigue or causing muscle damage.

Voluntary contraction of skeletal muscles are triggered when electrical impulses traveling through nerves reach the neuro-muscular junctions between the nerves and the target muscles. Involuntary contractions of the skeletal muscles may be induced by supplying electrical pulses using electronic circuits to the same neuro-muscular junctions. To generate such involuntary contractions, electrodes attached to pulse generators are used to deliver the pulses to target tissues.

Electrodes used for the stimulation of muscles may be implantable, that is, via leads placed percutaneously or subcutaneously so that electrodes of the lead are disposed within tissue, preferably near a targeted neuro-muscular junction. Alternatively, electrodes can be external, and be applied to the skin. In the latter case, the stimulation current enters the tissue from one or more electrodes, flows through the tissue, such that at least part of the current reaches the neuro-muscular junction, and exits the tissue via another electrode or electrodes to return back to the stimulator to complete the electrical circuit.

The delivery of direct electrical currents, i.e. DC, could damage tissue. Even pulsatile currents that are charge balanced are known to be harmful, as the resulting net charge left on the tissue causes ionic imbalances, harming tissue near the electrode as well as the target tissue itself. Hence, pulses that are charge balanced, i.e., with alternating polarity, or AC, are preferred in general for the stimulation of excitable tissues.

Stimulation pulses may have any morphology, however, ones with sine or rectangular shapes generally are preferred. The response of the tissue to an individual stimulation pulse tends to be binary, that is, sub-threshold stimulation usually does not result in a contraction of a muscle. The strength of an individual stimulation pulse may be increased by either enhancing the amplitude of the pulse, prolonging its duration, or both. Repetitive application of pulses forms a pattern that is known as a pulse train.

Pulse trains suitable for the stimulation of tissue may have a number of pulses, ranging from 1 to 25 or more. In general, each phase of the pulse, i.e. the positive and the negative pulses, lasts for 50 microseconds to 2 milliseconds, but most pulses used in LAMES systems commonly have duration of between 200 microseconds and 1 millisecond. To generate a biphasic stimulation pattern, the first pulse is immediately followed by another pulse having equal amplitude of opposite polarity. In some implementations, the amplitudes of the two phases, i.e., the positive and the negative pulses, are not equal. In that case, the duration of these pulses are adjusted to maintain the charge balance, such that pulses with lower amplitudes have a longer duration and vice versa.

Pulse pairs that are repeated at a rate of 2-10 Hz in a train may create a non-tetanic contraction, where individual contractions of the muscle resulting from the application of each pulse pair can be felt by the patient. At higher rates, the muscle generally does not have sufficient time to relax between the pulse pairs in the train, and the contractions begin to overlap. When the stimulation is applied at rates 20 Hz or above, individual contractions of most muscles fuse to form a tetanic contraction. As long as the train of stimulation pulses continues to be applied, the muscle will remain contracted, although after a few seconds fatigue will set in, and the stimulation intensity may need to be increased to main a contraction.

Electrodes used for the delivery of electrical stimulation to tissue may be of either polarizable or non-polarizable type. An electrode where no net current is released into the tissue is referred to as an ideally polarizable electrode. Such an electrode can be modeled as a pure capacitor. In general, the capacitance of an ideally polarizable electrode is in the range of 10-30 micro-Farad/cm2. Since a polarizable electrode acts as a capacitor, it builds a voltage at the tissue—electrode interface as current is injected into the tissue. Ideally non-polarizable electrodes, on the other hand, allow the electrical current to flow without impediment, and the injected electrical charges are accommodated by the ions in the tissue. For non-polarizable electrodes, no changes in voltage across the tissue-electrode interface occur upon the passage of a current, hence the electrode remains insensitive to the amount of current that is being delivered to the tissue. Due to this characteristic, non-polarizable electrodes generally are used in NMES systems for the delivery of electrical stimulation to the tissue and are preferred for use with the present invention.

As discussed below, electrode types suitable for use in the systems of the present invention generally should be made of a biocompatible material, metal or metal alloy, suitable for prolonged (1 to 8 hours) contact with skin without causing irritation, or suitable for implantation for those embodiments requiring implantable electrodes. For transcutaneous stimulation, the electrodes preferably are disposed on a flexible substrate that may be conformed to a patient's anatomy and include a biocompatible surrounding gel that facilitates electrical coupling to the patient's skin without excessive cross-talk between adjacent electrodes.

Transcutaneous Muscle Contraction Simulators, Systems and Methods

Referring now to FIG. 1, a first embodiment of muscle contraction stimulation system 10 constructed in accordance with the principles of the present invention includes stimulator 11, processor 13, sensor 15 and patient interface unit. Although each of these components—stimulator 11, processor 13, sensor 15 and patient interface unit 16—frequently are referred to in the singular in this application, a system of the present invention may include multiple such components. In some embodiments, stimulator 11, processor 13, sensor 15 and/or patient interface unit 16 may be combined together in one device. For example, in one preferred embodiment, multiple stimulators 11, processor 13 and sensor 15 may be included in skin patch 12. Such an embodiment also may include one or more separate sensor devices, for attaching to other areas on the body, such as an electrocardiogram (ECG) device, an electromyogram (EMG) or mechanomyogram (MMG) device placed spaced apart from the skin patch. Many different combinations and configurations are possible, several of which are discussed further below.

Patient interface unit 16 includes suitable programming or software loaded onto any device, such as a smart phone, a tablet device, a laptop computer, a desktop computer, which enables the patient to communicate with one or more other components of the system. Alternatively, patient interface unit 16 may be a dedicated device programmed for use only with muscle contraction stimulation system 10. In preferred embodiments, patient interface unit 16 may be used by the patient to provide an input indicating whether he/she feels pain during or after stimulation of nerve tissue. For example, a patient may be prompted to confirm discomfort after detection of markers of pain such as tachycardia, heart rate variability, blood pressure, or sympathetic nerve activity. Alternatively, a patient may indicate a sensation of discomfort, which is used by processor 13 to adjust the applied stimulation regime. Patient interface unit 16 may be configured for other uses as well, such as allowing a patient to input other information to system 10, to turn system on and off, to adjust the amount of stimulation current provided by stimulator 11, to view the patient's vital signs and/or other physiological information, and/or to view information about the therapy being delivered by system 10. Processor 13 receives signals from sensor 15 and patient interface unit 16, processes those signals, and provides signals to the stimulator 11 regarding when and how to stimulate nerve tissue to promote muscle contraction.

System 10 of the present invention provides a number of unique improvements over prior and currently available NMES devices. For example, system 10 is configured to receive input from patient interface unit 16 indicative of a patient's sensing of pain and use that information to customize nerve tissue stimulation for that particular patient's anatomy and physiology, using stimulators 11. System 10 also includes a combination of sensors 15 that can sense not only when a target muscle contracts (and an amount of contraction), but also a sensor that senses at least one other parameter of the patient, the output of which is utilized to enhance safety and/or efficacy of a muscle contraction treatment. For example, in various embodiments, sensors 15 may be used to sense vital signs of the patient, muscle fatigue or damage, physiological signs that indicate a clinical endpoint has been reached, and/or the like. A sensor, such as an accelerometer, may be used to detect if a patient is attempting to change position, such as moving to a sitting position from reclining position, or standing from seated position. Sensed data then may be used by system 10 to automatically pause, adjust or shut off a muscle contraction therapy. Thus, system 10 provides a customized muscle contraction stimulation therapy for each patient, with safety and efficacy features built in, so that muscle contraction therapies can be safely used outside the hospital or clinic or in a clinical setting with reduced direct supervision, for longer periods of time and over longer courses of treatment.

Another advantage of system 10 is that it may be used to treat multiple muscle groups of the same patient during a therapy session. Conventional NMES systems are known to target a single muscle group, such as the quadriceps. To stimulate four large muscles, such as two quadriceps and two hamstrings, using conventional NMES systems, a patient typically would have to be wired with at least eight wires and eight separate electrodes, which would make the initial wiring process and maintenance of such a system challenging, time-consuming and cumbersome (thus relegating such treatments to medical facilities only). By contrast, system 10 of the present invention is configured for use on one muscle group or on multiple muscle groups, for example in a sequential, distal-to-proximal stimulation pattern, to help pump blood from the legs to the trunk. In some embodiments, system 10 accomplishes this by providing all electronic components in a skin patch and having the skin patch communicate wirelessly with patient interface unit 16.

Two common problems associated with the use of transcutaneous electrical stimulation of skeletal muscles are inadvertent stimulation of sensory nerves close to the skin surface (causing pain) and difficulty in determining the correct placement of the electrodes to capture/stimulate the motor point. This is particularly relevant in patients who are not sedated by drugs. System 10 solves these problems by allowing a patient to input feedback into system 10 and automatically turn off certain stimulating electrodes in system 10 until a desired combination of pain reduction and clinically significant muscle contraction is achieved. Alternatively, other embodiments may provide one or more sensors that detect noxious stimuli, and responsive to such sensor outputs automatically turn off certain stimulating electrodes in system 10 until an acceptable combination of sensory stimulation and clinically significant muscle contraction is achieved.

System 10 also addresses the safety of long term unsupervised electrical stimulation for muscle contraction therapy. In preferred embodiments, system 10 uses information provided by sensors 15 to determine muscle fatigue, muscle damage and the like, such as rhabdomyolysis, and to alter or halt the stimulation regimen responsive to such sensor outputs. Sensors 15, such as but not limited to an accelerometer, an EMG sensor, a pressure sensor, an impedance sensor or a mechanomyography sensor (such as vibration detectors, microphones or ultrasound sensors) may be used for this purpose.

Accordingly, embodiments of muscle contraction stimulation system 10 constructed in accordance with the principles of the present invention may be used for longer periods of time than conventional systems—for example 1-8 hours at a time or more—while a patient is eating, reading, watching television, resting, sleeping and/or the like. Preferably, muscle contraction stimulation system 10 is configured to be self-administered by a patient or at least turned off and on by a patient, thereby facilitating home use, for prolonged courses of treatment, in order to more effectively attain desired health benefits compared to previously-known MMES systems. System 10 senses not only muscle contractions and parameters indicating unsafe conditions, but also may sense that one or more treatment objectives have been achieved for an individual treatment session. For example, if the system is used to treat Type 2 diabetes in a patient, the system may automatically stop stimulating muscle contractions once the system senses that the patient's glucose level has reached a target level. In some embodiments, the system may detect muscle fatigue and pause stimulation or change stimulation parameters to allow the muscle to recover. Also alternatively or additionally, some embodiments may change the site of stimulation to allow one set of muscle fibers to rest, while a different set of fibers is stimulated. In patients with compromised blood supply to the stimulated muscle, ischemia may develop in the tissue distal to the compromised blood supply, as oxygen demand may exceed supply. To address this, an embodiment of system 10 may include an ischemia sensor, which uses LED lights in the red and near infrared spectrum to continuously or intermittently measure oxygen saturation changes (SpO2). Based on the output of the sensor, the system may pause muscle contraction stimulation upon detection of muscle ischemia. Alternatively, the system may include a lactate sensor, such that when lactate levels begin to rise above baseline (i.e., when lactic acid is produced faster than the body can clear it), the system pauses stimulation of muscle contractions. In yet another embodiment, EMG may be used to determine muscle ischemia and accumulation of lactic acid, for the same purpose.

Referring now to FIG. 2, an exemplary embodiment of muscle contraction stimulation system 10 applied to patient P is described. System 10 includes stimulation/sensing patch 12 that is applied to the patient's skin, at least one sensor 14, which is separate and spaced apart from patch 12, and patient interface unit 16, which allows patient P to communicate with the other components of system 10. Patch 12 is shown applied over the quadriceps muscle of patient P (on the skin of the thigh) with sensor 14 shown applied over the patient's chest, for example, at a position suitable for placing the electrodes of ECG monitor. Preferably, patch 12 is positioned at a location on the patient's body so that it can be used to stimulate underlying nerve tissue. In some embodiments, this nerve tissue may be a motor point, where a nerve inserts into muscle tissue. In other embodiments, the target nerve tissue may be more proximal along the nerve, such as a nerve root, dorsal root ganglion (DRG), nerve trunk, nerve branch, or nerve branches. In still other embodiments, patch 12 may be applied over any muscle group of the body or over multiple muscle groups, to target one or more specific nerve tissues.

As explained above, it often may be advantageous to stimulate contractions of one or more muscles of the lower extremity, such as the gluteus, quadriceps, hamstrings and/or calf muscles. In such cases, multiple patches may be applied over those muscle groups or any of the muscles individually. For example, a patient may wear multiple skin patches 12 at the same time, with each patch 12 positioned over each of his gluteus, quadriceps, hamstrings and calf muscles on both limbs—i.e., for a total of eight skin patches 12. In other embodiments, it may be advantageous to stimulate contractions of these or other muscles by placing one or more patches 12 over a nerve trunk, for example in the groin region over the femoral nerve, over the buttocks to target the sciatic nerve, or over other muscle/nerve trunk targets. In yet other embodiments, larger patch devices may be provided, with each patch device being configured to overlay more than one muscle group and more than one target nerve tissue. Patches 12 may be provided individually or as a kit of multiple patches 12, according to various embodiments. Multiple patches may be connected via a wireless network, for example, as described below with respect to FIG. 20. Accordingly, while FIG. 2 shows only one skin patch 12 applied over one quadriceps muscle of a patient P, it should be understood that any number, configuration and placement of one or more skin devices 12 may be used.

Many of the exemplary embodiments described herein below involve systems that include one or more skin patches. However, in alternative embodiments, nerve tissue stimulation may be achieved using different types of stimulators, such as, but not limited to, one or more implantable electrodes, a percutaneous lead with electrode(s), a magnetic nerve stimulator, and ultrasound nerve stimulator and/or the like. In some embodiments, implantable devices may include one or more sensors and possibly one or more other features that are included in skin patch 12.

Referring now to FIG. 3, skin patch 12 having sensor 15 and patient interface unit 16 are described in greater detail. System 10, as depicted in FIG. 2, may include one or more additional sensors 14, suitable for detecting any of a number of physiological parameters of the patient P, which communicate with the processor of skin patch 12, patient interface unit 16, or both. As described in this disclosure, various combinations of sensor(s) 15 and separate sensor device(s) 14 may be provided in system 10. Thus, if in one embodiment a sensor is described as a possible sensor 14, in alternative embodiments that sensor may be included as sensor 15 of skin patch 12. The opposite may be true in other embodiments, and in general, any given embodiment may include any number, type and combination of sensor(s) 15 in skin patch 12 and separate sensors 14.

One preferred type of sensor 14 may be a muscle condition sensor, which allows system 10 to pause stimulation of nerve tissue when muscle condition deteriorates from a baseline state. Examples of muscle condition sensors may include an EMG device, (which may be used to detect muscle fatigue, ischemia or lactic acid), an infrared sensor (which may be used to detect lactic acid in the blood), and an ECG, an MMG or muscle impedance device to detect markers of rhabdomyolysis. Another example of separate sensor device 14 may include any type of vital sign sensor, which may be used to pause stimulation by system 10 if patient P becomes physiologically unstable. Such sensors include, but are not limited to, ECG devices, pulse oximeters, blood pressure monitors, transthoracic impedance monitors, inductance plethysmography devices, thermistors/thermometers, basic vital signs monitoring devices such as pulse counters and the like. Such devices may be used to monitor, for example, pulse rate, heart rhythm, arrhythmia, blood pressure, systemic blood pressure, diastolic blood pressure, mean arterial pressure, pulse pressure, venous pressure, cardiac ischemia, respiratory rate and/or body temperature. Yet another example of separate sensor device 14 may include a therapy achievement (or "therapeutic endpoint") sensor, which detects one or more physiological signs or parameters that may be used by system 10 to determine when a predefined amount of stimulation time or clinical efficacy endpoint has been reached. For example, such sensors may measure insulin sensitivity, blood glucose level, sympathetic nerve activity, vagal tone, sympathetic drive, heart rate variability, blood pressure, tissue edema or the like. As can be seen from these examples, separate sensor device 14 may include any suitable patient sensor or combination of sensors, configured for placement at any location(s) on the body.

Patient interface unit 16 may include a hardware component, a software component or both. In particular, a patient interface unit of the present invention need not include hardware, but may consist of a suitable application program that can be downloaded for use with a conventional smart phone, tablet, laptop, desktop or other programmable device that provides wireless connectivity. In alternative embodiments, patient interface unit 16 may be a proprietary device configured to be used only with system 10 or may include one or more other hardware components. Therefore, in general, patient interface unit 16 may be any hardware, software or combination thereof, which allows the patient P to input information into system 10 and in some embodiments to receive information from system 10. Patient interface unit 16 preferably communicates with skin patch 12 via a wireless connection. In alternative embodiments, however, patient interface unit 16 may connect to skin patch 12 via a wire or may plug into skin patch 12 via a docking station. In yet another alternative embodiment, patient interface unit 16 may simply be a button (or multiple buttons) on an outer surface of skin patch 12, such as a button that patient P may press whenever he/she feels pain in response to nerve stimulation. In most embodiments, patient interface unit 16 at least allows patient P to inform system 10 that he/she has experienced pain during or after a nerve stimulation or stimulated muscle contraction. System 10 may then use that information to customize the stimulation regimen to reduce or eliminate pain felt by the patient P.

In some embodiments, long duration electrodes may be used to deliver therapy. In this case, the electrodes are re-usable, hence there is rarely a reason to dispose of the skin patch. However, the patient interface unit may maintain a log of the therapy that is being delivered, which information may be retrieved from the memory of the patient interface unit directly or remotely. The therapy log retrieved from the patient interface unit may be used to determine an individual's compliance with the prescribed therapy regimen, and to make any necessary modifications to improve the outcomes. Therapy log information also may be used to enable a "fee per click" business model wherein a patient, family member, doctor, payer, or employer would periodically add funds to the patient's treatment account, against which there would be a deduction or debit with each treatment session.

In an embodiment with reusable electrodes, a variety of payment methods could be used to purchase treatment session credits, including credit cards, debit cards, checking accounts, gift cards, mobile phone billing, Paypal, online banking, or online retail payment methods such as Apple ID, Amazon ID, or Skype ID. To encourage compliance, patients also could be offered a discount for volume purchases of treatment sessions. Patients also could be charged a daily, weekly, monthly, quarterly, or annual fee instead of a fee per click basis. A recurring, time-based fee (similar to a monthly health club membership, or subscription to cable television) might encourage certain patients to use the device regularly rather than create a financial disincentive to regular use. Once funds in the patient's account for treatment sessions have been depleted, the interface unit would not be usable until additional funds are added to the account. Payment mechanisms also could include a combination of fee per click and subscription models, or a model that starts with one payment plan and then switches to another based on patient compliance, or the preference of the individual, family member, clinician, employer, or payer. Systems could also be leased to the patient, in a manner similar to durable medical equipment.

Referring again to FIG. 3, patch 12 includes outer substrate 18, tissue contact substrate 20, and multiple components coupled with each. In alternative embodiments, outer substrate 18 and tissue contact substrate 20 may be combined into a single monolithic substrate. In other words, although patch 12 is often described herein as a two-piece substrate embodiment, in alternative embodiments a patch may include a one-piece substrate. In some embodiments, outer substrate 18 is designed to be reusable, while tissue contact substrate 20 is designed to contact the patient's skin and be disposable (after one or multiple uses). In this case, the two substrates 18, 20 may be removably coupled to one another such that they may be separated easily by the patient for disposal of tissue contact substrate 20. Alternatively, both substrates 18, 20 may be reusable or both substrates 18, 20 may be disposable. In one preferred embodiment, outer substrate 18 houses power source 22, control unit 24, communications unit 26, signal processor 28, sensor 15 and electrical stimulation unit 32. Tissue contact substrate 20, in this embodiment, includes multiple electrode sets 34a and 34b, each of which illustratively includes four electrodes. All of these components may be attached to substrates 18 and 20 in any suitable way, such as by embedding the components between layers of substrates 18, 20 or attaching them to substrates 18, 20 with adhesive.

Tissue contact substrate 20 preferably is flexible and stretchable, so that it may be conformed to the patient's skin overlying the target muscle and move with the muscle as it contracts. Tissue contact substrate 20 may, for example, be made of one or more polymeric materials that are generally non-conductive, such as but not limited to rubbers, polyethylene, polypropylene, or any other insulating material, including cellulose. Outer substrate 18 also may be flexible and stretchable, but in some embodiments it may be somewhat stiffer, thicker and/or more durable than tissue contact substrate 20. Tissue contact substrate 20 also typically will include a biocompatible adhesive surface for adhering patch 12 to the patient's skin, which surface will be covered with a protective cover until ready for use. Such adhesive surfaces are well known. Tissue contact substrate 20 also may have two adhesive surfaces—one side for attaching to the skin and the opposite side for attaching to outer substrate 18. Ideally, all of skin patch 12 may be worn for prolonged periods of time, for example for a day or more. In some embodiments, skin patch 12 may be worn in the shower or bathtub. In other embodiments, only tissue contact substrate 20 may be worn in the shower or bathtub, and outer substrate 18 is removed for bathing.

Electrode sets 34a and 34b illustratively each include four transcutaneous electrodes 36. Although two electrode sets 34a, 34b, with four electrodes 36 each are shown in this embodiment, alternative embodiments may have more than two electrode sets and/or more or fewer than four electrodes for each set. Providing two electrode sets 34a, 34b per patch may have several advantages, in terms of simplicity and controllability of stimulation current, but any other suitable alternative embodiments are contemplated within the scope of the present invention. In general, the overall area of one electrode set 34a, 34b may be large enough to deliver a current that is sufficient to stimulate nerve tissue innervating one or more skeletal muscles that are being targeted for the therapeutic application. To minimize the current density being applied and, thus, discomfort to the patient, each electrode set 34a, 34b may have a total active surface area of at least about 20 cm squared and preferably at least about 30 cm squared.

Figure 4B:
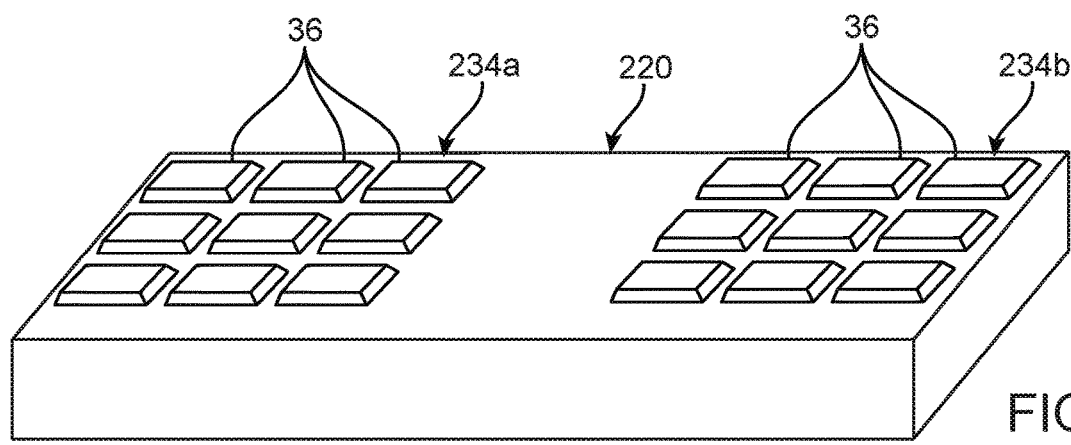
Figure 8:
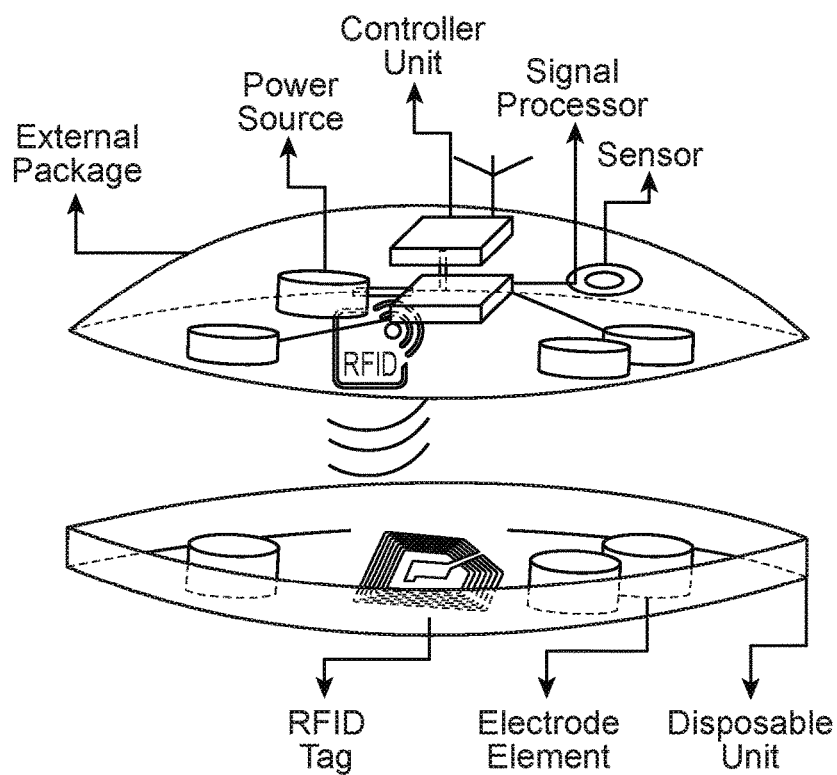
FIG. 8 is an illustration of an alternative embodiment of a muscle stimulation skin patch in which an RFID system is used for brand protection and safety.

Referring now to FIGS. 4A and 4B, two alternative embodiments of a tissue contact with alternative electrode sets are described. Substrates 120 and 220 of FIGS. 4A and 4B, respectively, include corresponding alternative configurations of electrode sets 134a, 134b, 234a, 234b. In some embodiments, some of the individual electrodes may need to be turned off during therapy to minimize pain sensation by redirecting the stimulation current within the tissue. In such cases, it may be preferable that the total surface area of an electrode set at the onset of stimulation be larger than the minimum surface area required for stimulation of the motor point or nerve supply to the target muscle(s). For example, in the embodiment of FIG. 4B, each electrode set 234a, 234b on a tissue contact substrate 220 may include nine electrodes 36, each having the dimensions of 4 cm squared, giving an initial total surface area of 36 cm squared for each electrode set 234a. Although electrode sets 34a and 34b of FIGS. 3 and 234a and 234b of FIG. 8B are arrayed in square patterns, in alternative embodiments the electrodes may be arranged in any other regular pattern or asymmetrical arrangement. For example, as shown in FIG. 4A, two electrode sets 134a, 134b of five electrodes each may be provided on tissue contact substrate 120. In other alternative embodiments, any orientation, number, shape and spacing of electrodes in a given electrode set may be used.

Electrodes 36 of FIGS. 3 and 4 may be made out of any suitable conductive materials, such as but not limited to carbon black. In some embodiments, electrodes 36 may be coated with a conductive gel, such as silver chloride gel. In alternative embodiments, where the electrodes are implantable, such electrodes may be constructed from metals, such as gold or silver, or metal alloys, such as platinum—iridium, or conductive polymers, such as those containing carbon black, or a combination of carbon and graphite. Each electrode 36 may range in size from about 2 mm squared to about 6 cm squared. Additionally, electrodes 36 may have any suitable shape, such as but not limited to a square (as illustrated), a circle, an ellipse, an oval, a curvilinear triangle, a quatrefoil, or any polygon, such as a triangle, a rectangle, a parallelogram, a trapezoid, a rhombus, a pentagon, a hexagon, and so on. In order to prevent unintentional stimulation via disconnected electrodes 36, a minimum separation between electrodes 36 in a given electrode set 34a, 34b on tissue contact substrate 20 may be approximately 0.5 mm. In order to provide desired stimulation of nerve tissue beneath the skin surface to promote muscle contraction, electrode sets 34a, 34b will typically be spaced at least about 3 cm from each other, when measured from the center of each set 34a, 34b.

Figure 5:
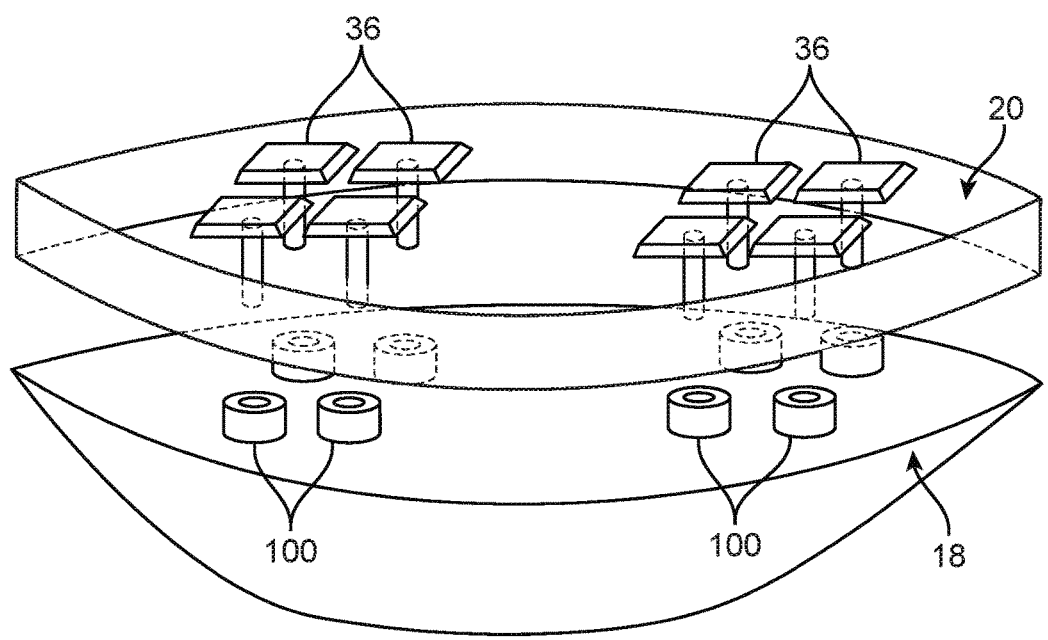
FIG. 5 is a perspective view from below of a skin contacting electrode pad and external housing according to one embodiment.

As shown in FIG. 5, each electrode 36 of tissue contact substrate 20 may be coupled to the electronics disposed on outer substrate 18 via separate electrode connectors 100. In various embodiments, electrode connectors 100 may be snap-fit connectors, mini-banana connectors, or other suitable connectors. Alternatively, skin patch 12 may include one monolithic substrate rather than separate tissue contact substrate 20 and outer substrate 18. In such embodiments, the entire skin patch 12 may be either reusable or disposable, and electrodes 36 may be permanently attached to the electronics disposed on the patch.

Figure 6:
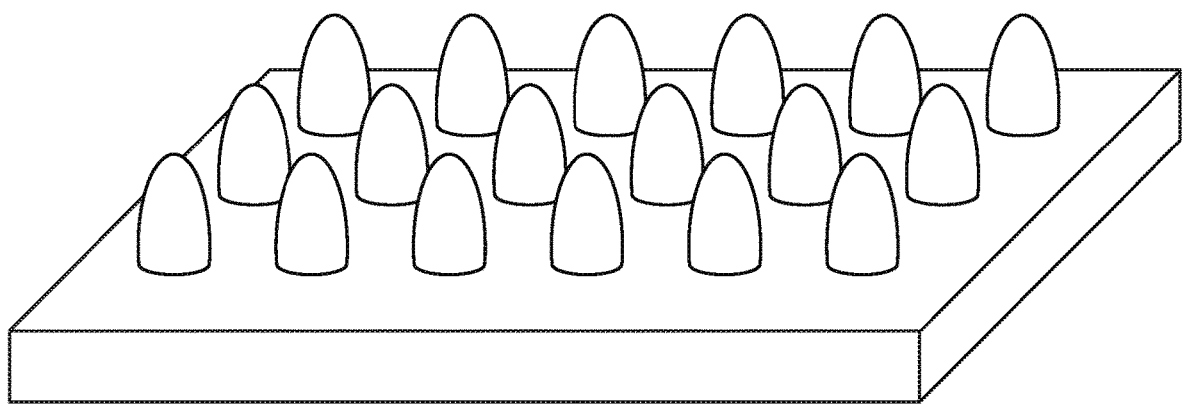
FIG. 6 is an illustration of an electrode design having electrodes designed to penetrate the stratum corneum layer of the skin epidermis.

Referring to FIG. 6, in some embodiments, the electrode may consist of a large number of conductive segments that project from the skin-contacting surface of the patch. This design allows the electrode to penetrate through the epidermal layer, instead of simply contacting the stratum corneum of the skin. In addition to providing better contact to the conductive tissue, the design of FIG. 6 is expected to provide more uniform delivery of the electrical stimulation. The electrode optionally may be pre-coated with liquid or gel to deliver an analgesic or an antibiotic such as neomycin or polymyxin.

Referring again to FIG. 3, power source 22 may be attached to/embedded in outer housing 18, or alternatively, attached to/embedded in tissue contact substrate 20. For example, power source 22 may be a 9-volt battery, a button cell battery, a rechargeable battery or any other type of battery. In other embodiments, power source 22 may be one or more photovoltaic panels positioned on an outer surface of outer housing 18. In yet another embodiment, outer housing 18 may include a plug for attaching a smart phone (or other power source) to skin patch 12, and the smart phone (or other power source) may be used to charge power source 22 or may even be used as power source 22. In yet another embodiment, magnetic coupling may be used as power source 22. In that embodiment, transmitter coils may be placed over outer substrate 18 or at a distance to power skin patch 12. In still another embodiment, power may be generated by converting kinetic energy into electrical current, which may be stored on a capacitor. As a further alternative, skin patch 22 may be powered by plugging a power cord attached to it into a power supply, such as an electrical outlet or a separate power source.

Sensor 15 disposed on patch 12 may be one or multiple devices. Illustratively, sensor 15 is described as disposed on skin patch 12, although in alternative embodiments sensor(s) 15 may be configured for placement in a separate location on the patient, spaced away from the skin patch 12 (i.e., separate sensor device(s) 14 of FIG. 2). Most, if not all, of the sensors described below may be included in system 10 as part of skin patch 12, as one or more separate sensors 14, or both. In any given embodiment, any combination of sensor(s) 15 and separate sensor device(s) 14 may be used. For ease of description and understanding, sensor devices will be referred to below as sensor 15, any of the specific embodiments below may be combined in any suitable combination in muscle contraction stimulation system 10.

As noted above, a preferred sensor 15 disposed on skin patch 12 is a muscle contraction sensor. This may be, for example, an accelerometer to sense motion associated with muscle contraction. Another type of sensor 15 is a muscle integrity sensor, which could sense when a muscle is beginning to break down, such as during rhabdomyolysis. Markers of rhabdomyolysis, any of which may be sensed by one or more sensors 15, include hyperkalemia (may be sensed via ECG), hypocalcemia (may be sensed via ECG), muscle edema (may be sensed via muscle impedance), elevated creatine phosphokinase (CPK) levels (CPK released from damaged muscle), or an EMG or MMG reading indicating muscle damage. Another exemplary type of sensor 15 is a muscle fatigue sensor. Sensor 15 alternatively may include one or more vital signs sensors, which monitor respiratory rate, heart rate, blood pressure or temperature. Physiological parameters also may be used to guide the therapy or for safety purposes. For example, ECG signals may be used to synchronize the timing of the contraction of the skeletal muscles to the cardiac cycle, for example in heart failure therapy. On the other hand, anytime the heart rate is outside predefined limits, the therapy may be automatically turned off for safety. Other physiologic parameters include markers of sympathetic drive, such heart rate variability, pilo-erection (goose bumps), perspiration, and muscle sympathetic nerve activity.

Sensor 15 also may include a skin contact sensor. Such a sensor 15 is located on a skin contact surface of patch 12, near one or more electrodes 36, and is configured to detect whether an adequate contact has been made between tissue contact substrate 20/electrodes 36 and the patient's skin. If adequate contact is achieved, the therapy can be started, but if adequate contact is not established, the patient may receive a message on patient interface unit 16 indicating that he/she needs to reposition, apply pressure, or adjust skin patch 12.

In other embodiments, sensor 15 may be used to sense one or more metabolic parameters, such as glucose level detected via an implantable, percutaneous, transcutaneous, or corneal blood glucose monitor. It may be important to detect changes in glucose levels for a therapy designed to treat diabetes, so that the therapy may be titrated based on the glucose levels and/or terminated when an end goal is reached. Therapy may be integrated with various insulin delivery methods, including injections, pump based delivery, and inhaled and oral formulations. Furthermore, such information may be provided to health care professionals, to help them personalize the treatment for each individual based on his or her specific needs. In some embodiments, the "end goal" of diabetes therapy may be reached when glucose falls below a set level (e.g. 100 mg/dL), or once a threshold for insulin sensitivity has been reached. Markers of insulin sensitivity include skin sympathetic nerve activity, motor nerve conduction speed, RR interval (inversely correlated with HOMA-IR, Homeostatic Model Assessment of Insulin Resistance), and muscle capture threshold (increases with increasing blood insulin).

Sensor 15 also may include one or more sensing devices that detect biomechanical parameters, such as position and activity related measurements. For example, if sensor 15 detects that a patient is walking, then system 10 may be programmed to discontinue muscle contraction stimulation, so that it does not interfere with the act of walking. A local ballistocardiogram may be used for the detection of arrival of the blood pressure at an extremity. A goniometer may be used to measure the angle of a joint (e.g. knee, hip, etc.).

Any of a number of different types of sensors 15 may be used to detect one or more of the patient parameters described above. An impedance sensor, for example, uses the electrical impedance measured between electrode sets to assure that the electrodes are in electrical contact with the skin and to detect changes in the tissue volume and tissue composition. During contraction of the muscle, both the shape and the composition of the muscle changes, which in turn changes the impedance signal. For example, when contracted, the muscle contains less blood, which can be detected as a reduction in the overall conductance since the electrical conductivity of blood is approximately 0.8 Siemens/meter while the electrical conductivity of muscle is approximately 0.1 Siemens/meter. Similarly, a sudden increase in electrical impedance may indicate that electrode contact with the tissue is too weak. When impedance sensing is conducted using electrodes near the chest area, such as when using an ECG sensor, the resulting changes in the transthoracic impedance measurement may be used to determine the respiratory rate of the patient.

A temperature sensor may be used to measure ambient temperature, and/or to estimate the caloric heat produced by a stimulated muscle. Furthermore, the changes in the local temperature might be due to local heating under electrodes 36, which may be due to loss of conductive gel, indicating the need for replacement of skin patch 12.

An EMG sensor uses electrodes to detect signals coming from the skeletal muscle as it contracts. Electromyogram would not only show that the muscle is contracting, but would also indicate the strength of the muscle contraction resulting from the application of the electrical stimulation. The evoked response of the skeletal muscle shows two distinct features, known as the M-wave and the H-wave. The M-wave arrives within 5 milliseconds after the application of the electrical stimulation, and its amplitude is proportional to the strength of the muscle contraction. The H-wave appears 20 milliseconds after application of the electrical stimulation, and its amplitude decreases as the strength of the muscle contraction increases. In one embodiment, the amplitude of the M-wave is used to estimate the strength of the skeletal muscle contraction. In other embodiments, the ratio of M-wave amplitude to H-wave amplitude is used to measure muscle contraction.

An ECG sensor may be used to detect the electrical activity of the heart muscle, and in particular, to detect P, QRS and T waves using two or three electrodes. In some embodiments, the skin patch 12 may include an ECG sensor, in order to detect heart signals so that system 10 will know when a patient might have accidentally placed skin patch 12 over the heart. In such an instance, system 10 would detect the nearby presence of the heart and would not allow itself to activate/stimulate. An ECG monitor also may be an example of separate sensor device 14, as discussed previously.

A pressure sensor also may be used, in some embodiments, to measure changes in external pressure. If outer substrate 18 is held in place with an elastic bandage covering the entire extremity, for example, then contraction of the muscle would yield in an increase in the measured pressure. A goniometer may be used, in some embodiments, to measure a joint flexion or extension angle, such as the angle of an elbow, shoulder, wrist, ankle, hip, or a knee. Based on the joint angle, control unit 24 may adjust the stimulation amplitude or instruct the patient to change the joint angle.

An accelerometer may be used to monitor motion and produce signals that help detect muscle contraction. For example, upon contraction, the skeletal muscle bulks, creating an expansion in the radial direction of the muscle. Hence, the stronger the contraction, the stronger would be the signal coming from the accelerometer. In various embodiments, one-dimensional, two-dimensional or three-dimensional accelerometers may be used, as well as any combination thereof.

Any other suitable sensors 15 may be used in system 10, according to various alternative embodiments. For example, blood flow in the muscle may be measured using ultrasonic or ultrasound sensors, which would not only show immediate changes in the blood volume in the muscle resulting from the contraction, but also would show changes in the resistance of the vascular bed following long term contraction of the muscle. Similarly, electrical activity of the afferent and efferent nerves may be monitored, to assess the results of the electrical stimulation that is applied to muscles that are proximal and distal to the sensing location. Signals coming from the sensors are processed by signal processing unit 28 before being presented to control unit 24.

One of the sensors that the invention may advantageously use is a mechanomyogram (MMG) sensor that detects mechanical motion of the muscle during a contraction. An MMG sensor can be a type of a microphone or an accelerometer. It is generally placed over the muscle to be stimulated so that contractions may be detected by the MMG sensor and recorded. Signals from the MMG sensor may be processed by the signal processor to extract the root mean square (RMS) and frequency domain power information to be interpreted by control unit 24. An MMG sensor may provide multiple types of feedback to the control unit, including strength of a contraction and muscle fatigue status.

Signal processing unit 28 extracts information from the signals coming from sensor(s) 15 and separate sensor device(s) 14 and presents the resulting data to control unit 24. Signal processing unit 28 represents one embodiment of processor 16, which was described generically above in reference to FIG. 1; alternatively, signal processing unit 28 and controller 24 together may be viewed as corresponding to processor 16 of FIG. 1. Signal processing unit 28 may extract the absolute value of the electrical impedance, using an impedance sensor, which may be used for the confirmation of muscle contraction as well as to assess the strength of a given muscle contraction. This information also may be used to estimate tissue volume (plethysmography), which changes during muscle contraction. Alternatively, signal processing unit 28 may use the tissue impedance signal to determine the contents of the tissue producing the impedance signal. Since conductivity of tissues varies, depending on tissue type, one can determine the changes in tissue composition. For example, approximate values of conductivity of the following tissues are: blood 0.8 Siemens/meter; bone 0.02 Siemens/meter; fat 0.05 Siemens/meter; heart muscle 0.1 Siemens/meter; and skeletal muscle 0.1 Siemens/meter. During contraction of a muscle, the amount of blood in the muscle is reduced, thereby resulting in a decrease in tissue conductivity or increase in impedance.

Signal processing unit 28 also may perform additional functions. It may extract temperature information from a temperature sensor and present it to control unit 24 after low pass filtering it. Signal processing unit 28 may process signals from an EMG sensor to spectroscopically analyze the signals, such that the resulting frequency domain signals may be used to detect the onset of fatigue. For example, when a muscle fatigues, the center frequency shifts, which may be interpreted as a condition requiring the termination of the therapy, or change in the stimulation frequency to prolong the therapy session. Signal processing unit 28 also may process signals coming from an EMG sensor to calculate estimates of the cross correlation of multiple EMGs, the auto-correlation and the spectral density of EMGs, and the cyclic frequency spectral density of EMGs. Information from these measurements may be used by control unit 24 to infer fatigue status of the skeletal muscles that are being stimulated.

Signal processing unit 28 also may be used to process signals coming from an ECG sensor to extract information used by system 10, such as heart rate. Heart rate detection may be performed by measuring the R-R interval of the electrocardiogram. If the heart rate is determined to be outside of a predefined range, a hazardous condition is assumed to exist, and the therapy preferably is halted by control unit 24. Signal processing unit 28 also may look for "peaked" T waves and a shortened QT interval, to lengthening PR interval and loss of P waves, and then to widening of the QRS complex, culminating in a "sine wave" morphology, all of which could be a sign of hyperkalemia resulting from rhabdomyolysis. Signal processing unit 28 may look for the narrowing of the QRS complex, reduced PR interval, T-wave flattening and inversion, prolongation of the QT-interval, appearance of a prominent U-wave, as well as a prolonged ST duration and ST-depression, all of which could be signs of hypocalcemia resulting from rhabdomyolysis.

Signal processing unit 28 may extract information from a strain gauge pressure sensor and present it to control unit 24 after low pass filtering it, so that the strength of a contraction can be inferred. It also may extract joint angle information from a goniometer and present it to control unit 24 after low pass filtering it, so that the angle of flexion or extension of a joint can be calculated. Signal processing unit 28 also may extract acceleration information from an accelerometer and present it to the control unit 24 after low pass filtering it, so that the strength of muscle contraction can be calculated from the peak value of the resulting trace. Signal processing unit 28 may extract fatigue information from the MMG signal and present it to the control unit 24, so that the therapy session can be terminated before any damage to the muscle takes place. Further, the rate of contraction may be used to assess the state of muscle fatigue.

Communications unit 26 provides bidirectional communication between control unit 24 and patient interface unit 16. Such communication may be achieved using wired techniques, such as USB, I2C, SPI or RS-232, or wirelessly. Wireless connections may be established using techniques such as but not limited to WiFi, Bluetooth or Zigbee, or by other radio frequency (RF), optical or acoustic telecommunication methods.

Control unit 24 is responsible for the coordinating operation of the other components of skin patch 12, such as electrical stimulation unit 32 and communications unit 26. It also governs the execution of the therapy protocol. Control unit 24 may include a combinational logic circuitry or microprocessor circuitry, such as a PIC 16F690, along with other components, such as a memory chip. Control unit 24 generates the logic signals necessary to govern the operations of the switches shown in subsequent figures that interconnect the electrodes to stimulation unit 32.

In some embodiments, control unit 24 may drive electrical stimulation unit 32 to produce a high frequency stimulation for pain suppression. This stimulation may be distinct from the stimulation used for the excitation of the motor points of the skeletal muscles. For example, the high frequency stimulation may be applied at frequencies in the range of about 10 KHz to about 200 KHz. Electrical stimulation unit 32 also may deliver a combined waveform having a low frequency square wave and high frequency sine wave bursts, where the high frequency sine wave bursts penetrate deep into the tissue and cause the stimulation of the motor point. In that case, the combined waveform may be interrupted periodically, for the sensing of EGM and ECG waveforms. In other embodiments, control unit 24 may drive electrical stimulation unit 32 to reduce the frequency of the electrical stimulation to decrease the muscle fatigue following stimulation at a higher frequency. Control unit 24 also may cause electrical stimulation unit 32 to reduce the amplitude of stimulation after a period of time.

Patient interface unit 16 may, in some embodiments, be an application that is downloaded for use on a smart phone, tablet, laptop computer or other smart device. Other types and configurations of patient interface units 16 may be used in alternative embodiments of system 10, including dedicated devices. In its simplest form, patient interface unit 16 as depicted in FIG. 3 may include "pain" button 17a on a smart phone screen (or other touch screen), which is pressed by the patient anytime he/she feels pain in response to nerve stimulation by system 10. The illustrated embodiment also includes "no pain" button 17b, which is optional. Alternative embodiments may include additional features that allow a patient to input further information and/or adjust a treatment, such as to turn system 10 on and off, set timing of a therapy, adjust strength and/or frequency of contractions, pulse width, pulse shape, pulse frequency, pulse train rate, pulse train duration, duty cycle, wave form, voltage, etc. Some embodiments also may provide information to a patient, such as physiological information (pulse, blood pressure, muscle fatigue, etc.) and/or information about the therapy he/she is receiving. All of these further features are optional, however.

In some embodiments, patient interface unit 16 may provide instructions and questions to the patient on digital displays, audio channels or by illuminated signs, while patient responses are entered via electrical switches, touch screens or speech recognition. In some embodiments, patient interface unit 16 is capable of handling, for example, up to 16 external packages, i.e., patches 12 and/or sensors 14, at a time with unique codes. Patient interface unit 16 may collect data regarding system 10 operation, patient compliance and/or patient outcomes, and it may store such information. Patient interface unit 16 also may log the status of muscle training, amount and duration of the stimulation being applied, and/or patient compliance with the treatment. Any of this recorded information may be made available to medical professionals continuously or periodically, by downloading it via wired or wireless networks. Furthermore, the resulting data may be transmitted to a central location for overall evaluation and eventual distribution to the clinical sites. Algorithms running on a central computing warehouse may be used to determine best practices for stimulation and patient outcomes for implementation in the future versions of the medical device. Patient interface unit 16 also may be used to govern a stimulation pattern for a patient, based on a particular therapy regimen. If necessary, all muscles are stimulated simultaneously, or stimulated sequentially, or randomly. Furthermore, the stimulator may alternate sites of stimulation such as alternating the legs that are being stimulated, to reduce fatigue, to prolong treatment duration and/or to accommodate the physiological needs of the patient. In patients with active medical devices, such as cardiac pacemakers, implantable cardioverter defibrillators (ICDs), cardiac resynchronization therapy (CRT) devices, as well as combinational devices, such as CRT-D, or insulin pumps or continuous glucose monitors, patient interface unit 16 may be configured to communicate with the active medical device(s), to obtain vital information, such as the heart rate and timing of an ECG, such as the marker channel and blood glucose levels.

Figure 7:
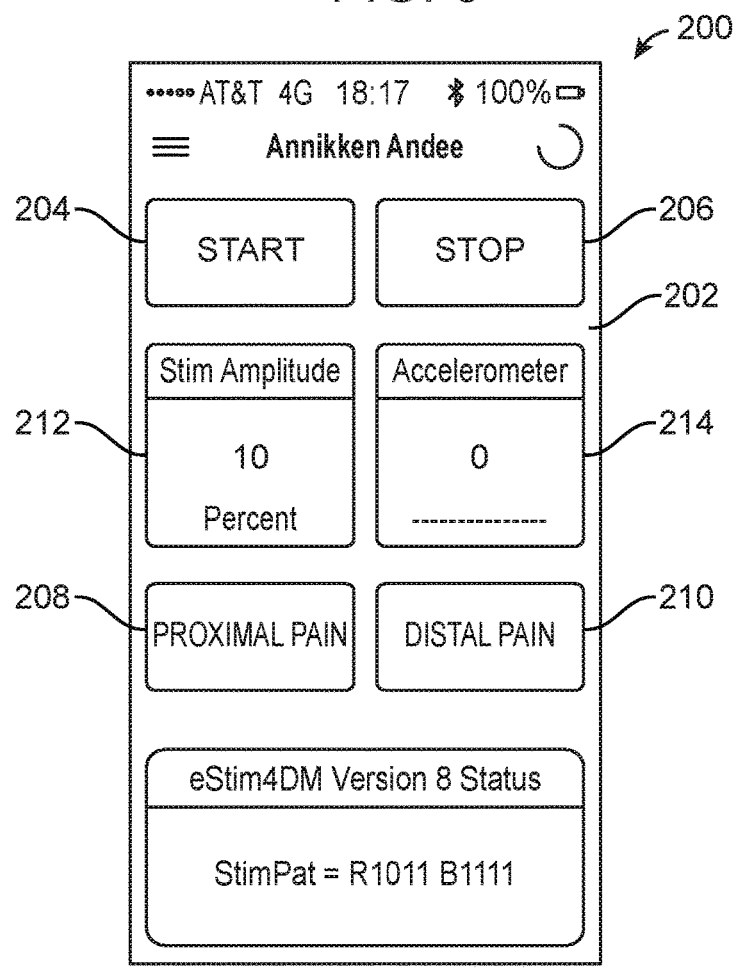
FIG. 7 is a view of a display screen of a patient interface unit showing controls and parameter settings used for the processor of the muscle stimulation system.

Referring now to FIG. 7, display 202 of another exemplary embodiment of a patient interface unit is described. Patient interface unit 200 is depicted as a conventional smart phone running an application loaded onto the smart phone. In this embodiment, display 202 includes start button 204, stop button 206, proximal pain button 208, distal pain button 210, stimulation amplitude window 212, accelerometer window 214 and treatment status window 216. In this embodiment, therefore, patient interface unit 200 allows the patient to stop and start a therapy session, via buttons 204 and 206, and input pain feedback, via buttons 208 and 210. The patient also may view information coming from the rest of system 10 (such as from skin patch 12), regarding a current therapy session and which electrodes are active at any given time. This example illustrates that any given embodiment of the patient interface device may include suitable mechanisms for receiving patient input and providing information to the patient.

Skin patch 12 of system 10 may include additional electronic and/or mechanical features. For example, as described above, skin patch 12 may include multiple sensors 15 of the same or different types. Skin patch 12 also may include a cooling device as part of tissue contact substrate 20 that cools the skin during therapy. Such cooling may help alleviate pain and discomfort, may induce vasoconstriction in the skin to help reduce fluid content underneath electrodes 36, or both. Cooling may be achieved using a chemical compound, such as an ionic salt or urea dissolved in water or an ammonium nitrate mixture, or via a mechanical device, such as Peltier coolers or evaporative coolers. Cooling also may be delivered to range of locations relative to the stimulation electrodes, including under, between, lateral to, adjacent to, proximal to the distal electrode and distal to the proximal electrode, distal to the distal electrode and proximal to the proximal electrode.

Prolonged use of a skin patch is not advisable as the gel may become degraded over the course of a therapy session by dead skin cells or perspiration, thus leading to suboptimal therapy if the skin patch is used for a subsequent therapy session. In addition, use of a skin patch that is not a genuine product (e.g. counterfeit or made by an unauthorized third party without appropriate quality control) could also compromise patient safety and reduce the efficacy of the therapy that is being delivered. To address this concern, the embodiment disclosed in FIG. 8 includes an embedded RFID chip that prevents reuse of a skin patch while also eliminating the possibility of using a skin patch from an unapproved source. In such an embodiment, the outer substrate may include an RFID reader that confirms whether the skin contact substrate is genuine and/or was previously used. Connection between the RFID chip and the RFID reader could be a wired or a wireless link. In either case, the control unit of the outer substrate may interrogate the RFID chip of the skin patch to obtain a unique skin patch ID number, or USPID. If no RFID is detected, then a report is sent to the patient interface unit to inform the patient to couple a new, unused genuine skin patch to the outer substrate. If a USPID is present on the skin contact substrate and read, then the USPID is transmitted to the patient interface unit where it is subjected to a test which includes the application of a mathematical formula to determine if the USPID is a valid number. If the USPID is a valid number, the therapy session is initiated and the USPID is stored in the non-volatile memory of the patient interface unit. If the USPID is not a valid one, or it is a number that was seen previously by the patient interface unit, then the patient interface unit instructs the patient to replace the skin contact substrate.

Figure 9:
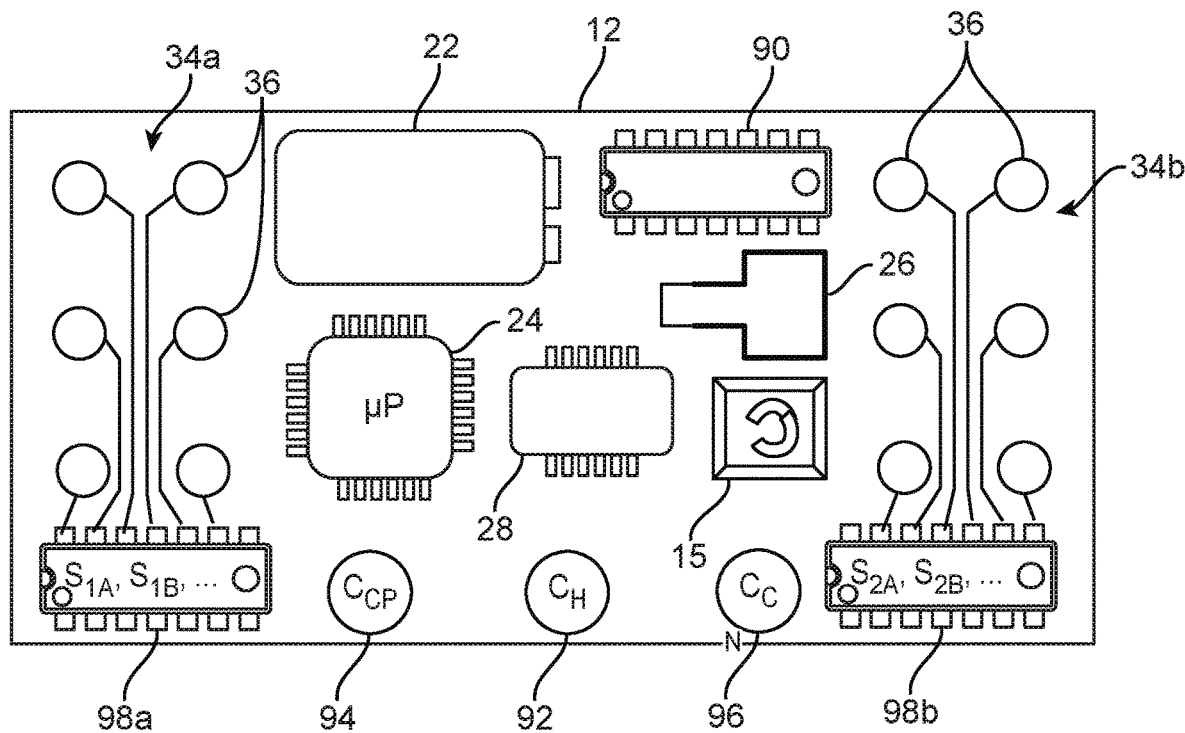
FIG. 9 is a plan view of a layout of electronic components on a skin patch of a muscle contraction stimulation system in accordance with one embodiment of the present invention.

Referring now to FIG. 9, an exemplary detailed layout of electronic components for the skin patch 12 of FIG. 3 is described. The various electronic components may include power source 22 (e.g., a 9 Volt battery), control unit 24, signal processor 28, communications unit 26 (including an antenna), sensor 15 (such as an accelerometer and/or other sensor(s) discussed above), and electrode sets 34a, 34b, or electrical contacts for the electrodes, wherein each electrode set includes six electrodes 36. Skin patch 12 may in addition include voltage multiplier 90, holding capacitor 92, coupling capacitors 94, 96, and two sets of switches 98a, 98b, which control delivery of signals to electrode sets 34a, 34b.

Figure 10:
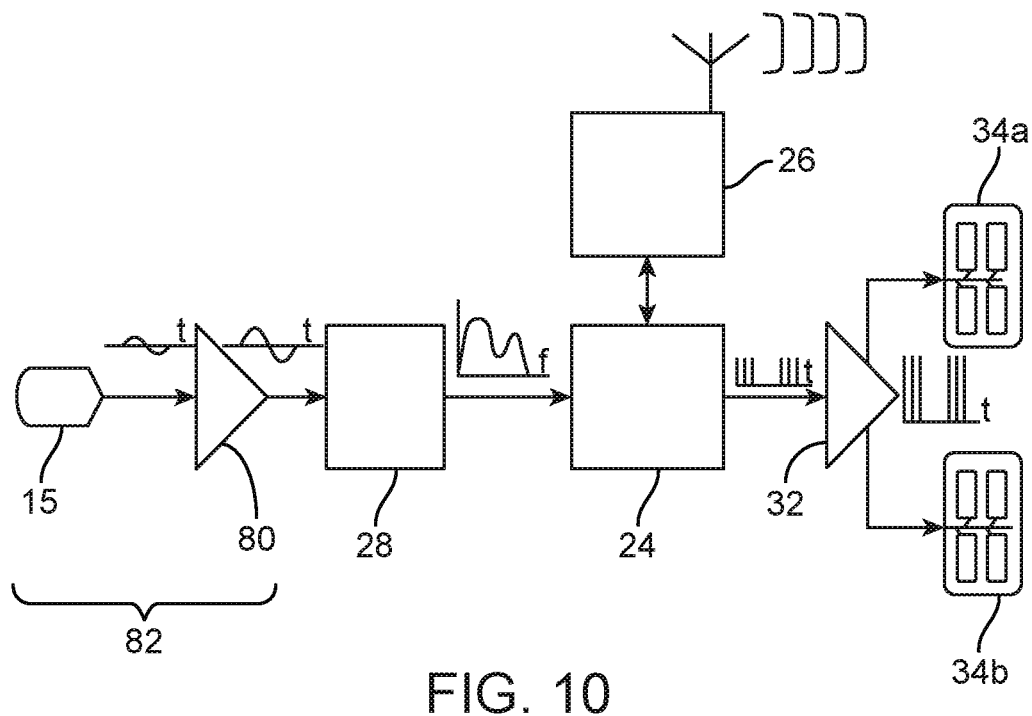
FIG. 10 is a diagram illustrating the flow of electrical signals between the electronic components of a skin patch portion of a muscle contraction stimulation system.

Referring now to FIG. 10, information flow within skin patch 12 is described. Information from sensor 15 may be amplified by an amplifier 80, which together may be referred to as sensory feedback unit 82. Sensed, amplified signals pass to signal processor 28, and processed signals then pass to control unit 24. Control unit 24 may transmit signals to, and receive signals from, communication unit 26, and communication unit 26 in turn transmits signals to, and receives signals from, patient interface unit 16 and control unit 24. Based on a variety of different inputs input to control unit 24, such as information identifying the patient, degree of muscle fatigue, whether to begin or cease therapy, etc., the control unit sends signals to electrical stimulation unit 32, which provides signals to electrode sets 34a, 34b to stimulate nerve tissue and thus stimulate muscle contractions.

Figure 11:
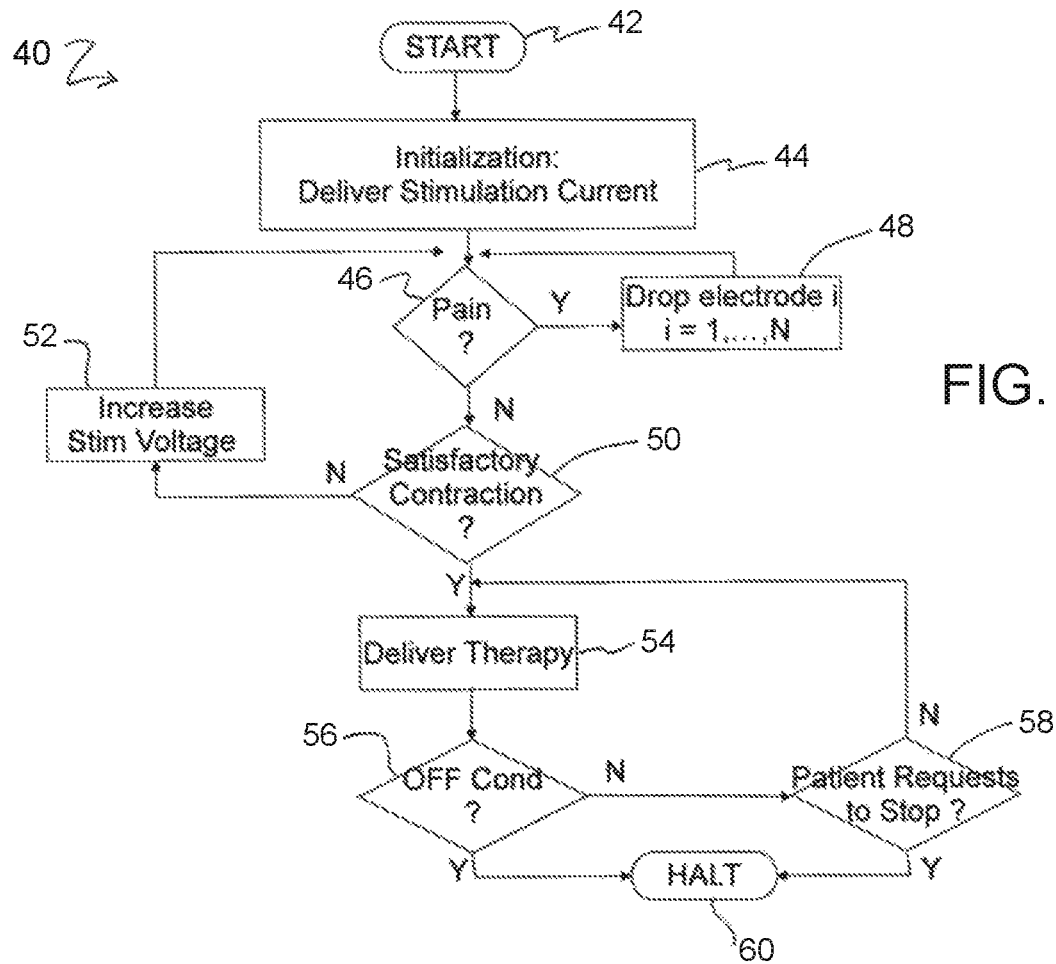
FIG. 11 is a flow chart illustrating a method for delivering muscle contraction stimulation therapy in accordance with one aspect of the present invention.

Referring now to FIG. 11, a muscle contraction stimulation method in accordance with the principles of the present invention is described using muscle contraction system 10. In a first step of method 40, system 10 is activated by entering a start command at step 42. In this embodiment, at initiation of skin patch 12, all electrodes 36 of electrode sets 34a, 34b are activated, and a stimulation voltage is set to a minimum value, such as 3 Volts. Next, initialization step 44 is performed, which may include a test stimulation (delivery of current toward the target nerve tissue), to detect whether skin patch 12 is adequately and correctly adhered to the patient's skin to be able to deliver stimulation therapy. The test stimulation also helps determine if the patient will feel pain during stimulation therapy. If the test stimulation produces pain 46, the patient inputs feedback to that effect using patient interface unit 16. At that point, control unit 24 will drop one electrode 36 from each of the two electrode sets 34a, 34b at step 48, and will then deliver a new stimulation current to the revised electrode sets 34a, 34b. If the patient again reports pain at step 46, another electrode 36 is dropped at step 48 and current delivered again. This process continues until the patient no longer reports pain. If no further electrodes 36 can be eliminated, and the patient still reports a significant pain sensation, then an instruction may be provided to the patient, via patient interface unit 16, to reposition skin patch 12. Method 40 then restarts from the beginning with initialization step 44.

At step 50, muscle contraction stimulation system 10 determines whether the delivered current produces a satisfactory muscle contraction. This is done with the feedback signals coming from signal processing unit 28, which in turn obtains its inputs from sensor(s) 15. If a satisfactory contraction is not achieved, system 10 increases stimulation voltage at step 52 and repeats delivery of current. In some embodiments, the stimulation amplitude may be gradually increased, until strength of the muscle contraction is sufficient. In an alternative embodiment, a binary search algorithm may be used, in which case a correct stimulation amplitude is found by continuously sectioning the stimulation range. Once sufficient current has been delivered to produce a satisfactory contraction and the patient is not reporting pain, then system 10 is ready to deliver therapy at step 54.

System 10 then delivers muscle contraction stimulation therapy until an off condition is met at step 56 or the patient requests via patient interface unit 16 that the therapy stop at step 58. When either of these two conditions is reached, therapy stops, step 60. Any of a number of different conditions may trigger a halt to therapy. For example, a predetermined end time for therapy may be reached, a therapy goal may be achieved, the patient may start moving, such as walking or standing, or a hazard condition may occur.

Hazard conditions include any damage to the muscle, such as rhabdomyolysis, muscle fatigue, worsening vital signs, such as changes in blood pressure, heart rate or respiratory rate, or other markers of changes in sympathetic drive.

As part of initialization step 44 or as a separate process, method 40 may include one or more additional test stimulations. One purpose/type of test stimulation may be performed to confirm that skin patch 12 is adequately attached to the skin in a desired location for providing therapy. Another purpose/type of test stimulation may be performed to ensure that skin patch 12 is not positioned directly over the heart or too near to the heart, such that stimulations may affect heart function.

Control unit 24 plays a significant part in the operation of muscle contraction stimulation system 10 and method 40. For example, in some embodiments, it may monitor power source 22 and issue an alert, if the power level is getting too low. If the user does not take an action, control unit 24 automatically shuts off the system to prevent any erroneous operation. Control unit 24 may communicate with patient interface unit 16, to pose questions to the user, such as, "Is the pain tolerable?" Control unit 24 also may receive interrupts from patient interface unit 16, such as a request to terminate the therapy. Communications between control unit 24 and patient interface unit 16 are provided by communications unit 26. Control unit 24 also may check the quality of electrodes 36, to assure an adequate safety margin. If tissue contact substrate 20 is not a genuine part or has been used previously (and is designed to be disposable), control unit 24 may issue an alert to the patient, via patient interface unit 16, asking for replacement of tissue contact substrate 20 with a new, genuine part. Control unit 24 may conduct additional tasks related to the signals coming from sensors 15 and signal processing unit 28. For example, control unit 24 may calculate heart rate variability, as reductions in heart rate variability are undesirable for patients with various conditions.

Figure 12A:
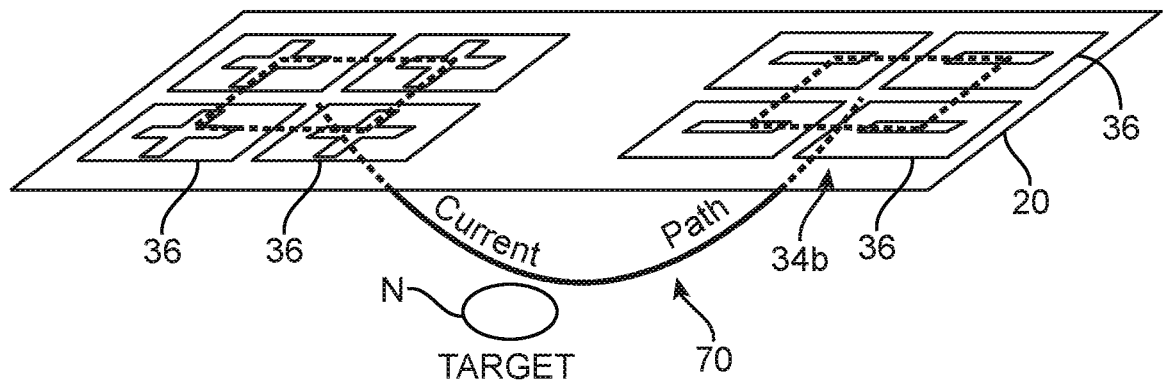
FIGS. 12A and 12B are diagrammatic, perspective views of an electrode pad illustrating a path of current traveling between electrode sets on the pad, wherein current path changes as a result of elimination of some electrodes employed in the stimulation therapy.
Figure 12B:
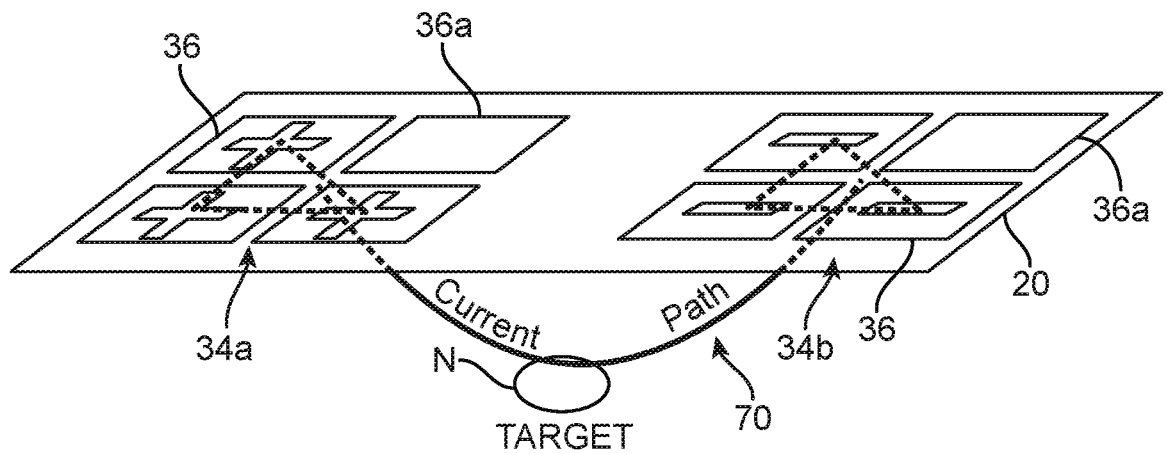

Referring now to FIGS. 12A and 12B, a simplified diagram depicting a portion of method 40 is described. FIG. 12A shows tissue contact substrate 20 with current path 70 traveling from positive electrode set 34*a* to negative electrode set 34*b*. In FIG. 12A, all four electrodes 36 of each electrode set 34*a*, 34*b* are activated. In this example, current path 70 is too shallow and does not contact and stimulate the target nerve tissue N. It also may (or alternatively) be the case that the delivered current with all electrodes 36 activated causes the patient to feel pain. In FIG. 12B, as initiated by step 48, electrode 36*a* is turned off in each electrode set 34*a*, 34*b*, which changes the shape and trajectory of current path 70, thus contacting and stimulating the target nerve tissue N. If the current configuration depicted in FIG. 12B still causes the patient to feel pain, a new configuration of on and off electrodes 36 could be tried next. As mentioned above with respect to FIG. 11, the process of delivering a stimulating current, receiving feedback regarding muscle contraction and patient pain, turning on/off electrodes 36 of sets 34*a*, 34*b*, and delivering a new stimulating current, may be repeated as many times as necessary. By turning on and off various electrodes 36 in electrode sets 34*a*, 34*b* in this manner and delivering test stimulation currents with each new electrode configuration, a desired combination of electrodes 36 may be achieved, based on effective stimulation of nerve tissue to cause muscle contraction and on minimal pain felt by the patient. System 10 may use any suitable algorithm for selecting which electrodes 36 to turn off and/or on, to arrive at a desired combination of electrodes 36.

Figure 13:
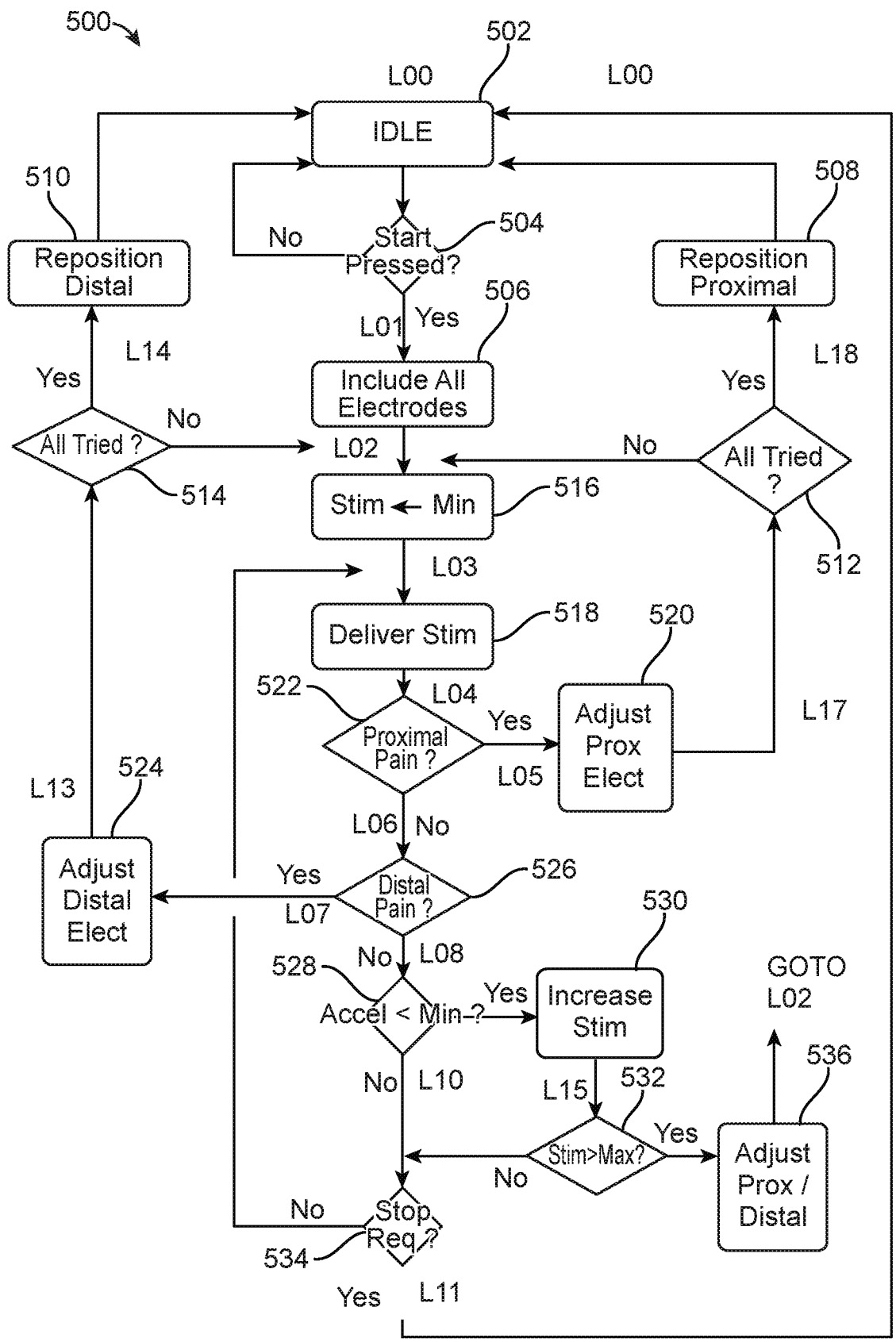
FIG. 13 is a flow chart illustrating an alternative muscle contraction stimulation method of the present invention.

In accordance with another aspect of the present invention, with respect to FIG. 13 a more detailed muscle contraction stimulation method 500 is described. At the start of method 500, system 10 is in IDLE mode 502 (L00). Once the user pushes the START button on patient interface unit 16, at step 504, the system moves into the pathway L01. Initially, all electrode segments are included (all segments are active) at step 506, and system 10 moves to pathway L02 of the program. Stimulation amplitude is set to a minimum value at step 516, which is 10% of the maximum value, and system 10 moves to pathway L03. At this point, stimulation is delivered, step 518, and data from sensor (for example, a 3D accelerometer) is measured. Total acceleration may be determined from a low pass filtered version of the original acceleration signals (X, Y and Z), using an infinite impulse response (IIR) filter implemented in firmware. After the conclusion of the stimulation (pathway L04), system 10 interrogates patient interface unit 16, to see if the user has pushed a button indicating pain sensation associated with the proximal electrode set, at step 522 or distal electrode set, step 526 (see, for example, patient interface unit 200 in FIG. 7). If the patient reports a pain sensation for the proximal electrode set, at step 522 (pathway L05), then the pattern of the electrode segments in the proximal set is rearranged at step 520 (pathway L17), and stimulation procedure is restarted from step 516 (pathway L02). If all proximal segments have been tried by this point, step 512, a message is delivered to patient interface unit 16, instructing the user to reposition the device, step 508, at least its proximal section, and the system is returned back to IDLE state 502 (pathway L00) and will stay there until the user again pushes Start button 504 on patient interface unit 16.

Similarly, if pain is reported as being associated with the distal electrode set at step 526 (pathway L07), then the pattern of the electrode segments in the distal set is rearranged at step 524 (pathway L13), and stimulation procedure is restarted from program location at step 516 (pathway L02). If all proximal segments have been tried by this point, step 514, a message is delivered to patient interface unit 16, instructing the user to reposition the device, at step 510, at least its distal section, and the system returns to IDLE state 502 (pathway L00) and stays there until the user again pushes Start button 504 on patient interface unit 16.

If no pain indication is received, then the strength of the muscle contraction determined using the accelerometer is compared against a minimum value at step 528 (pathway L08). If the contraction is strong enough, then it is concluded that the muscle has contracted (pathway L10). Otherwise (pathway L09), stimulation amplitude is increased at step 530 (pathway L15). If the stimulation was already at maximum available voltage, then the patterns of the proximal and distal electrodes are readjusted, at step 536, and the system is returned to step 516 (pathway L02). If the new stimulation amplitude is less than the maximum allowed (pathway L10), then patient interface unit 16 is interrogated to determine if the user has requested to end the therapy, step 534. If a Stop request is detected (pathway L11), then the system returns back to Idle state, at step 502 (pathway L00). Otherwise, method 500 returns to step 518 (pathway L03) for the next stimulation. Advantageously, the foregoing algorithm automatically determines the stimulation threshold, allowing delivery of minimum energy to the tissue to achieve the desired therapeutic outcome. By keeping the stimulation energy to the minimum needed to cause muscle contraction, battery life is prolonged and he possibility of unintentional stimulation of sensory nerves, as well as motor nerves of non-target muscles, is reduced.

Figure 14:
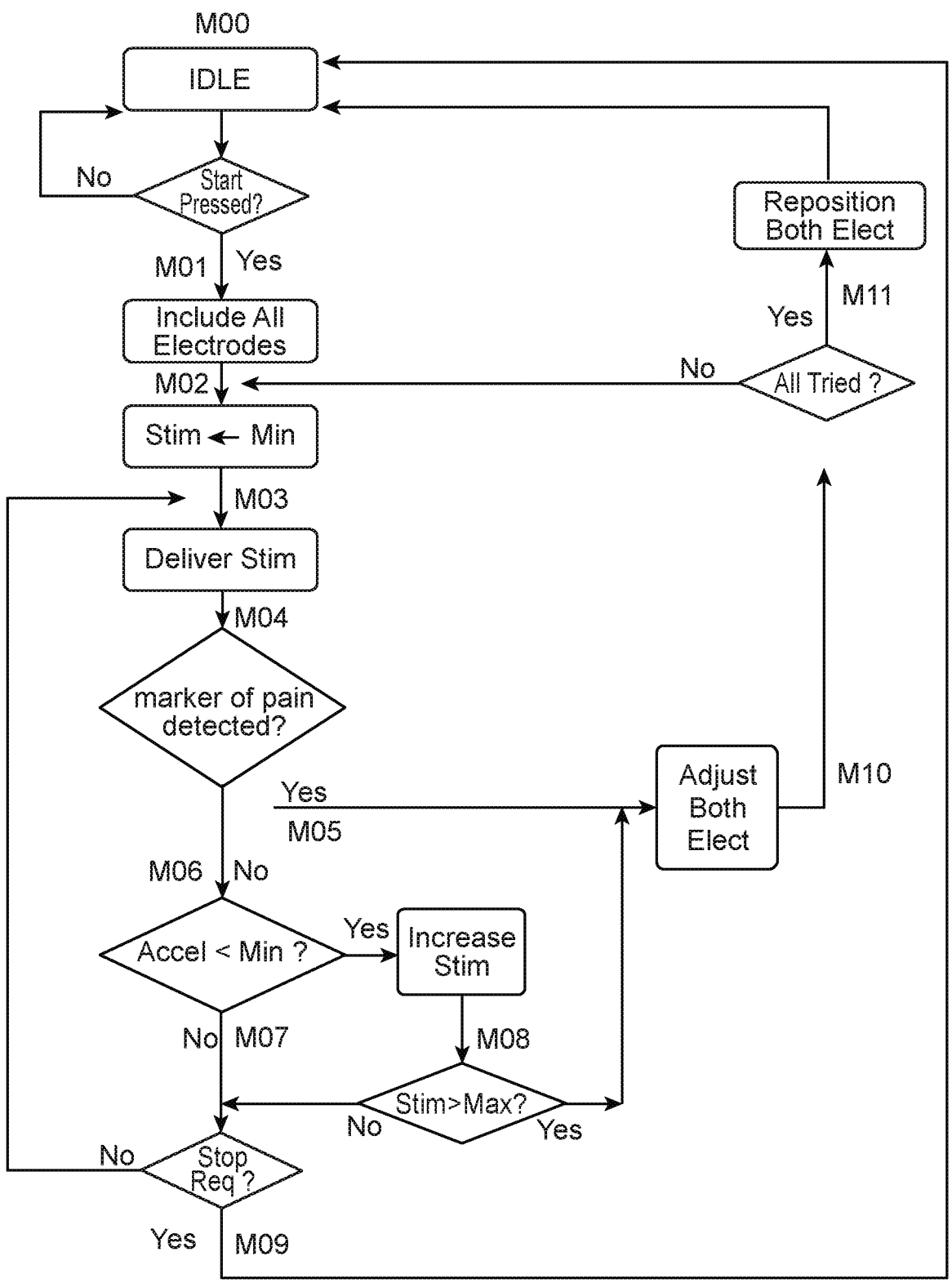
FIG. 14 is a flow chart illustrating a further alternative muscle contraction stimulation method of the present invention.

Referring now to FIG. 14, a modified version of a method of operation is described, which provides benefits similar to those of method 500 of FIG. 13, but in addition eliminates the need for the patient to participate in determining the optimal electrode pattern and the current pathway. Instead the method of FIG. 14 determines the electrode pattern and stimulation amplitude automatically. Method 550 starts at the idle state (step M00) and remains there until the Start button is pressed. Once the Start button is pressed (at step M01), the algorithm starts with the inclusion of all electrodes and setting the stimulation amplitude to the lowest setting (step M02), which is followed by the delivery of the stimulation (step M03). At the next step, step M04, a marker of the patient's pain sensation is detected as described below. Multiple markers of pain sensation also may be used. If sufficient pain is detected (step M05), then the pattern of both electrodes are adjusted (step M10). If all electrodes have not yet been tried, then the algorithm returns back to stimulating, starting from the lowest amplitude (step M02). If all permutations of the electrode pattern has been tried (step M11) then the subject is instructed to reposition both electrodes and the system reverts to the Idle state (step M00) until the subject re-initiates the search algorithm. If the pain indication was low (step M06), then the muscle response is checked to determine if the contraction is strong enough to yield a therapeutic effect. If the strength of the contraction is less than necessary for the application, then the stimulation amplitude is increased (step M08). At this point, if the stimulation amplitude has reached its maximum, then the pattern of both electrodes is re-adjusted (step M05). If the stimulation amplitude is still below the maximum allowed (step M07), then a check is performed to determine if the patient has requested to stop the therapy. If there is a request to halt the session (step M09), the system reverts to the Idle state (step M00). If the patient has not requested to end the session, then the algorithm continues to deliver stimulation (step M03).

The above-described algorithm relies on the automatic detection of a pain marker or multiple pain markers by the device. Various options for detecting pain are available, such the use of sensors for detecting an increase in sympathetic activity, which correlates with pain onset and severity. Measures of sympathetic activity include heart rate variability, elevation in heart rate which may be detected via ECG (electrocardiogram), and elevation in respiratory rate. Respiratory rate may be measured via ECG, with a skin patch accelerometer, electrical impedance of the chest wall, microphone, or other techniques known in the art of respiratory monitoring. Other measures of sympathetic activity include muscle sympathetic nerve activity or sympathetic nerve activity. Such sympathetic nerve activity may be measured via needle microneurography, or more preferably via non-invasive measurement of sympathetic nerve activity using surface electrodes. Sympathetic activity is also known to influence sweat gland activity, which could be measured via fluctuation in skin conductance via a skin patch. Increased sympathetic activity also may lead to pilo-erection (hair standing on end) which leads to "goose bumps" on the skin surface. Goose bumps may be detected via skin impedance. Electrical impedance also increases between a simulating electrode skin patch and the skin surface with the development of goose bumps. Other markers that correlate with sympathetic activity include blood pressure, mean arterial pressure, blood vessel tone, blood vessel stiffness, capillary vasoconstriction (e.g. detected as tissue pallor of the distal fingers or toes, or via skin perfusion sensor), and carotid-femoral pulse wave velocity.

Additionally, other parameters could be measured to provide detection of pain, including monitoring facial expression via a facial EMG electrodes or a video screen (e.g., smart-phone, I-phone, tablet, I-pad, laptop, webcam, etc.). Onset of a grimace or frown or teeth clenching could serve as a marker for pain. Noxious stimuli also may cause dilation of pupils, which is detectable via photographic or video imagery. Electroencephalography also may be used to detect pain, as the EEG power spectrum increases with pain, and certain bandwidths may be particularly sensitive to pain including the delta, theta, and alpha bandwidths.

Figure 15:
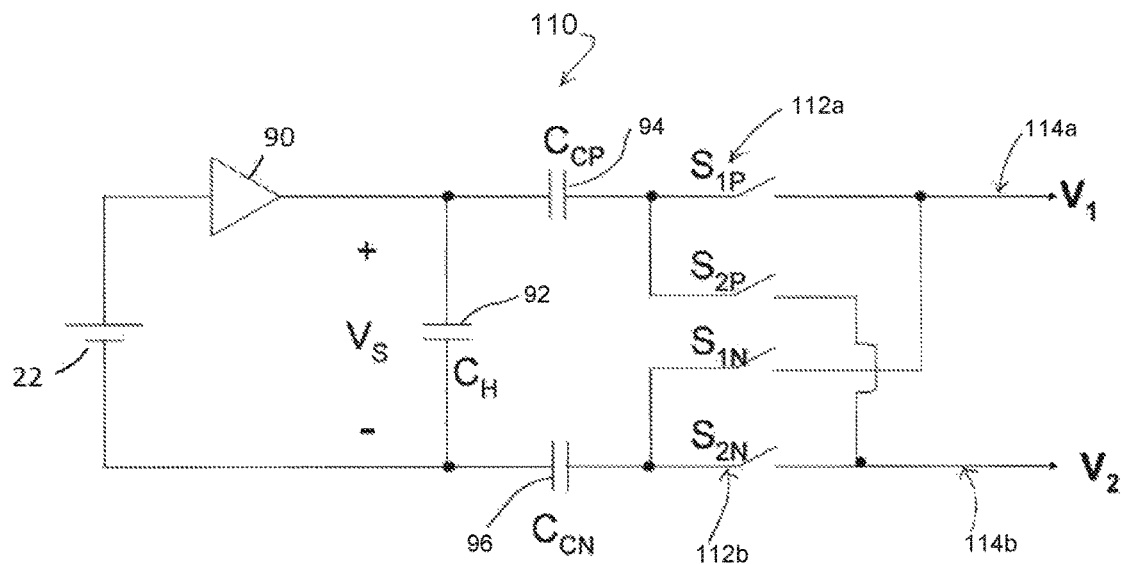
FIG. 15 is a simplified circuit diagram of an electrical stimulation unit of a muscle contraction stimulation system constructed in accordance with one aspect of the present invention.
Figure 16A:
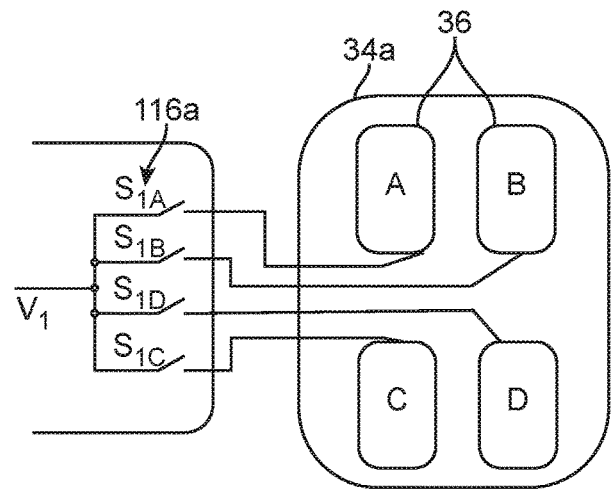
FIGS. 16A and 16B are, respectively, simplified circuit diagrams of a first stage (FIG. 16A) and a second stage (FIG. 16B) of electrode sets and their associated switches suitable for use in a muscle contraction stimulation system of the present invention.
Figure 16B:
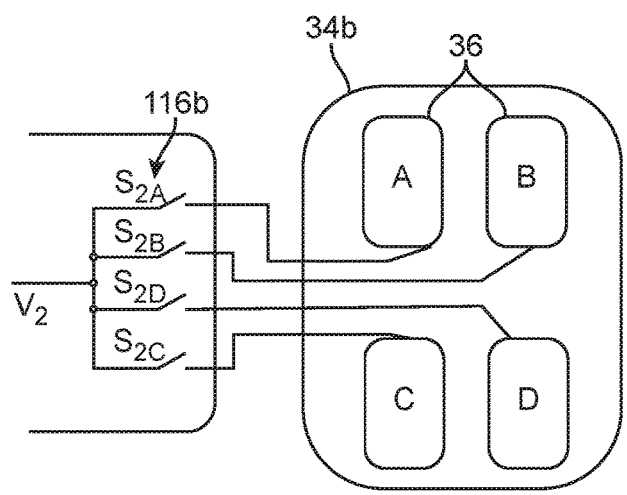

Referring now to FIG. 15, a simplified circuit diagram for an embodiment of the electrical stimulation unit 32 is described. As described for the layout of FIG. 9, electrical stimulation unit 32 includes holding capacitor 92, coupling capacitors 94, 96, and set of switches 112a, 112b, all of which provide two currents 114a, 114b to the electrode sets. FIGS. 16A and 16B depict two final sets of switches 116a, through which voltage passes before arriving at electrodes 36 of electrode sets 34a, 34b. Switches 116a are used for controlling which subset of electrodes 36 will actively participate in the stimulation.

Figure 17:
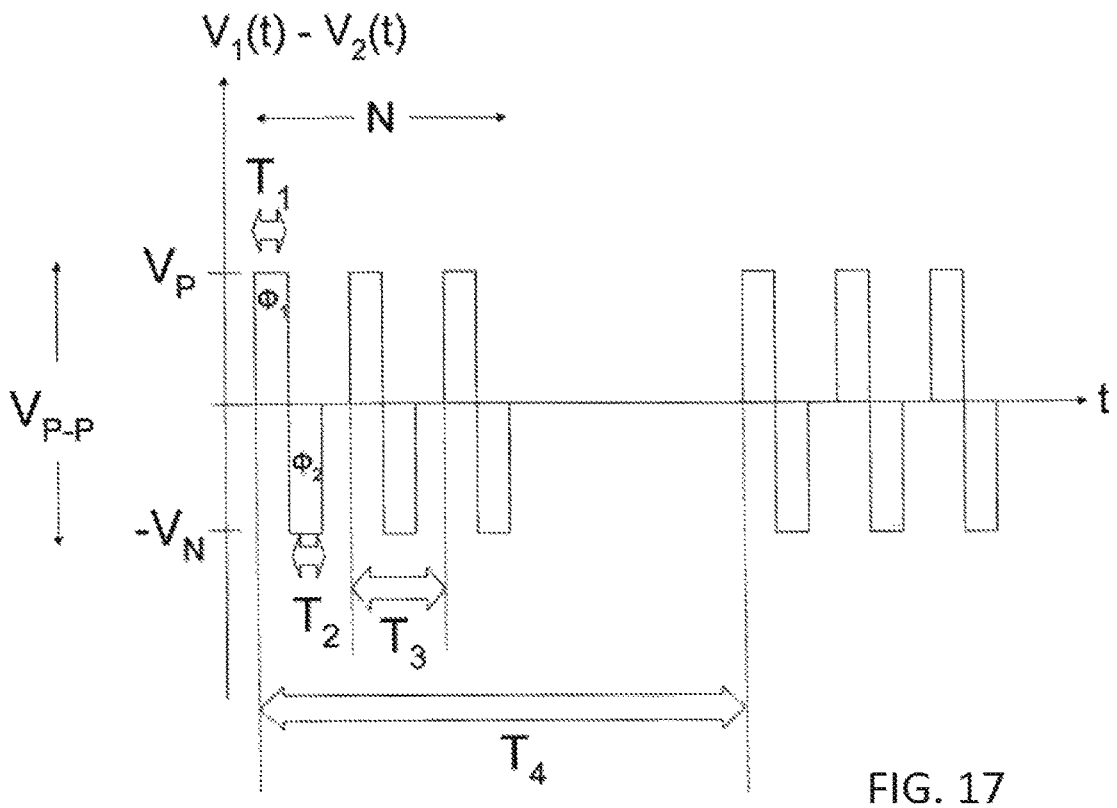
FIG. 17 is a graph, illustrating the details of an electrical stimulation waveform suitable for use with the muscle stimulation system of the present invention.
Figure 18:
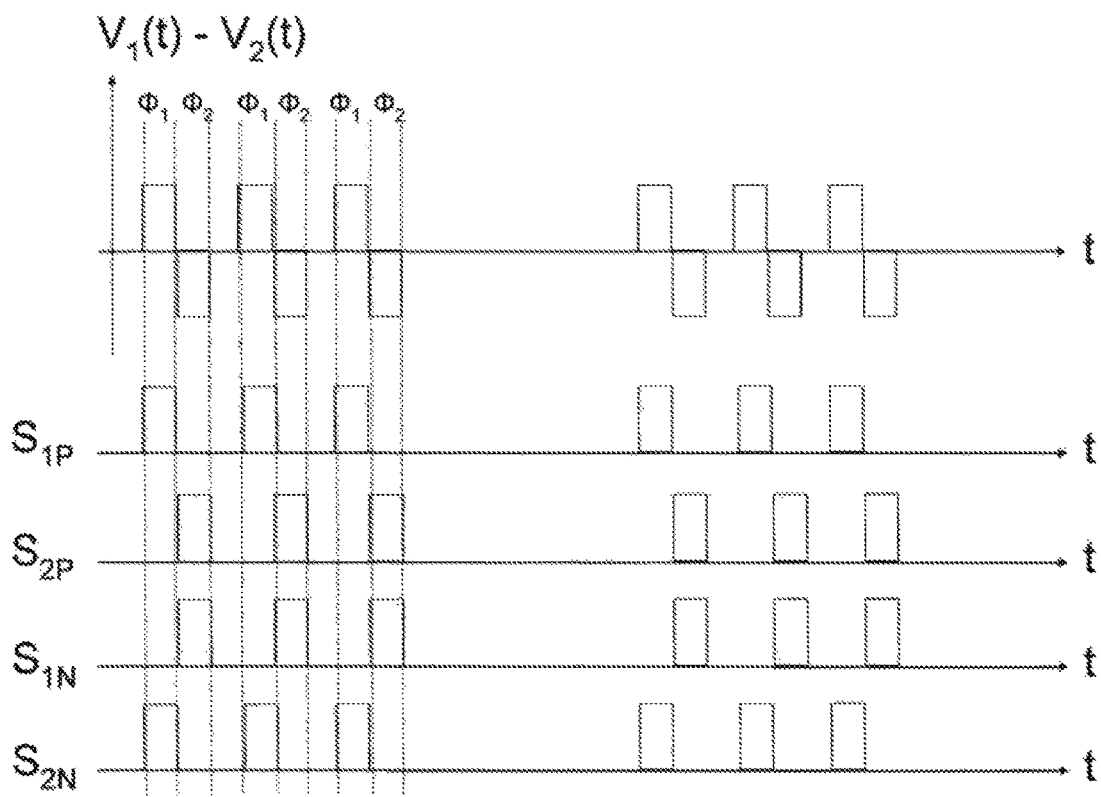
FIG. 18 is a graph, illustrating timing signals for the electrical stimulation therapy.
Figure 19:
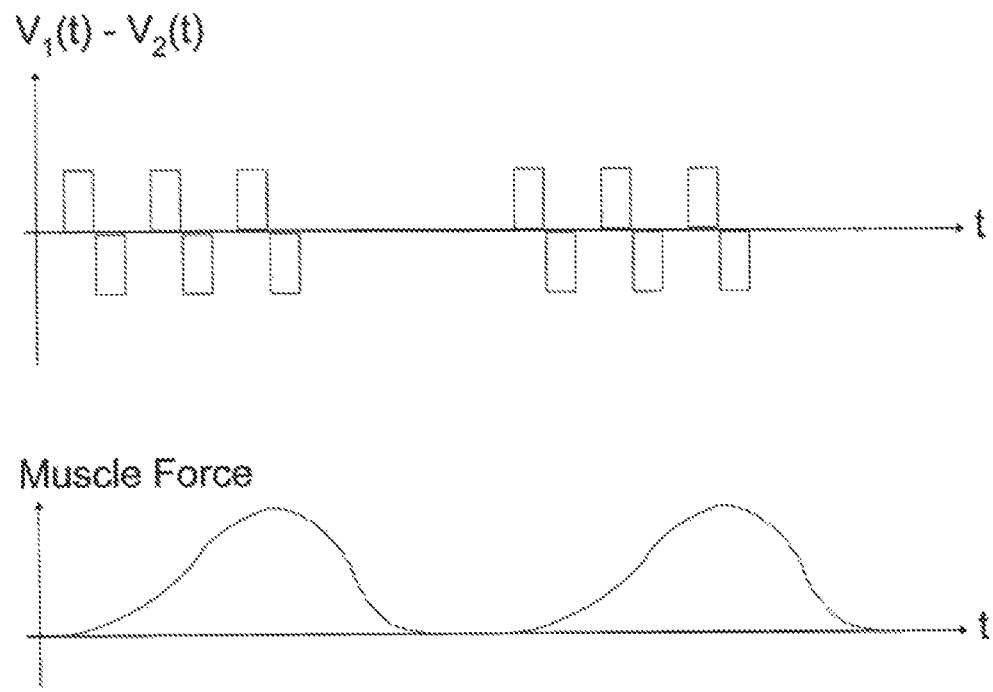
FIG. 19 is a graph, illustrating muscle force resulting from the application of electrical stimulation shown in the upper portion of the figure.

FIG. 17 depicts a pattern of stimulation provided by system 10 via electrical stimulation unit 32 to generate a desired muscle contraction waveform. FIG. 18 depicts a pattern of signals provided to electrodes 36 of system via switches 112a, 112b, in order to achieve the desired waveform. FIG. 19 illustrates the desired waveform.

In FIG. 17, $V_P$ is the amplitude of the first pulse ($\Phi1$), sometimes called the anodic pulse, while $V_N$ is the amplitude of second pulse ($\Phi2$), sometimes called the cathodic pulse. Usually, but not always, the amplitudes of the anodic and the cathodic pulses are chosen to be equal, although their polarities are opposite of each other. $V_{P-P}$ is the peak to peak amplitude of the resulting waveform. The waveform generated by system 10 may be in the form of a train of pulses, as shown in FIG. 17, which may work well for stimulating contraction of the skeletal muscles. $T_1$ is the duration of the anodic pulse, $T_2$ is the duration of the cathodic pulse, $T_3$ is the total elapsed time between two subsequent anodic pulses, and $T_4$ is the total elapsed time between two subsequent pulse trains. N is the total number of pulses in the pulse train.

Referring still to FIGS. 15 and 17, the first task performed by system 10 is to produce the necessary stimulation voltage as determined by control unit 24. For example, if the desired stimulation voltage is 15 Volts, then it is generated from power supply 22, which may be 3 Volts, using voltage multiplier 90 (see FIG. 9). Voltage multiplier 90 may be a Villard cascade voltage multiplier, a Dickson charge pump or any other type of voltage multiplier. Resulting voltage, $V_S$, is stored on the holding capacitor $C_H$. During the application of the anodic pulse, $V_S$ will be the amplitude of the anodic pulse, that is $V_P$. Similarly, during the application of the cathodic pulse, $V_S$ will be the amplitude of the cathodic pulse, that is $V_N$. Coupling capacitors 94 and 96 assure that the stimulation delivered to the patient is charge balanced, and that there is no net charge is left on either electrode set over time.

In order to generate the anodic pulse, electronic switches $S_{1P}$ and $S_{2N}$ are closed, while keeping the electronic switches $S_{2P}$ and $S_{1N}$ open. To generate the cathodic pulse, electronic switches $S_{1N}$ and $S_{2P}$ are closed, while the electronic switches $S_{2N}$ and $S_{1P}$ open. During all other times, all four switches are kept open. This operation results in the formation of voltages $V_1$ and $V_2$, with the differential voltage $V_1$-$V_2$ as shown in FIG. 17. A timing diagram for the operation of the electronic switches $S_{1P}$, $S_{1N}$, $S_{2P}$, $S_{2N}$ are shown in FIG. 18.

Before the voltages $V_1$ and $V_2$ are applied to electrode sets 34a, 34b, they pass through a final set of electronic switches 116a, 116b, as illustrated in FIGS. 16A and 16B. If all switches 116a shown on FIG. 16A are closed ($S_{1A}$, $S_{1B}$, $S_{1C}$, $S_{1D}$), then all four electrodes 36 of electrode set 34a will be connected in parallel. Similarly, if all switches 116b shown on FIG. 16B are closed, that is ($S_{2A}$, $S_{2B}$, $S_{2C}$, $S_{2D}$), then all four electrodes 36 of electrode set 34b will be connected in parallel. The resulting current in the tissue would resemble the one that is shown in FIG. 12A. However, if electronic switches $S_{1B}$ and $S_{2B}$ are opened, while keeping all other switches 116a, 116b closed, then the "B" electrodes 36 would be removed from both electrode sets 34a, 34b, and the resulting current in the tissue would resemble the one shown in FIG. 12B. Again, although this example and the accompanying drawing figures illustrate an embodiment with four electrodes 36 per electrode set 34a, 34b, any other suitable number of electrodes may be used in each set 34a, 34b. Additionally, each electrode set 34a, 34b may have more or fewer than four electrodes 36 and/or different numbers of electrodes 36 may be turned on or off in the sets. In addition, the electrode numbers and configurations need not be symmetrical between the two sets 34a, 34b.

Figure 20:
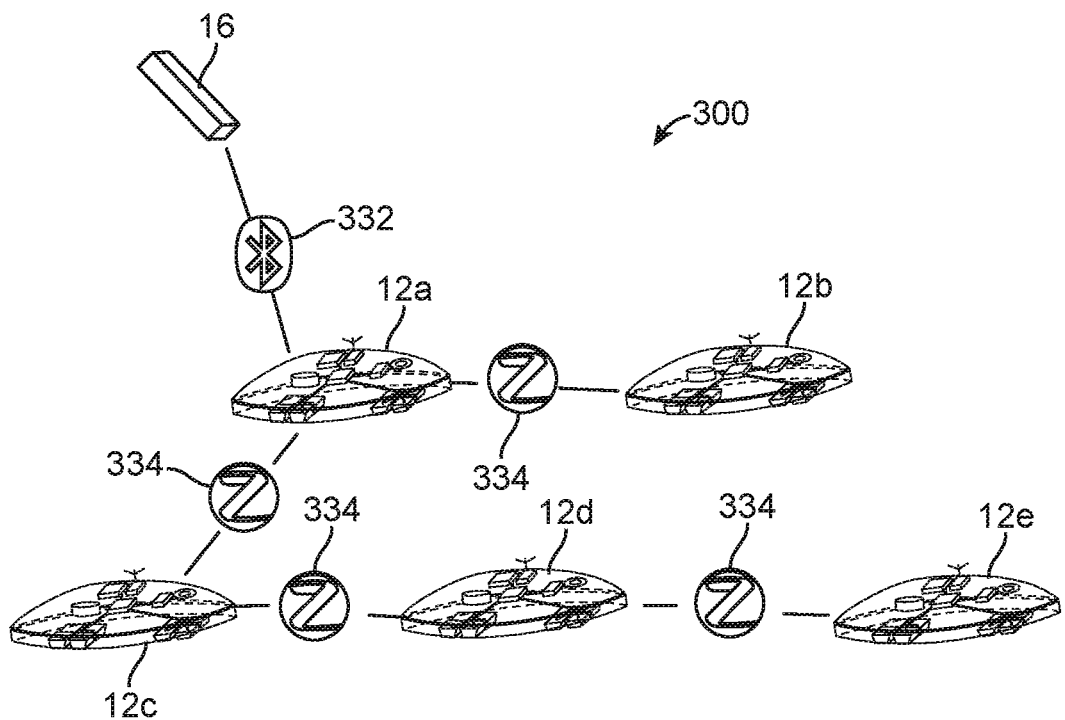
FIG. 20 is a diagram illustrating wireless connectivity configuration between a patient user interface and multiple muscle contraction stimulation patches.

With respect to FIG. 20, another exemplary muscle contraction stimulation system 300 is described, in which multiple skin patches 12a-12e are used and are connected to one another via a multimodal wireless network. Skin patches 12a-12e may be coupled together wirelessly via Zigbee connections 334 or other wireless protocol. One or more of patches 12a-12e may communicate via Bluetooth link 332 or other wireless protocol with patient interface unit 16. In the illustrated multimodal wireless network, all of skin patches 12a-12e are connected to each other using a ZigBee network 334. In addition, skin patch 12a serves as a ZigBee hub and echoes all the communications to patient interface unit 16 using Bluetooth link 332. In order to best communicate with patient interface unit 16, one of skin patches 12a preferably assumes the role of the ZigBee hub and communicates with patient interface unit 16, such as a smart phone. ZigBee networks 334 have the advantage of being able to self-form and self-repair, in case one of skin patches 12a-12e is removed from the network.

Furthermore, ZigBee systems use low power and are suitable for low data rate applications. Each skin patch 12a-12e may report the timing of the relevant events, such as the arrival of blood pressure pulse at the muscle and cardiac contraction from the ECG, which are all relayed to patient interface unit 16 via the Bluetooth link 332 between ZigBee hub 12a and patient interface unit 16. Patient interface unit 16, in turn, calculates the necessary timing of the stimulation to be delivered to the muscles and communicates those values to ZigBee hub 12a via Bluetooth link 332. The ZigBee hub distributes the parameters back to the remaining units via the ZigBee network 334. Additional communications transceivers may be utilized to build a live link with implantable medical devices, such as pacemakers, defibrillators, and CRT/CRT-D devices to coordinate with the timing of stimulation with cardiac activity. Furthermore, the patient interface unit may communicate with external medical devices, such as wearable heart rate monitors, glucose sensors or insulin pumps, as well as other stations on the internet, such as electronic medical records (EMR) and databases.

Therapeutic Applications of the Invention

The LAMES system of the present invention is expected to find wide applicability in making self-administered muscle contraction therapy simpler, safer and with improved clinical outcomes. Several examples are provided below of possible clinical applications for embodiments of muscle contraction stimulation system 10. The following examples are provided for purposes of illustration only and are not intended to limit the scope of the invention as described by the claims. Further, while description of several disorders that may be treated using systems, devices and methods of the present application are disclosed, these examples are not intended to be an exhaustive description of all possible applications. Many other disease states and disorders may be treated using the systems, devices and methods described herein.

A. Treatment of Metabolic Disorders

It is contemplated the systems of the present invention may be advantageously used by large patient populations afflicted with metabolic disorders, either to supplement an existing exercise program or to provide muscle stimulation in patients not otherwise capable of routine or strenuous exercise. A non-limiting list of possible metabolic disorders for which the system, devices and methods of the present invention of the present invention may provide treatment include:

1. Insulin resistance. Insulin resistance affects millions of people worldwide. As a person becomes more obese, he or she becomes progressively more insulin resistant, leading to impaired glucose tolerance, often resulting in Type 2 diabetes. As the disease progresses, individuals may develop complications, such as retinopathy, nephropathy, neuropathy, vasculopathy, heart disease and stroke. Exercise helps these individuals because acute muscle contractions are a potent stimulus of skeletal muscle glucose uptake, and chronic exercise stimulates pancreatic insulin secretion. Therapeutic regimens of muscle contraction therapy using muscle contraction stimulation system 10 may improve body weight, HbA1c (a marker of long-term glycemic control), and overall health of Type 2 diabetes patients.

2. Fatty Liver Disease. Non-alcoholic fatty liver disease (NAFLD) is an acquired metabolic liver disorder that affects 20-30% of the population in North America. NAFLD refers to a spectrum of liver disorders, ranging from simple fatty liver, to non-alcoholic steatohepatitis (NASH), characterized by an inflammatory reaction with liver cell injury. Between 5-20% of patients with fatty liver will develop NASH; in 10-20% this develops into fibrosis; in <5% this progresses to cirrhosis. Weight reduction plays an important role in reversing NAFLD, and so lifestyle changes such as exercise and diet control are the recommended interventions for these individuals. Therapeutic regimens of muscle contraction therapy using muscle contraction stimulation system 10, for example directed to any combination of the buttocks, quadriceps, hamstrings, or calf muscles, may improve hepatic steatosis and reduce insulin resistance and serum IL-6 levels in NAFLD patients who are resistant to lifestyle counseling or unable to exercise.

3. Obesity. Obesity has serious physical, psychological, and economic implications for patients, and presents a challenge to the healthcare system of many countries. Approximately 35% of adults in the U.S. are obese. Interventions to facilitate weight loss start with behavioral changes, including counseling, nutritional counseling, and exercise. For reasons related to lack of motivation, lack of time, or comorbidities, many obese individuals are unable to maintain a long-term exercise program. Given the muscle mass of the buttocks and leg muscles, chronic daily sessions muscle contraction therapy using muscle contraction stimulation system 10 are expected to increase metabolism of adipose tissue, reduce weight and help treat obesity in overweight patients.

B. Treatment of Skeletal Muscle Dysfunction

1. Osteoarthritis. The knee is the joint most commonly affected by osteoarthritis (OA). The prevalence of OA is expected to increase in the future, due to the aging population and increasing rate of obesity. Patients with knee OA have decreased strength of the knee extensor muscles, as well as decreased muscle thickness and fascicle length. Therapeutic regimens of muscle contraction therapy using muscle contraction stimulation system 10 may reduce knee pain and improve muscle mass and function in patients with knee OA. Muscle contraction therapy using system 10 also may reduce hip pain and improve muscle mass and function in patients with hip OA.

2. Sarcopenia. Aging is associated with progressive loss of skeletal muscle mass. This loss of muscle mass reduces strength and impairs functional capacity. Rapid muscle loss is a common problem in the elderly following limb immobilization or bed rest to due injury or illness. Maintaining some level of physical activity during a period of disuse is required to attenuate muscle atrophy. Therefore, regular, ongoing regimens of muscle contraction therapy using muscle contraction stimulation system 10 may attenuate the loss of muscle mass and/or strength in elderly patients, ICU patients, and patients recovering from surgery.

3. Neuromuscular Training. NMES is a standard tool of physical therapy, for example, to improve limb weakness after stroke, head trauma, or surgery. Physical therapists may use muscle contraction stimulation system 10 to treat muscle atrophy, increase muscle mass, improve muscle strength, and increase muscle endurance. System 10 also may be used to increase neural drive to the muscle, improve proprioception, improve motor control, and facilitate or re-educate voluntary motor function.

C. Treatment to Improve Aerobic Fitness

1. Aerobic exercise. Aerobic exercise is a key component for maintaining health and improving heart function in patients with chronic disease, such as COPD or coronary artery disease. If individuals are unable to perform aerobic exercise due to injury or illness, system 10 may be used as an alternative to exercise to avoid or reverse aerobic deconditioning. In fact, muscle contraction stimulation system 10 may be used to induce oxygen uptake (VO2), increase heart rate, and increase blood lactate—all changes that are similar to those resulting from aerobic exercise.

2. Cancer. Exercise may improve survival in patients with cancer for a variety reasons. Patients in better physical condition are more likely to receive second and third line treatments, and are better able to tolerate and complete a course of chemotherapy. Also, exercise may potentiate the effects of cytotoxic chemotherapy through influences on drug distribution, pharmacodynamics, and metabolism. Improvements in lean body mass and physical functioning also may have implications for disease risk and survival. System 10 advantageously may be used in cancer patients to improve function, and possibly survival.

D. Treatment of Circulatory Disorders

Heart Failure. Counter-pulsation is a method of circulatory assistance to reduce cardiac workload. An intra-aortic balloon pump ("IABP") provides this benefit, but because placement of an IABP requires an invasive implant, it is reserved for decompensated patients in the ICU. Noninvasive, external counter-pulsation systems are known that encase a patient's legs in pneumatic cuffs that provide sequential inflation (distal to proximal) during diastole of the cardiac cycle. External counter-pulsation is FDA approved for treatment of heart failure, unstable angina, acute myocardial infarction, and cardiogenic shock, and it is performed at a hospital or doctor's office. It includes a large table, hydraulic system, and computer interface. Therapeutic regimens of muscle contraction therapy using muscle contraction stimulation system 10 may provide benefits that are similar to those of external counter-pulsation.

E. Treatment of Peripheral Vascular Disease

1. Chronic Venous Insufficiency (CVI). CVI occurs when the venous valves in the leg veins are not working effectively, making it difficult for blood to return to the heart. Valve damage may occur as a result of aging, prolonged sitting or standing, or reduced mobility leading to deep vein thrombosis (DVT). Valve incompetence leads to venous hypertension, which underlies most of the symptoms of CVI. Patients may develop swollen legs, leg pain, skin weeping, and ulceration. Therapeutic regimens of muscle contraction therapy using muscle contraction stimulation system 10 may improve hemodynamic parameters, reduce leg edema, and improve blood supply to the skin of the foot.

2. Prevention of deep vein thrombosis (DVT). During prolonged immobilization, individuals are at risk of developing a DVT, which is potentially life threatening if it travels to the lungs (pulmonary embolus). To prevent venous stasis, patients who are immobilized may have a sequential compression device (SCD) placed around the legs, which is cyclically inflated with air to direct venous blood from the legs to the trunk. Therapeutic regimens of muscle contraction therapy using muscle contraction stimulation system 10, especially of the calf muscles, may be used to improve blood flow from the legs during bed rest and thus prevent DVT.

3. Peripheral artery disease (PAD). Over eight million Americans and over 200 million people worldwide suffer from PAD, marked by diseased or blocked or partially blocked arteries in the legs. This number is likely to rise as the population ages. The classic symptom is claudication, that is, discomfort on exertion in muscle groups distal to the affected artery. First-line therapy is supervised walking up to the point of pain, then resting until the pain subsides, then walking again, repeating the sequence for 20 to 60 minutes per session at least 3 times per week. This exercise causes collateral blood vessels to from in the legs that can compensate for obstructed arteries. The average age at which people develop PAD is 70. A number of these patients suffer from confounding illnesses such as COPD, heart failure, arthritis, or other disorders that make it difficult to participate in a walking exercise program. Moreover, the claudication discomfort may dissuade them from maintaining a chronic exercise program. Therapeutic regimens of muscle contraction therapy using muscle contraction stimulation system 10 may be used in these PAD patients as a substitute for exercise.

4. Lymphedema. The lymphatic system circulates lymph fluid via lymphatic vessels, which drain into lymph nodes. Removal, damage, or blockage of lymph vessels or lymph nodes from surgery, radiation, cancer, or infection can interfere with lymph return from the limbs resulting in limb swelling. System 10 may be used with one or more limbs to help return lymph from the limbs to the trunk, thereby reducing limb swelling.

F. Improvement of Sympathetic Drive

Hypertension. Mechanically-sensitive stretch receptors are located in the heart, great veins, aorta, and blood vessels of the lungs. These stretch receptors sense changes in central blood volume and pressure. Increases in central volume (pressure) increase vagal afferent nerve firing, reflexively decreasing sympathetic nerve activity (SNA). This phenomenon is called the cardiopulmonary baroreflex. Increases in central blood volume associated with the muscle contraction activate the cardiopulmonary baroreceptors and inhibit SNA. Therapeutic regimens of muscle contraction therapy using muscle contraction stimulation system 10 may be used to reduce SNA to improve a variety of conditions related to increases in SNA, including hypertension.

As mentioned above, the muscle contraction stimulation system and methods of the present invention may be used to treat any of a number of medical conditions, to enhance physical therapy, to act as a substitute for physical exercise and/or for any other suitable therapy to benefit a given human or animal subject. What follows are three exemplary therapeutic examples using system 10.

Example 1: Muscle Contraction Stimulation for Treatment of Heart Failure

Referring now to FIGS. 21 to 24, an exemplary configuration of muscle contraction stimulation system 400 and method suitable for treating heart failure are described. Heart failure is a condition in which the cardiac muscle is unable to pump a sufficient amount of blood to meet the physiological needs of the body. It is a progressive disease with no known cure, affecting more than 5 million individuals in the United States. The average expected survival time for heart failure patients is approximately five years from the time of diagnosis. Traditional treatments aim to improve heart function by reducing afterload (e.g. reducing the arterial pressures) and increasing contractility of the cardiac muscle. In spite of such treatments, heart failure patients eventually succumb to this disease.

Muscle contraction stimulation system 400 may be configured and used for treatment of heart failure patients by stimulating contractions in muscles of the lower extremities to help pump blood back to the heart. This allows the heart to acutely "rest." With chronic use, it is possible that the muscle contraction stimulation system may allow the heart to remodel, thereby reducing end diastolic volume and improving left ventricular ejection fraction. In one embodiment, skin patches 412a-412d may be placed over the calf muscles (patch 412a), hamstring muscles (patch 412b), gluteus muscles (patch 412c) and quadriceps muscles (patch 412d). Electrical stimulation may be applied to these muscle groups sequentially by system 400, starting with the calf muscles and moving up the extremities toward the head, thus causing the muscles to squeeze blood upward toward the heart. The timing diagram in FIG. 21B illustrates ECG signal 422 of the patient, along with stimulation pulses 420 provided by system 400 to the patient's nerve tissue, to show the approximate timing of stimulation of the skin patches 412a-412d. The electrical stimulation that is applied to the calf muscles is labeled "A" and comes soon after the T-wave of the ECG. Next, the hamstrings and the quadriceps are stimulated, which is labeled "B." Finally, the gluteus muscles are stimulated, which is labeled "C."

Muscle contraction system 400 may use a variety of frequencies including non-tetanic frequencies (4-12 Hz) that produce muscle twitches, and tetanic frequencies (20-100 Hz) that produce fused contractions. For applications where the objective is to facilitate circulation of fluid from the legs (e.g. heart failure, chronic venous insufficiency, prevention of deep vein thrombosis, and peripheral artery disease), it is expected to be preferably to use tetanic frequencies of 20-75 Hz.

Referring to FIG. 22, for the treatment of heart failure with electrical stimulation of leg muscles to be safe and efficacious, it is important that application of the electrical stimulation to the muscles be determined and applied correctly. For example, if the skeletal muscle stimulation causes the muscles to contract just after ventricular systole, such stimulation would increase cardiac afterload and undesirably increase workload on the heart; such stimulation timing also might cause mitral valve regurgitation. The task of determining the optimal timing of the skeletal muscle stimulation is further complicated by the patient-to-patient variations, its dependence to the heart rate and the patient position.

System 400, as described above, may use one or more sensors 15 in skin patch 12, separate sensor(s) 14 and signal processing unit 28 to determine the correct timing of skeletal muscle stimulation relative to the cardiac cycle. For example, an ECG device, blood pressure measurement device and/or accelerometer(s) may be used to monitor the patient's ECG signal 422 and local ballistocardiogram signal 424. The ECG signal 422 may be used as the reference for the generation of the timing of all subsequent events, such as the stimulation pulses A, B and C in FIG. 21B. In the beginning, the delay between the QRS or the T-wave and the peak of the local ballistocardiogram 424 may be measured, while the patient is at rest and no stimulation is being applied to the leg muscles (T10 on FIG. 22). The peak of the local ballistocardiogram 424 indicates that the systolic pressure wave has arrived at the local position, for example at the upper thigh. The stimulation of the muscle should start only a period after this peak, T11, but not later than T12, as shown in FIG. 22. Skeletal muscle may be safely stimulated within the time interval of T11 to T12.

An exact time to stimulate within the time interval T11 to T12 may be determined using additional information from sensors 14 and 15. Once the therapy becomes effective, both the heart rate and the arterial pressure will decrease. Hence, control unit 24 may sweep the time that the electrical stimulation is applied within the time interval of T11 to T12, while monitoring the blood pressure or the heart rate. Afterwards, the delay that produces the maximum drop in the heart rate or blood pressure may be chosen as the preferred delay to stimulate the skeletal muscles.

In a preferred embodiment, skeletal muscle stimulation may be timed to occur at the beginning of diastole and stop at the beginning of systole to provide counter-pulsation support. This stimulation regime is expected to augment diastolic pressure, decrease left ventricular afterload, and increase venous return. Augmenting diastolic pressure displaces a volume of blood backward into the coronary arteries during diastole, when the heart is in a state of relaxation and the resistance in the coronary arteries is at a minimum. The resulting increase in coronary artery perfusion pressure may increase blood flow through collateral blood vessels, or enhance development of coronary collateral blood vessels. In addition, when the left ventricle contracts, it works against reduced afterload, as the counter-pulsation will contribute to emptying blood volume from the aorta. Clinical applications for this embodiment would include angina, heart failure, ischemic stroke, erectile dysfunction, and acute myocardial infarction.

In another embodiment, skeletal muscle stimulation may be timed to occur during systole and end during diastole of the same or a subsequent cardiac cycle, so as to direct blood flow to the head and organs of the truck. Such a stimulation regime is expected to be beneficial for patients who require an increase in their intravascular fluid volume, including conditions such as inferior wall myocardial infarction, hemorrhage, dehydration, sepsis.

Figure 23A:
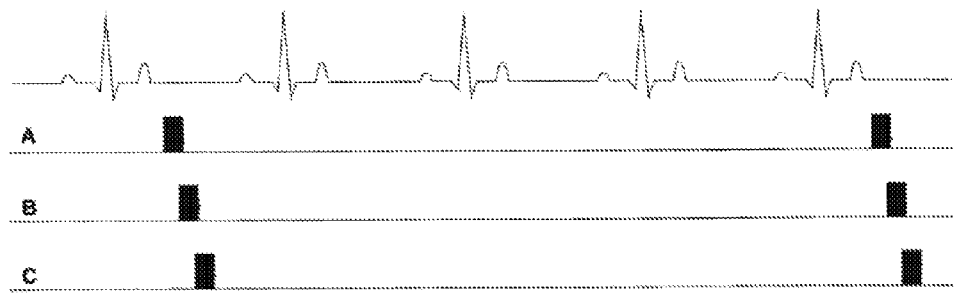
FIGS. 23A-23D are ECG tracings and muscle contraction stimulation therapy timings for a program of contraction stimulations that is adjusted over time to the physiological needs of the patient.
Figure 23B:
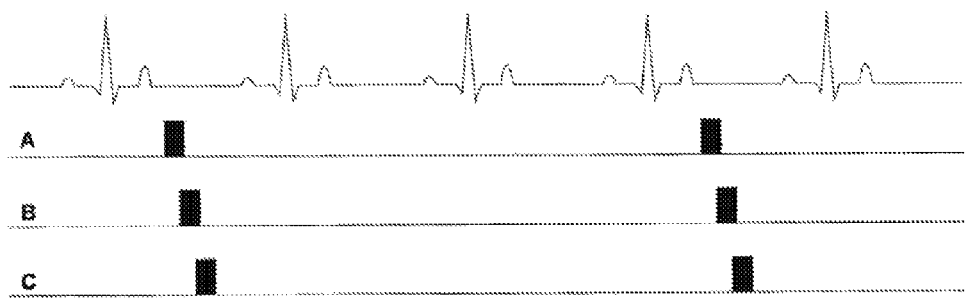
Figure 23C:
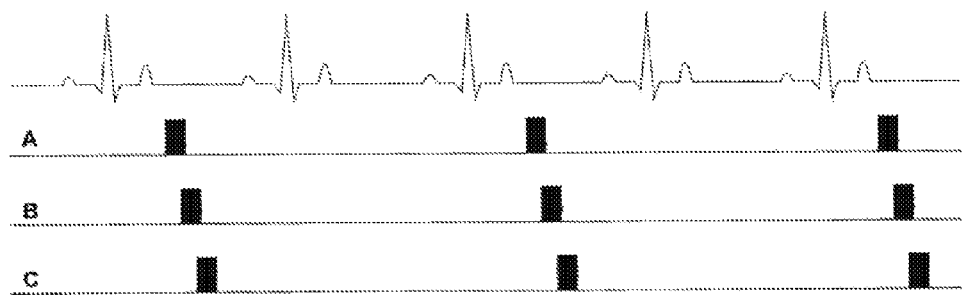
Figure 23D:
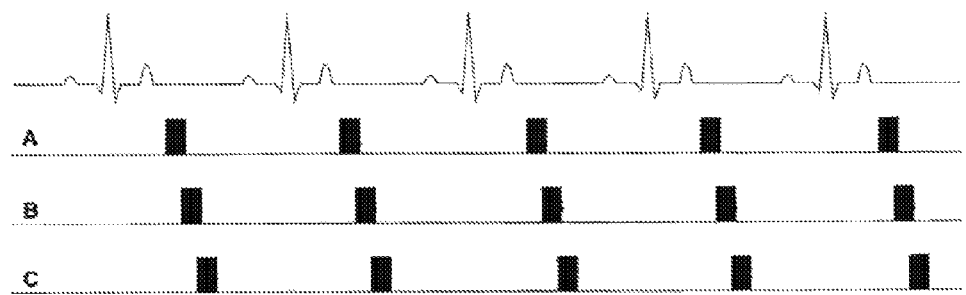

Referring now to FIGS. 23A to 23D and 24, control unit 24 also may determine the rate at which the skeletal muscles of the lower extremity are stimulated. For example, a training regimen may be used over time on a patient, to help slowly condition the muscles. Such training may be very beneficial for heart failure patients, who typically are not accustomed to any exercise or who exercise only minimally. In one training regimen, illustrated in FIGS. 23A-23D, control unit 24 determines whether or not the stimulation should be applied during any given cardiac cycle. During an initial period of the therapy, illustrated in FIG. 23A, electrical stimulation is applied only during one of four consecutive cardiac cycles. Later, as the patient's muscles become conditioned, muscle contractions may be stimulated during one out of three consecutive cardiac cycles (FIG. 23B), then every other cardiac cycle (FIG. 23C), and finally once every cardiac cycle (FIG. 23D). The decision to accelerate the timing of stimulations may be made by control unit 24, based on programmed parameters, parameters entered by the physician, a decision made by the patient, a programmed treatment algorithm, and/or muscle fatigue sensed by one or more sensors 14, 15 of system 400.

Figure 24:
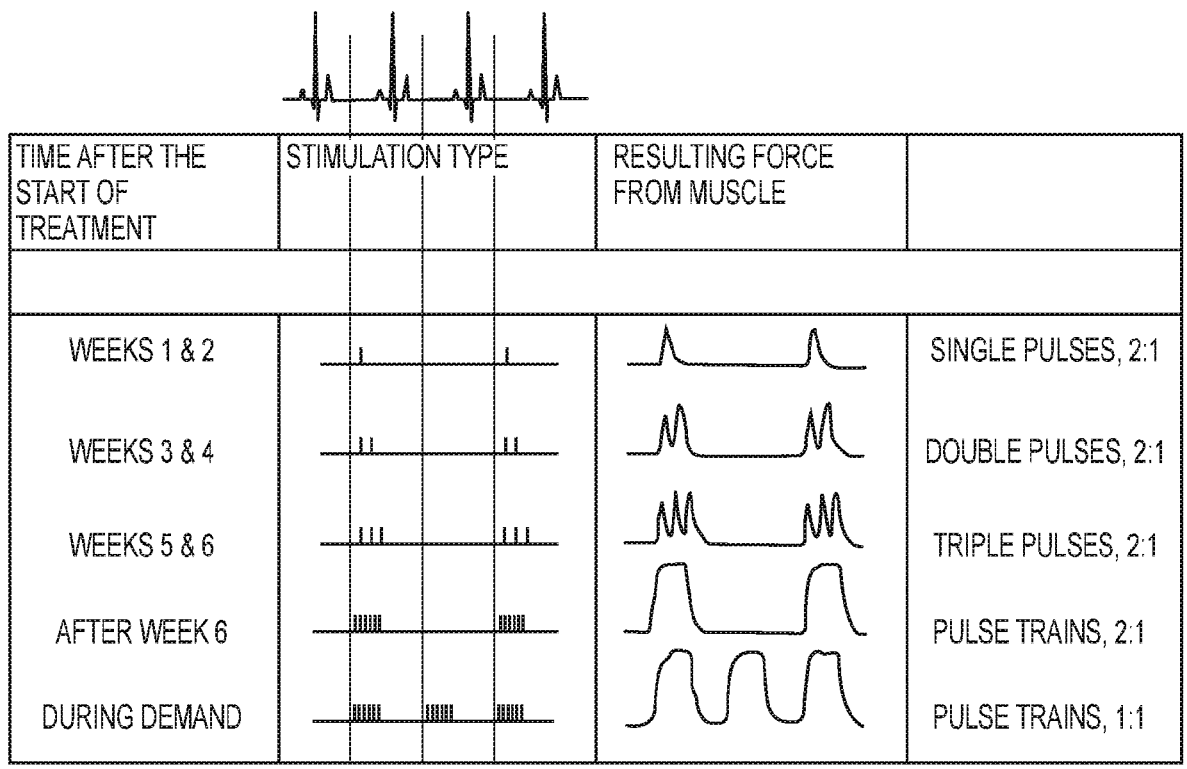
FIG. 24 is a chart illustrating a muscle contraction stimulation therapy timeline in accordance with the present invention.

FIG. 24 illustrates a second exemplary treatment regimen for heart failure patients. In this case, the electrical stimulation is applied to the skeletal muscles during every other cardiac cycle throughout the regimen—rows 1-4 of the table in FIG. 24—but the number of stimulation pulses per cardiac cycle increases over time. During the early periods of the training regimens, such as the first two weeks, only a single pulse is applied. This is illustrated in the first row of the table of FIG. 24 and would also be the equivalent of N=1 for the waveform shown in FIG. 17. As the skeletal muscle transforms and become less fatigue prone, the number of pulses (N) is increased, forming stronger and sustained contractions. Furthermore, when there is a strong demand for increased cardiac output, as indicated by a sudden increase in the heart rate, control unit 24 may switch to a stimulation pattern where the skeletal muscle is stimulated during each cardiac cycle, as depicted in the bottom row of FIG. 24.

Example 2: Treatment of Type II Diabetes

Insulin resistance refers to an impairment in insulin action in tissues, such as skeletal muscle, adipocytes and liver. In insulin resistant states, insulin stimulated glucose uptake into skeletal muscle is both reduced and delayed. Insulin resistance in skeletal muscle is associated with many disease states, including heart failure, dyslipidemia, chronic kidney failure, normal aging, obesity and Type 2 diabetes. Diabetes is a complex disease that affects millions of people worldwide. It is predicted that 1 in 3 adults in the US will have diabetes by 2050. Obesity plays a role in the majority of cases. As a person becomes more obese, they enter a more insulin resistant state, leading to impaired glucose tolerance, which can lead to the onset of Type 2 diabetes. As the disease progresses, the risk of complications increases. Complications include retinopathy, nephropathy, neuropathy, and vasculopathy, leading to heart disease and stroke.

Exercise is considered a first line treatment for individuals with Type 2 diabetes, because it increases the sensitivity of the glucose transport process to insulin in skeletal muscle. Muscle contraction during exercise is a more potent stimulus of skeletal muscle glucose uptake than insulin. Chronic regular exercise leads to an adaptive response of increased muscle mass that affects glucose metabolism. Chronic exercise also affects pancreatic insulin secretion stimulated by glucose. Exercise guidelines for Type 2 diabetes recommend regular, moderate-intensity, endurance type physical activity for 30-60 minutes per day on most days of the week. The motivation of patients to stick with an exercise program, however, is low. About 70% of the adult population fails to meet the recommended 30 minutes goal of regular exercise, and approximately 40% does not engage in any kind of physical activity. Individuals with Type 2 diabetes are typically overweight, and may suffer from arthritis, embarrassment, or lack of motivation to head outside or to the gym for exercise outdoors. They also may be elderly, or disabled.

Muscle contraction stimulation methods, devices and systems of the present invention may be used for treatment of Type 2 diabetes patient, by simulating exercise via stimulated muscle contractions. As discussed above, the muscle contraction system of the present invention may use a variety of frequencies. The use of non-tetanic frequencies (4-12 Hz) produces muscle twitches, while tetanic frequencies (20-100 Hz) produces fused contractions. Stimulating at 5 Hz will allow for complete relaxation between muscle twitches. Relaxation between muscle twitches is important to achieve maximal energy consumption as the shortening of muscle fibers (actin myosin cross bridge cycle) consumes more ATP than sustaining a shortened muscle length. Also, non-tetanic stimulation is less fatiguing than tetanic stimulation at comparable levels of oxygen consumption. To maximize metabolic effects and energy consumption in disorders such as Type 2 diabetes, fatty liver disease, and obesity, the muscle contraction system should maximize the stimulated muscle mass by including multiple large muscle groups at a frequency of 4-6 Hz, for long treatment sessions (greater than 60 minutes), and training frequency 5-7 times per week.

A further consideration is that there exist safety issues specific to treating Type 2 diabetes; the muscle contraction stimulation system of the present invention is uniquely configured to help manage those issues. For example, when the blood glucose concentration drops to a value that is below 70 mg/dL, a condition known as hypoglycemia results, typically also involving a marked increase in heart rate, a condition known as tachycardia. System 10 may be configured to monitor the heart rate of the subject using an ECG device, and if the heart rate rises above a certain value, that increase in heart rate may be interpreted as an indicator of hypoglycemia, which indicator then may be used terminate therapy. Increasing values of Homeostatic Model Assessment of Insulin Resistance (HOMA-IR) index is associated with significantly higher blood pressure levels and reduced R-R interval, stroke index, cardiac index, pre-ejection period and left ventricular ejection time across different categories of body mass index and blood pressure. Hence, the therapy session may be ended when a reduction in blood pressure or an increase in the R-R interval, stroke index, cardiac index, pre-ejection period or left ventricular ejection time is detected.

Another feedback mechanism that is available to monitor safe operation is the use of the capacitive component of the skin impedance to provide a measure of the changes in the blood glucose concentration. Again, any significant drop in the skin capacitance, measured in the frequency range of 20 KHz to 100 KHz, may be interpreted as indicative of the onset of hypoglycemia and the need to terminate the therapy. This type of measurement is best conducted using interdigitated electrodes that are located over a superficial vessel, such as the cephalic vein. A baseline capacitance value of 35 pico-Farad (pF) generally can be expected. During the treatment period, blood glucose level is expected to decrease for a patient with type II diabetes. Typically, a blood glucose level decrease of 2 mmol/Liter is indicated by a drop of the capacitance by 3.5 pF. Accordingly, in one embodiment, the system is configured to monitor the changes in the capacitance value and interpret a reduction in the skin capacitance as a reduction in blood glucose level. When the value of the capacitance is reduced by a desired amount, e.g. 3.5 pF, then it may be assumed that the blood glucose level has lowered by 2 mmol/Liter and the therapy session may be ended.

In another embodiment, the control unit may be configured to terminate the stimulation that is delivered to a muscle group that is fatigued, but at the same time communicate this information to the patient interface unit. If there is remaining time in the planned therapy duration or the therapy goal has not yet been achieved, then the stimulation of another group of muscles may be initiated. This transition between stimulated muscle groups may be accomplished in any one of several ways: If the patch is located so that it covers both the fatigued muscle group and the new muscle group, then the electrodes in the patch may be electrically reconfigured to capture the new muscle group instead of the previous one. Alternatively, the patient interface unit may instruct the patient to reposition the skin patch to a location that is closer to the new muscle group and the new threshold determination process is started, as discussed above. Finally, the patient may initially place multiple skin patches at the beginning of the training session, so that the patient interface unit can automatically switch from one muscle group to the next when a fatigue condition is detected in the first muscle group. This particular embodiment of the invention utilizes the fatigue sensor as described before.

In the case where a patient also has a cardiac stimulator, such as pacemaker, ICD, CRT, CRT-D or subcutaneous ICD, changes in the pacing threshold may be used as a detector of blood glucose levels. In this case, patient interface unit 16 may communicate with the cardiac stimulator, obtain pacing threshold information, and interpret any increase in the capture threshold as a drop in the glucose levels.

The feedback systems incorporated in systems constructed in accordance with the principles of the present invention also enable medical professionals to determine if given therapy sessions have been effective or not. For example, if there are no changes in the heart rate, blood pressure or the capacitive component of the skin resistance throughout a given therapy session, then it is likely that blood glucose levels also did not significantly change, which in turn indicates that the insulin resistance was not significantly reduced. Based on this type of data reporting, the medical professional may choose to increase the number of muscles or muscle fascicles being stimulated, increase the prescribed therapy duration, or switch to a more intense stimulation regimen.

The feedback systems described above also allow for the optimal delivery of therapy that is specific to the treatment of a given disease state. For example, to reduce insulin resistance, it may be possible to use sub-maximal contractions of the skeletal muscle, which in turn would delay the onset of fatigue in the muscles, increasing the overall therapeutic benefit and reducing patient discomfort. However, for sub-maximal contractions to have therapeutic benefit, it may be necessary to periodically add a maximal contraction. All of this can be accomplished by the use of any of the sensors, such as the accelerometer or the MMG sensor with the aid of the signal processing unit, allowing the control unit to govern the entire therapy session. For example, the control unit may be programmed to increase the intensity of the stimulation that is applied while monitoring the strength of the muscle contraction. This can be done by measuring the RMS value of the MMG signal or its power at 50 Hz to determine the strength of the contraction. When increases in stimulation amplitude do not result in further increases in muscle contraction strength, the control unit may determine that the maximal contraction has been achieved. At this point the stimulation amplitude may be reduced to decrease the strength of the muscle contractions, which in turn would delay the fatigue onset. To assure optimal therapeutic benefit and to test the muscle fatigue status, the control unit periodically, e.g. every 15 minutes, increases the stimulation intensity to what is needed for maximal contraction, measures the strength of the contraction and subsequently decreases the stimulation intensity. The control unit may terminate the therapy when any of the following occurs: the pre-programed therapy duration is complete, muscle fatigue is detected, a safety concern is detected (as noted elsewhere in this application), the patient becomes ambulatory, or the patient enters a request for termination of the session.

Example 3: Muscle Contraction Stimulation for Treatment of Arthritis

Osteoarthritis (OA) of the knee is a progressive, age-related condition that may lead to pain, disability, and ultimately knee replacement surgery. It is a leading cause of chronic disability in people over the age of 50, leading to a cycle of increasing pain, weakness, and further pain. Knee OA bears more responsibility than any other disease for disability in walking, stair climbing, and housekeeping.

In addition to impacting skeletal structures, OA impacts the neuromuscular system. Patients often suffer from weakness of the quadriceps muscle, a knee extensor. Muscle weakness may be associated with a decrease in muscle mass and/or a reduction in neural drive to the quadriceps muscle. Quadriceps weakening has been related to decreases in proprioception, joint stability, and shock absorption, leading to further joint degeneration and subsequent pain.

Treatment of knee osteoarthritis aims to relieve pain and improve metrics of function such as strength, neuro-motor control, and joint range of motion. The first line therapy is exercise, or supervised physical therapy that aims to improve extensor muscle strength of the knee. However, pain and joint stiffness may make it difficult for patients to participate in traditional strength training and physical therapy programs. Pain can lead to under-dosing of strength training. Also, supervised exercise therapy is labor intensive, time consuming, expensive, and often logistically challenging for patients. Many patients with osteoarthritis are sedentary, unwilling, or unable to maintain a long-term physical therapy program.

Muscle contraction stimulation system 10 and method described herein may be used to treat OA in many patients. System 10 and method 40 may be used to increase strength, endurance, neural drive, activation time, proprioception, muscle architecture, muscle thickness, cross-sectional area, fascicle length, biomechanics, and strength of tendons, ligaments, fascia, connective tissue and soft tissues. Treatment with system 10 may increase muscle strength, promote faster walking and make it easier for individuals to perform activities of daily living, such as standing up from a seated position or climbing stairs without exacerbating knee pain.

Stronger knee extensor muscles are thought to decrease impact forces at the knee joint and might reduce the mechanical stimuli for pain.

The efficacy of exercise (and NMES) in treating OA is related to frequency, intensity, and program duration. Poor compliance, shorter treatment sessions, reduced number of repetitions, or suboptimal levels of muscle contraction will reduce the efficacy of an exercise program. System 10 and method 40 are configured to allow for longer treatment sessions, longer overall treatment program durations, and simpler and easier regimens for the patients to follow and adhere to. When used for OA therapy, system 10 may include one or more sensors 15, 14 that are specific to joint measurement, such as a goniometer, and in some embodiments system 10 may be used to determine a target joint flexion and/or extension before or during therapy. Stimulators 11, such as skin patches 12, may be placed on any or all the major muscle groups of the lower extremities. In some embodiments, it may be advantageous to stimulate antagonist muscles, such as the hamstrings, to balance quadriceps muscle contraction.

One embodiment of contraction stimulation system for OA would use tetanic frequencies of 20-75 Hz, with an on time of 4 to 10 seconds, and off time of 4-10 seconds. For hip OA, or for rehab after hip surgery, the gluteus muscle would be stimulated. For knee OA, or for rehab after knee surgery, the quadriceps, or both the quadriceps and hamstrings would be stimulated.

Figure 25A:
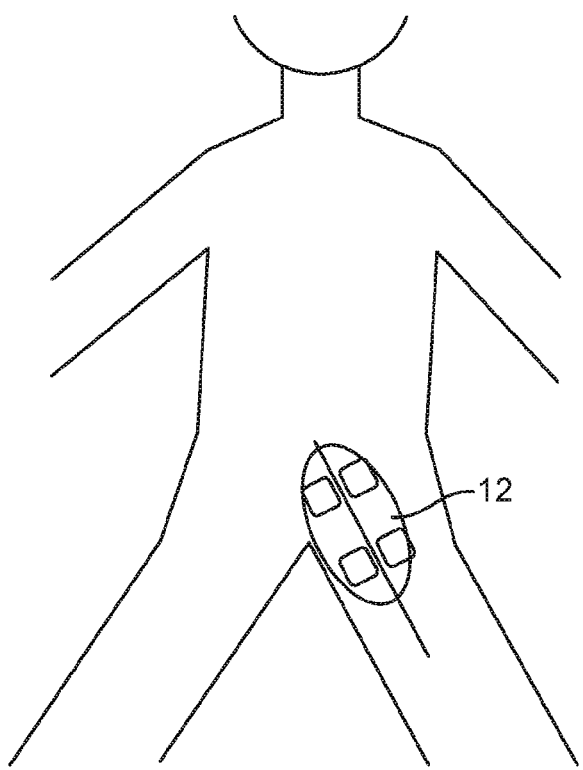
FIGS. 25A and 25B are respectively, a front view of a patient with muscle contraction stimulation patch placed to target the femoral nerve and a schematic diagram of the location of the skin patch in relation to the underlying anatomy.
Figure 25B:
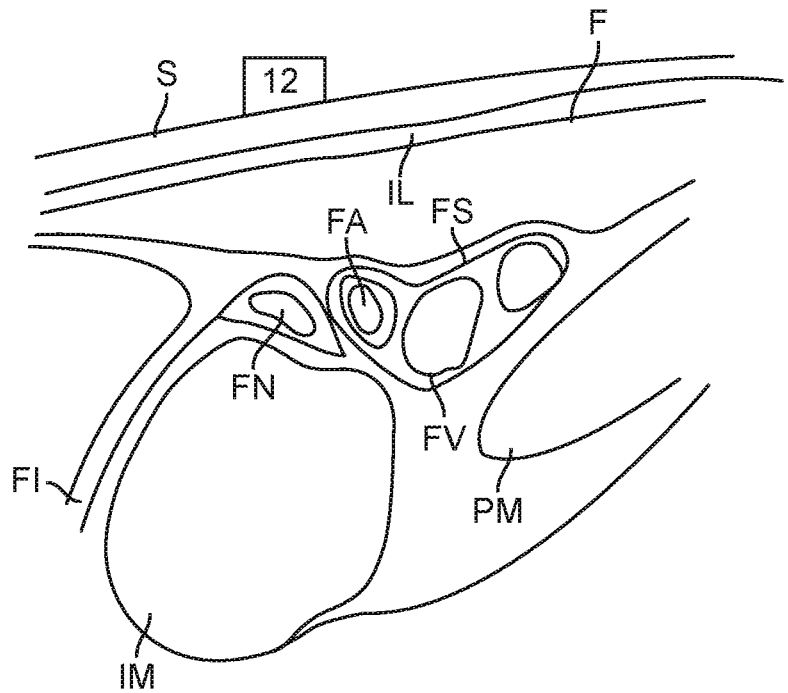

Simulators 11 also may include, in alternative embodiments, a single femoral nerve stimulator or one or more implanted electrodes, for example anchored to inguinal ligament or positioned within the femoral vein near the femoral nerve. Since the femoral nerve innervates the muscles that extend the knee, the femoral nerve may be stimulated directly to capture multiple muscles instead of stimulating individual neuro-muscular junctions of those muscles. As the nerve is positioned closer to the skin near the inguinal area, a stimulator patch may be placed at that location, as shown in FIGS. 25A and 25B. In particular, in FIG. 25A, skin patch 12 constructed in accordance with the present invention is disposed near the inguinal area. FIG. 25B depicts anatomy underlying skin S upon which skin patch 12 is disposed, including femoral nerve FN, femoral artery FA, femoral vein FV, femoral sheath FS, fat F, inguinal ligament IL, fascia iliaca FI, iliopsoas muscle IM, pectineus muscle PM. Nerve depth in this region is known to be 2-7 cm, depending on the body mass index (BMI) of the individual, where the majority of the variation is due to the thickness of the fat layer below the skin.

Stimulation also may be coordinated so that it is applied to the different muscles to minimize lateral and rotational forces placed on the knee joint, for example using feedback from one or more accelerometers. Any of the safety features and sensors described previously may be employed, including for example an auto-shutoff function that stops stimulations when the patient is standing or walking. Some embodiments may use electrical impedance spectroscopy to measure the extent of swelling in and around the knee joint, which may be used as feedback to determine when to end, pause or adjust therapy. These and other features of system 10 and method 40 may be applied not only to the treatment of knee OA but to the treatment of any other joints as well, such as but not limited to the shoulder, elbow, hip and ankle joints.

Theoretical Modeling and Experimental Results

A series of investigations were undertaken to assess the feasibility of muscle contraction stimulation system and methods of the present invention, including a theoretical analysis of the current distribution in tissue, a finite element analysis, in vitro studies using a physical model, and in vivo experiments on human subjects. These studies are described below.

Figure 26:
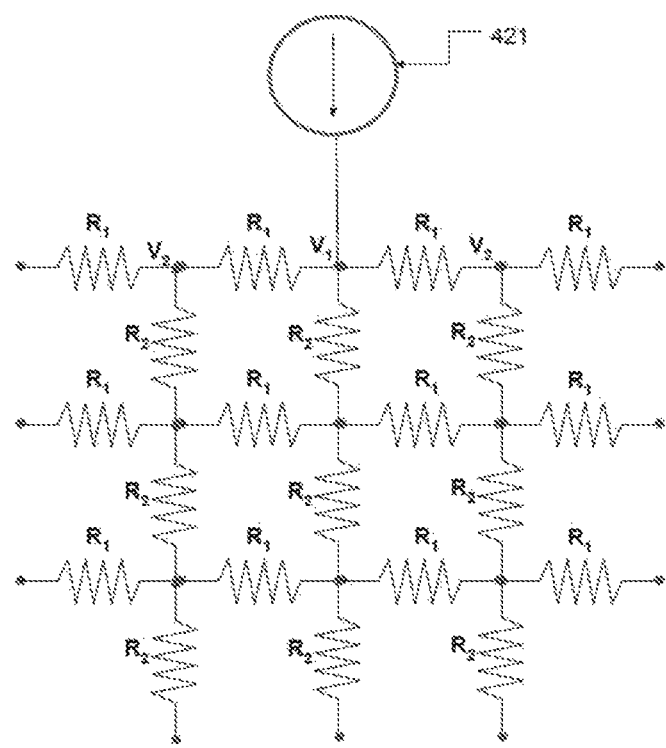
FIG. 26 is an illustration of an approximated model of the tissue that is being stimulated based on electrical circuit theory.

To determine the potential to reduce inadvertent stimulation of sensory nerves by reconfiguring a stimulation electrode to a laterally adjacent position, a mathematical model of the current transmission in tissue was developed, which is depicted in FIG. 26. In this model, lateral impedances that are parallel to the skin surface are represented using the resistors that are labeled $R_1$, while impedances that are normal to the skin surface are modeled as resistors labeled $R_2$. A current source, 421, is assumed to inject an electrical current into the node that is labeled as $V_1$ and the node to be avoided is labeled as $V_2$. For this study, the return electrode is assumed to be positioned away from the node $V_1$, hence the current flow is mainly into the tissue. The ratio $V_2/V_1$ therefore corresponds to the reduction in the stimulation amplitude as one moves laterally away from a node to be avoided.

Figure 27A:
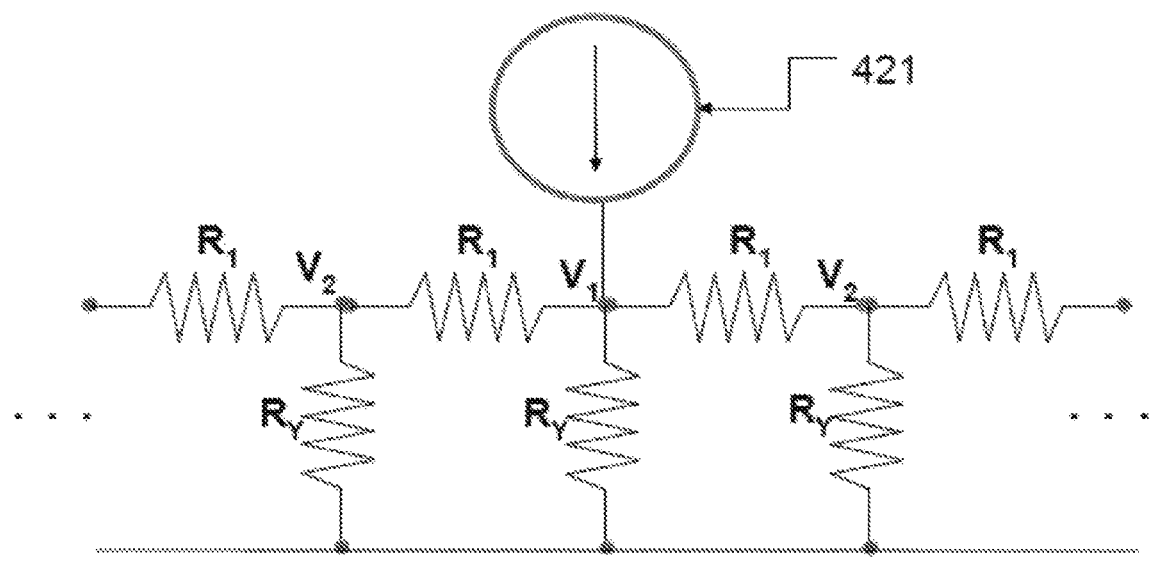
FIGS. 27A to 27C illustrate simplified versions of the approximated model of the tissue that is being stimulated based on electrical circuit theory.
Figure 27B:
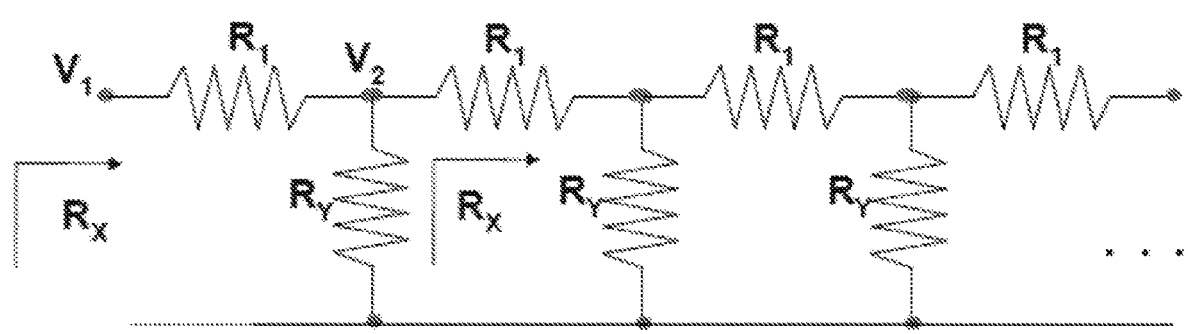

Since the geometry of the model shown in FIG. 26 is symmetrical, it can be simplified to the model shown in FIG. 27A, where the resistors that are labeled as $R_Y$ represent the impedance seen by the electrical current as it travels downward into the tissue. Since the interest is in a single node, $V_2$, only half of the resistor ladder need be studied without a loss of accuracy, as shown in FIG. 27B. The resistor ladder of FIG. 27B is an infinite one, meaning that it extents to infinity. At each step of the ladder, there is another infinite resistor ladder extending to the right hand side of the figure. Furthermore, the infinite resistor ladders seen at each step of the ladder are identical, and it can be represented with $R_X$. The value of $R_X$ may be determined as follows:

$$R_X = R_1 + R_X // R_Y \qquad \text{[Equation 1]}$$

$$R_X = R_1 + \frac{R_X R_Y}{R_X + R_Y} \qquad \text{[Equation 2]}$$

$$R_X = \frac{R_1(R_X + R_Y) + R_X R_Y}{R_X + R_Y} \qquad \text{[Equation 3]}$$

$$R_X^2 + R_X R_Y = R_1 R_X + R_1 R_Y + R_X R_Y \qquad \text{[Equation 4]}$$

$$R_X^2 - R_1 R_X - R_1 R_Y = 0 \qquad \text{[Equation 5]}$$

solving for $R_X$:

$$R_X = \frac{R_1 \pm \sqrt{R_1^2 + 4R_1 R_Y}}{2} \qquad \text{[Equation 6]}$$

or $$R_X = \frac{R_1}{2}\left[1 \pm \sqrt{1 + 4\frac{R_Y}{R_1}}\right] \qquad \text{[Equation 7]}$$

and because negative resistance is not possible, $$R_X = \frac{R_1}{2}\left[1 + \sqrt{1 + 4\frac{R_Y}{R_1}}\right] \qquad \text{[Equation 8]}$$

Figure 27C:
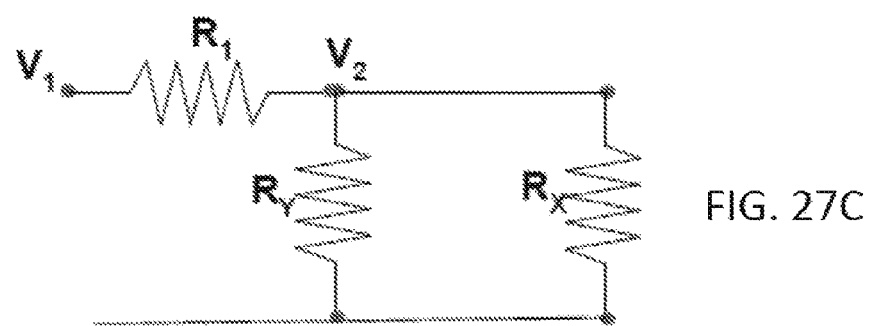

Once the value of $R_X$ is determined using the above equations, the model may be further simplified as depicted in FIG. 27C. In that case, the ratio $V_2/V_1$ may be computed as follows:

$$\frac{V_2}{V_1} = \frac{R_Y // R_X}{1 + R_Y // R_X} \qquad \text{[Equation 9]}$$

Inspection of the above equation indicates that the ratio $V_2/V_1$ is always less than one, indicating that the excitation at the node to be avoided, i.e. $V_2$, will always be less than that of the excitation at the node of stimulation, i.e. $V_1$. In order to estimate of the numerical value of the reduction, it can be assumed that the resistance in all directions is constant, i.e.

$$R_1 = R_Y = R_C \qquad \text{[Equation 10]}$$

Then, combining equations 8 and 10, $$R_X = \frac{R_C}{2}[1 + \sqrt{5}] = 1.618\, R_C \qquad \text{[Equation 11]}$$

and $$R_Y // R_X = \frac{1}{\frac{1}{R_C} + \frac{1}{1.618\, R_C}} = 0.618\, R_C \qquad \text{[Equation 12]}$$

Combining equations 9 and 11, $$\frac{V_2}{V_1} = \frac{0.618\, R_C}{1 + 0.618\, R_C} \frac{0.618}{1.618} = 0.38 \qquad \text{[Equation 13]}$$

Accordingly, the numerical value produced by the equation 13 indicates that the displacement of the electrode from a single node to another reduces the excitation amplitude to less than 40 percent of the original value.

Figure 28A:
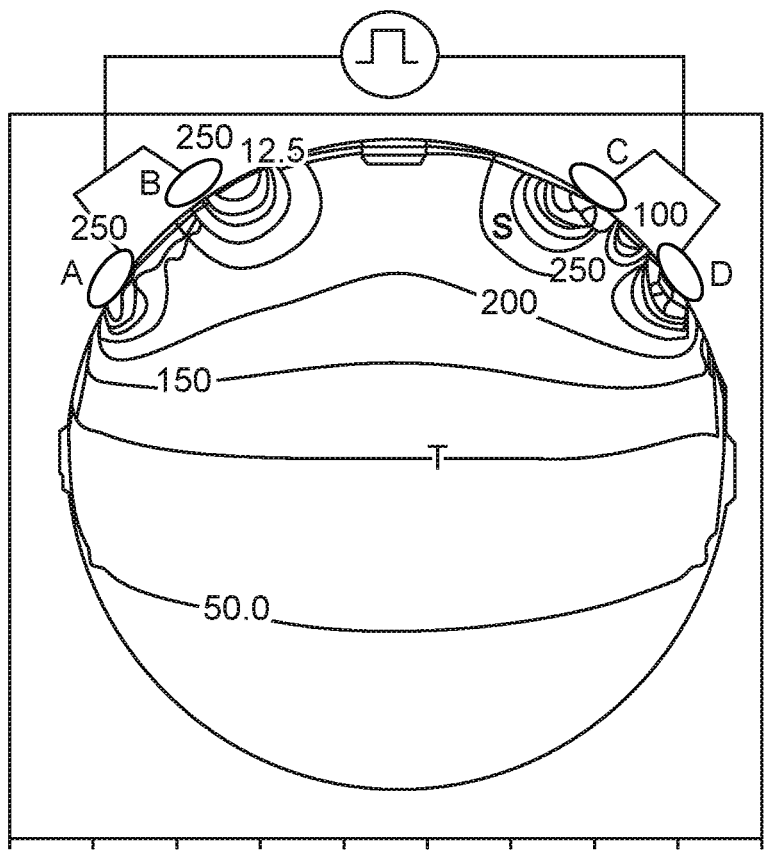
FIGS. 28A and 28B are, respectively, a contour plot of the normalized intensity of electrical current density in the tissue when two pairs of electrode are positioned symmetrically and a contour plot of the normalized intensity of electrical current density in the tissue when two pairs of electrode are positioned with an offset, wherein the data was obtained using an in silico model.
Figure 28B:
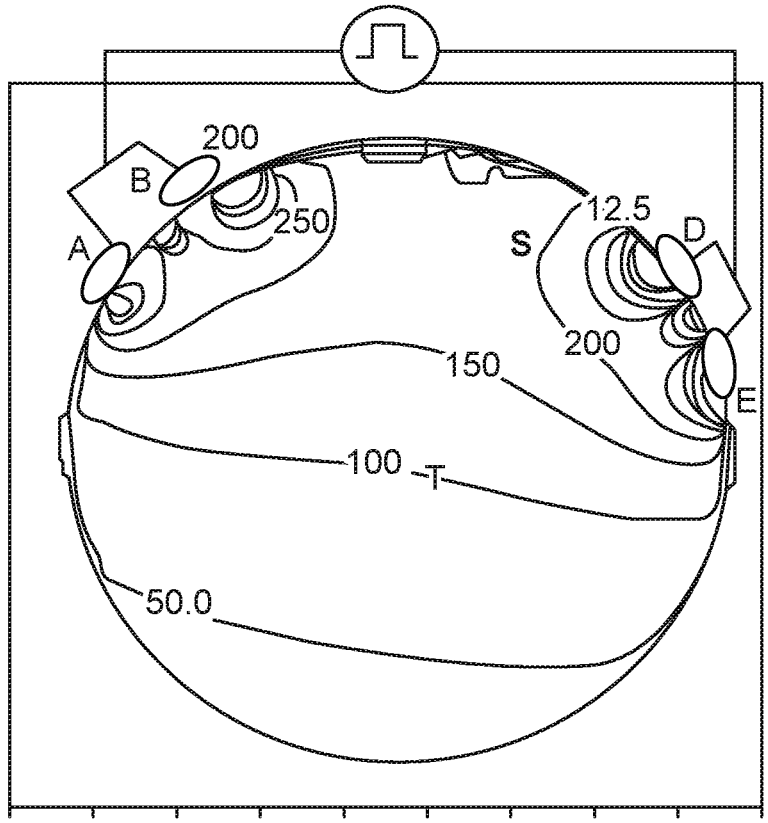

Based on the results of the foregoing theoretical analysis, a numerical simulation using an in silico model was conducted to evaluate the utility of modifying the pattern of the electrode segments to alter the path that the electrical current takes. The results of that simulation are depicted in FIGS. 28A and 28B, which was generated using a custom finite difference program to solve the 2D Laplace's Equation using the Variational Method. The in silico simulations were performed using a 70×70 grid, giving 4,900 equispaced nodes encompassing 9,522 triangular elements. FIG. 28A depicts lines of current density for a pair of electrode elements A and B used to deliver a current into tissue, where C and D formed a counter electrode. As shown in FIG. 28A, the electrodes and counter electrodes are positioned symmetrically, forming a mirror image relative to a vertical axis. The outer circle represents the skin surface for the simulated tissue. Curves within the circle represent the regions where the current density is uniform, with scaled numerical values. Letter "T" within the circle represents the location of the target motor nerve. As will be observed from FIG. 28A, a stimulation current with relative amplitude of 100 reaches to the target position "T." Letter "S" represents a sensory nerve, which when stimulated results in an unacceptable pain sensation. As indicated in FIG. 28A, the amplitude of current intensity at the sensory nerve location S is approximately 300 units, corresponding to an unacceptably high pain level.

Referring now to FIG. 28B, electrode element C is turned off and electrode element D is paired with E. In this case, the electrode pairs are no longer positioned symmetrically across the vertical axis, and the resulting current pathways are altered. The target location "T" still receives a stimulation at an amplitude of 100 relative units. However, sensory nerve "S" now receives a stimulation at an amplitude of less than 200 relative units, much less than amount of excitation at that location compared to the electrode arrangement of FIG. 28A.

Figure 29:
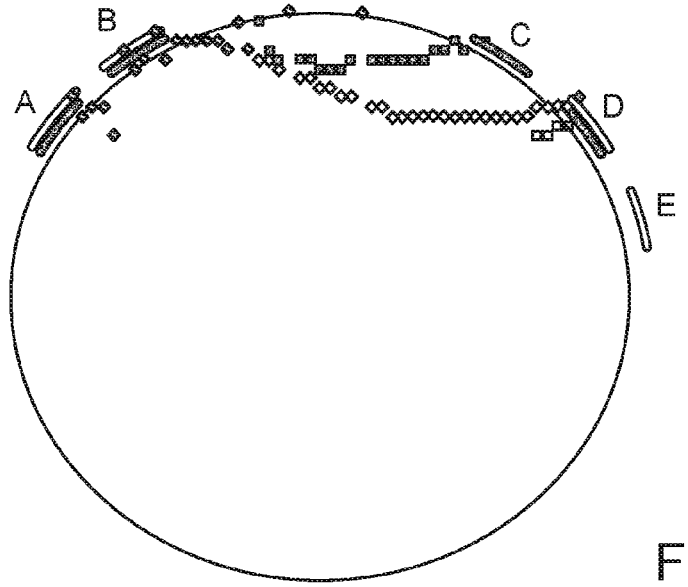
FIG. 29 is a two-dimensional plot of maximal electrical current density in the tissue when two pairs of electrode are positioned symmetrically or with an offset, wherein the data was obtained using an in silico model.
Figure 30:
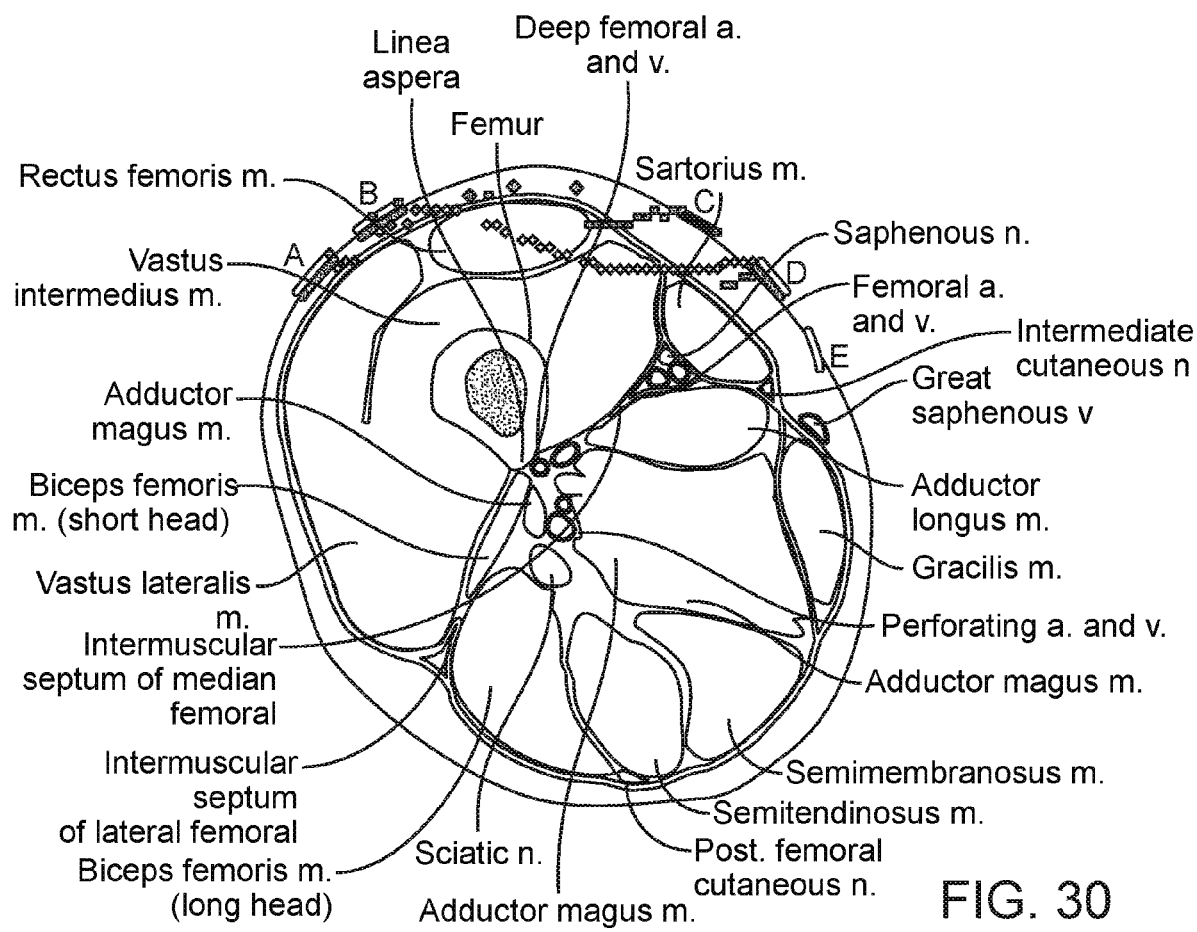
FIG. 30 is the two-dimensional plot of maximal electrical current density in the tissue obtained using an in silico model, superimposed over a diagram of cross section of a leg, when two pairs of electrode are positioned symmetrically or with an offset.

FIG. 29 depicts the changes in the maximum current path for the electrode arrangements of FIGS. 28A and 28B. Again, for both cases the current enters the tissue from the electrode formed by the pair of elements labeled as A and B. For a return electrode formed by electrode pair C and D, the path of the maximum current is illustrated with gray squares. For a return electrode formed by electrode pair D and E, the path of the maximum current is illustrated with black diamonds. As described above, the current path is shaped by the selection of active electrodes. FIG. 30 schematically depicts the advantage of the ability to alter the maximum current path when applied to a human leg, and includes the image of the maximal current path calculated using the finite difference method superimposed over a cross sectional view of a human leg.

Figure 31A:
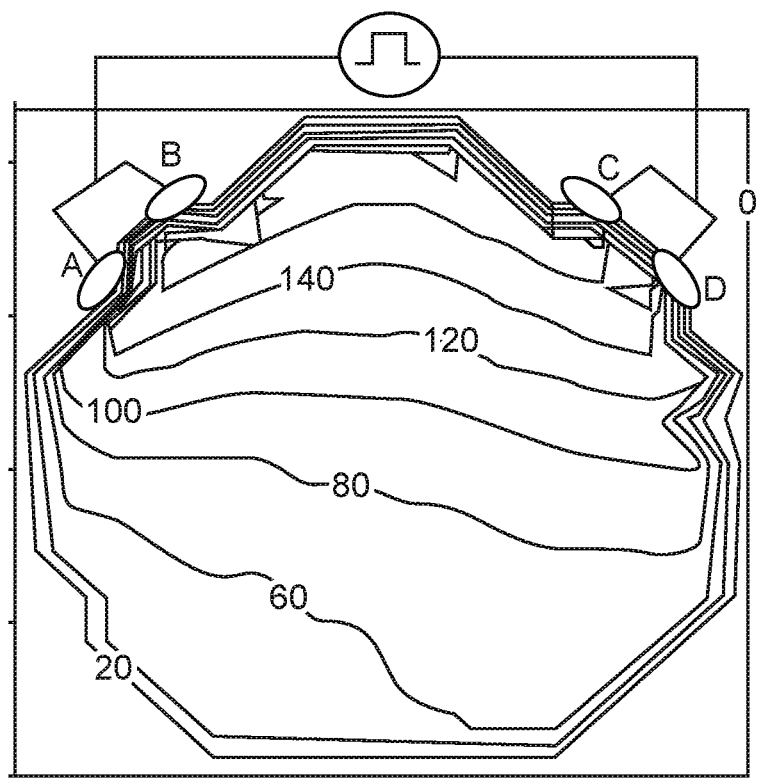
FIGS. 31A and 31B are, respectively, a contour plot of the normalized intensity of electrical current density in the tissue when two pairs of electrodes are positioned symmetrically and a contour plot of the normalized intensity of electrical current density in the tissue when two pairs of electrodes are positioned with an offset, wherein the data was obtained using an in vitro model.
Figure 31B:
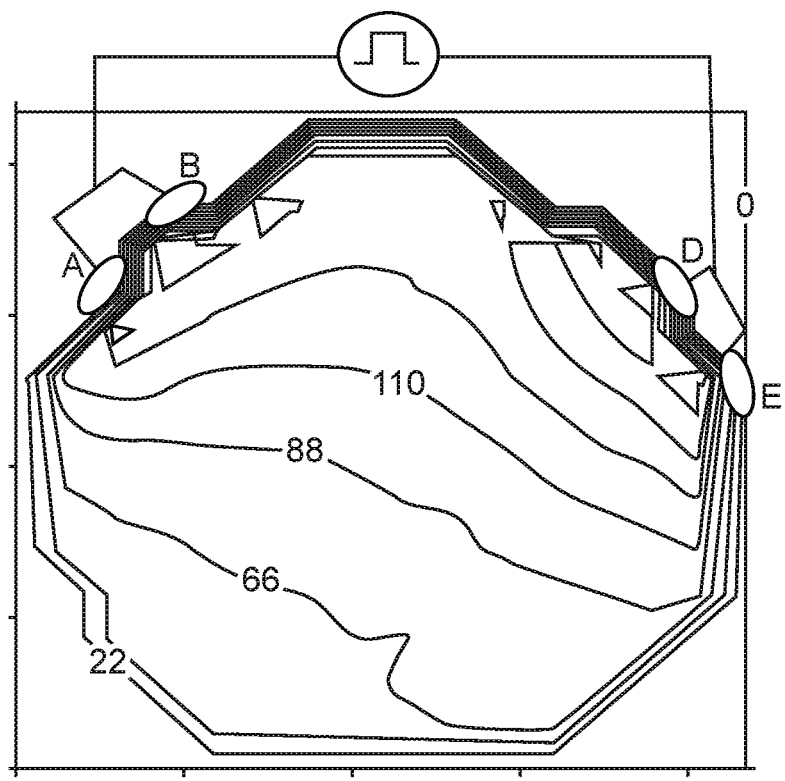

Results from the in silico study were further evaluated using an in vitro model. This saline model allowed the measurements to be made using an 18×18 grid, resulting in a 158 elements, using a conductive material representing tissue. Data collected during the in vitro study is presented in FIGS. 31A and 31B. Once again the traces of uniform current strength were plotted inside the test area and demonstrate that the current path can be modified as predicted during the in silico studies of FIGS. 28A and 28B.

Figure 32:
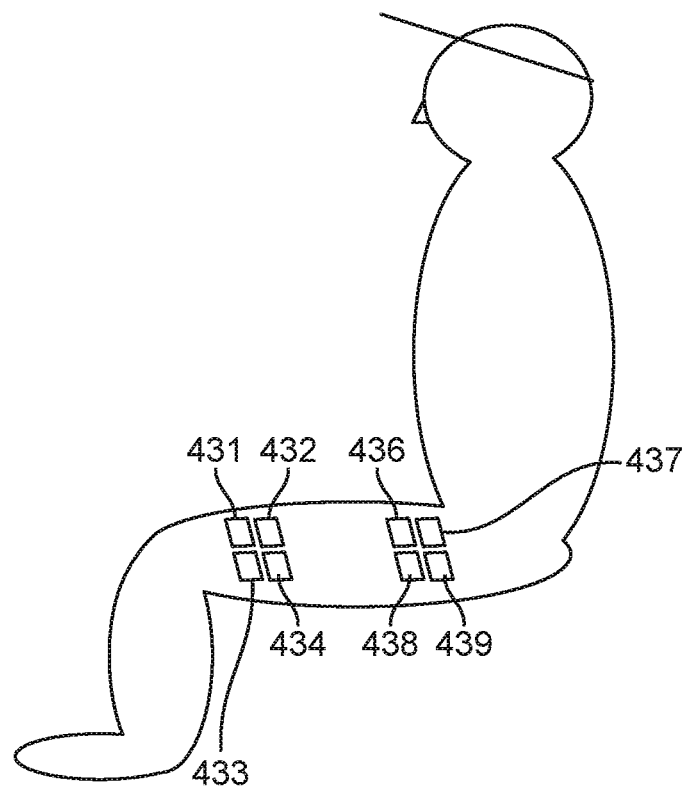
FIG. 32 is a diagram showing electrode placement during an in vivo study that was conducted to demonstrate the utility of one of the methodologies for the reduction of pain associated with the application of electrical stimulation.

In order to further demonstrate the utility of current path shaping, an in vivo study was conducted. In this case, two sets electrodes, four in each set, were positioned on the left leg of an experimental subject, as shown in FIG. 32. Four electrodes 431, 432, 433 and 434 were located near the knee and connected in parallel to form one of the poles for the stimulation. The remaining four electrodes, 436, 437, 438 and 439 were employed to form the opposing pole. Once the stimulation voltage was raised over 22 Volts, the subject reported a pain sensation near his knee. Then, each of the electrodes near the knee, i.e., 431, 432, 433 and 434, were disconnected, one at a time, and the subject was asked to describe his level of pain each time. When electrode 434 was disconnected, discomfort was eliminated and the stimulation amplitude was raised until a strong muscle contraction could be observed without any pain perceived by the subject.

Above described experiments, namely the theoretical analysis of the current distribution in the tissue, the finite element analysis on a digital computer, in vitro studies using a physical model and the acute in vivo study with eight electrodes all demonstrate the feasibility of shaping the current path with the tissue to steer the stimulation to the neuromuscular target while avoiding the stimulation of the pain sensors.

In a further investigation of functional outcomes, two healthy white adult males consumed predetermined meals for two consecutive nights and fasted overnight. On the following morning, blood draws were conducted to measure the fasting plasma insulin (FPI) concentration and the fasting plasma glucose (FPG) concentration, which in turn were used to calculate the baseline HOMA-IR scores as follows:

$$\text{HOMA-IR} = (\text{FPI}(mU/L) \times \text{FPG}(mmol/L))/22.5 \qquad \text{[Equation 14]}$$

where FPI is fasting plasma insulin concentration and FPG is fasting plasma glucose concentration, both of which were measured from the blood sample.

HOMA-IR scores can be interpreted as follows:

HOMA-IR<2 indicates normal insulin resistance,

HOMA-IR between 2 and 3 is an indicator of early insulin resistance,

HOMA-IR from 3 to 5 is an indicator of moderate insulin resistance, and

HOMA-IR>5.0 is an indicator of severe insulin resistance.

Two days later, both subjects identified the motor points for tolerable transcutaneous muscle stimulation of their quadriceps muscles using two 1 square inch saline-soaked sponges connected via separate lead wires to an Empi Continuum™ Neuromuscular Stimulator. The areas were dried, marked with ink, and then adhesive electrodes were applied at these locations. Motor points also were identified and electrodes placed on the hamstring. Neuromuscular electrical stimulation was applied to the quadriceps and hamstring muscles of both legs overnight while the subjects slept. A second venous blood draw was performed the following morning for measurement of FPI and FPG concentrations and the calculation of a HOMA-IR score, producing the results listed Table 1. These test data indicate that, for healthy subjects, neuromuscular electrical stimulation lowered the subjects' HOMA-IR scores from baseline. It is expected that HOMA-IR score improvement would be similar or better for subjects with a moderate or severe baseline insulin resistance.

TABLE 1

| Subject Number | Date DD-MMM-YYYY | Case Base/Stim | Glucose mg/dL (G) | Insulin mIU/L (I) | HOMA-IR Score = (G × I)/405 |
|---|---|---|---|---|---|
| 1 | 21-Nov-2015 | Baseline | 85 | 3.4 | 0.714 |
| 1 | 23-Nov-2015 | Stim | 82 | 3.0 | 0.607 |
| 2 | 21-Nov-2015 | Baseline | 88 | 4.9 | 1.065 |
| 2 | 23-Nov-2015 | Stim | 81 | 3.6 | 0.720 |

Figure 33:
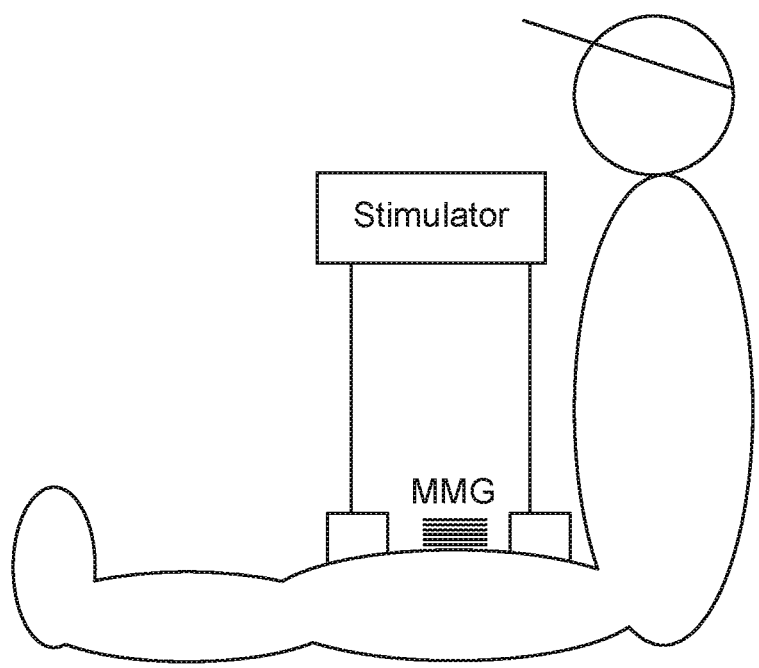
FIG. 33 is a side view of a patient with a muscle contraction stimulation patch containing an mechanomyography ("MMG") sensor placed to target the leg muscles, according to one embodiment.

In another study conducted by the inventors, two electrodes were placed over the quadriceps muscles of the left leg of a male subject, as depicted in FIG. 33. The subject was seated on the floor with his legs extended, so that all contractions were isovolumetric, i.e. the contractions caused no significant shortening of the muscle. A stimulator was programmed to produce biphasic pulses lasting 400 microseconds at 50 Hz. Between pulse trains, stimulation remained off for 2 seconds, then the amplitude of stimulation pulses ramped up for 2 seconds. Afterwards, stimulation was kept on for a total of 3 seconds before being ramped down during a 1 second interval, which in turn was followed by another 2 second interval of off time before the start of the next stimulation cycle.

Figure 34:
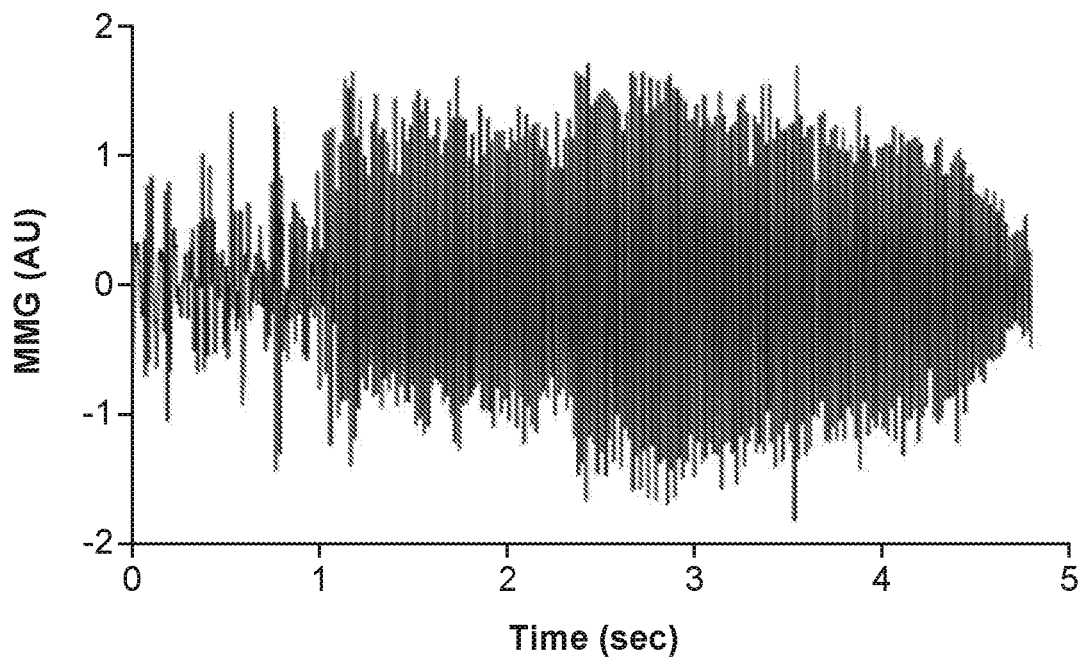
FIG. 34 is an illustrative time domain plot of an MMG signal that is collected from the leg muscle of a person during a single stimulation session using a system as depicted in FIG. 33.
Figure 35:
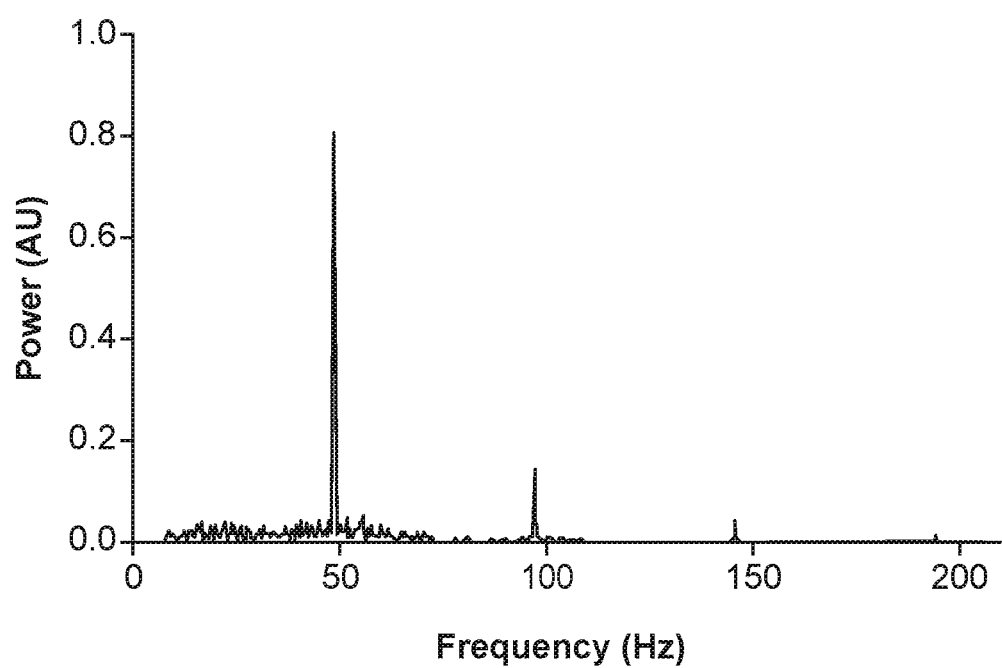
FIG. 35 is the frequency domain plot of the MMG signal that is collected from the leg muscle of a person during a single stimulation session corresponding to the time domain plot of FIG. 34.

It was noticed that stimulation having an amplitude of 30 Volts produced quivering of the muscle, indicating that stimulation at 30 Volts was below that necessary for maximal contraction. Full strength contractions were observed when the stimulation amplitude was raised to 35 Volts. FIG. 34 shows a time domain trace of the MMG signal for a portion of a single cycle, while FIG. 35 shows the corresponding frequency domain trace. It can be observed that the main power in the MMG signal resides at 50 Hz, which is the stimulation frequency, with harmonics integer multiples of 50 Hz, i.e., at 100 Hz, 150 Hz, 200 Hz and so on.

Figure 36:
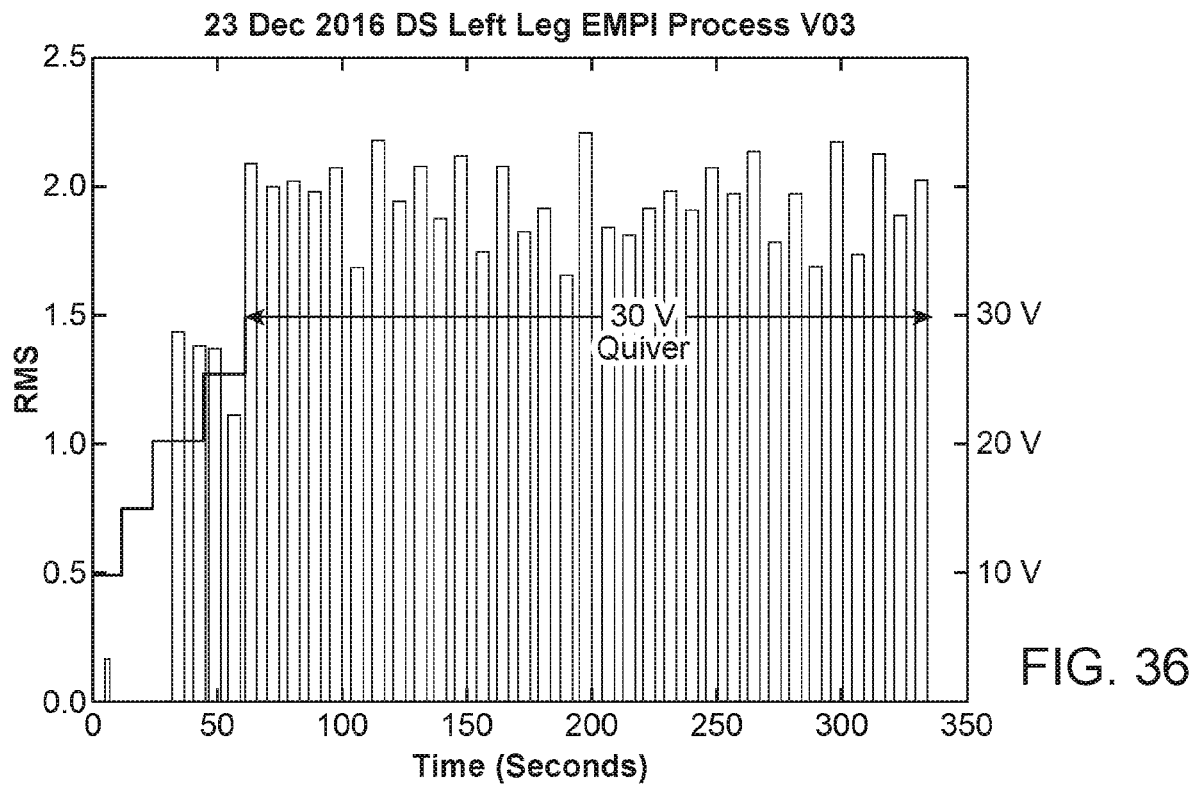
FIG. 36 is a plot depicting root-mean-square ("RMS") value of the MMG signal that is collected from the leg muscle of a person during a long stimulation session, during which the stimulation amplitude was kept below that required for maximal contraction.
Figure 37:
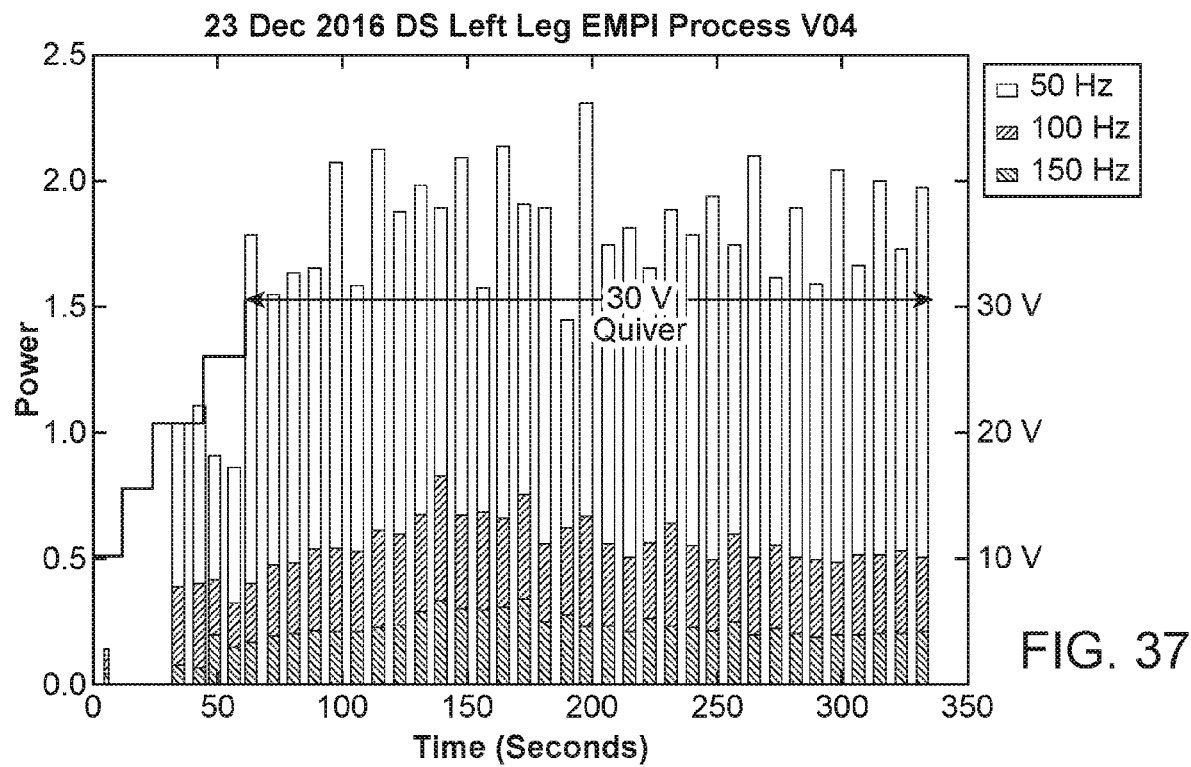
FIG. 37 is a plot depicting the power content of MMG signal at three different frequencies where the MMG signal is collected from the leg muscle of a person during a long stimulation session and the stimulation amplitude was kept below that required for maximal contraction.

Referring to FIGS. 36 and 37, the signals from an MMG sensor, applied as shown in FIG. 33, increase as the strength of the contraction increases. Accordingly, the control unit may be programmed to increase stimulation amplitude until there is no corresponding increase in the MMG signal, indicating that maximal contraction condition has been reached.

More specifically, FIG. 36 shows the root mean square (RMS) value of the MMG signal in each cycle of the stimulation experiment, when the stimulation amplitude was increased up to 30 Volts, resulting in quivering, but not full contraction of the muscle. FIG. 37 shows the power value of the MMG signal during each cycle. Three traces, one for 50 Hz, one for 100 Hz and one for 150 Hz, were generated by adding the power values for all frequencies that are within +/−5 Hz of the chosen frequency. For example, the trace for 50 Hz shows the total power that is in the range from 45 Hz to 55 Hz. It can be observed from the traces shown in FIGS. 36 and 37 that sub-maximal contractions do not show a clear trend over time.

Figure 38:
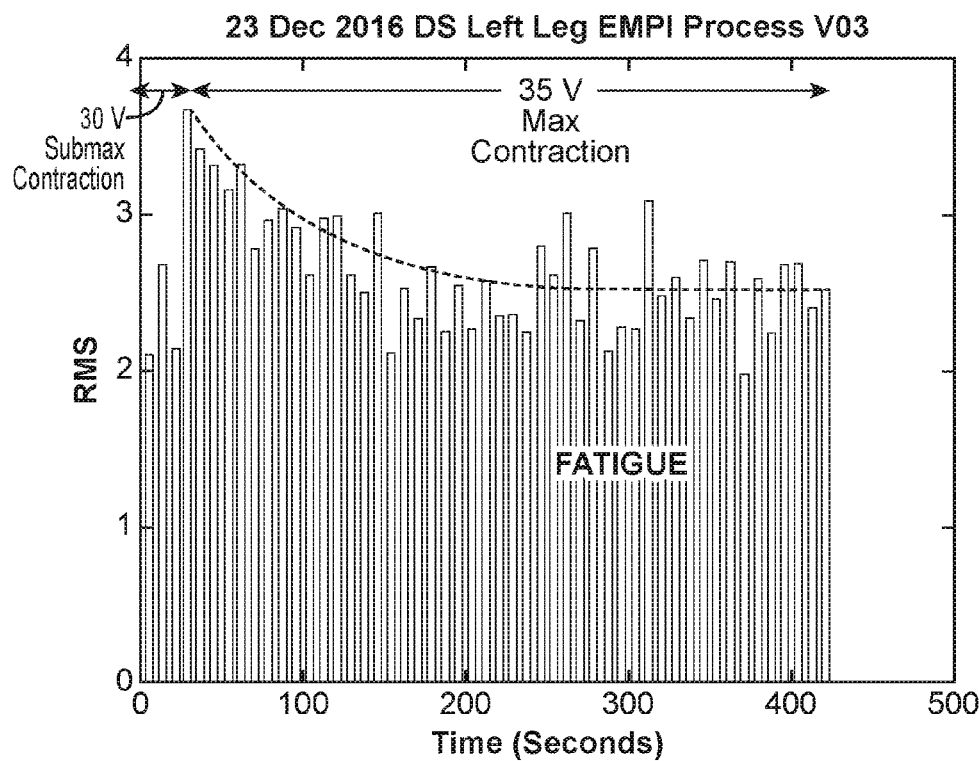
FIG. 38 is the RMS value of the MMG signal that is collected from the leg muscle of a person during a long stimulation session where the stimulation amplitude was kept above that required for maximal contraction.
Figure 39:
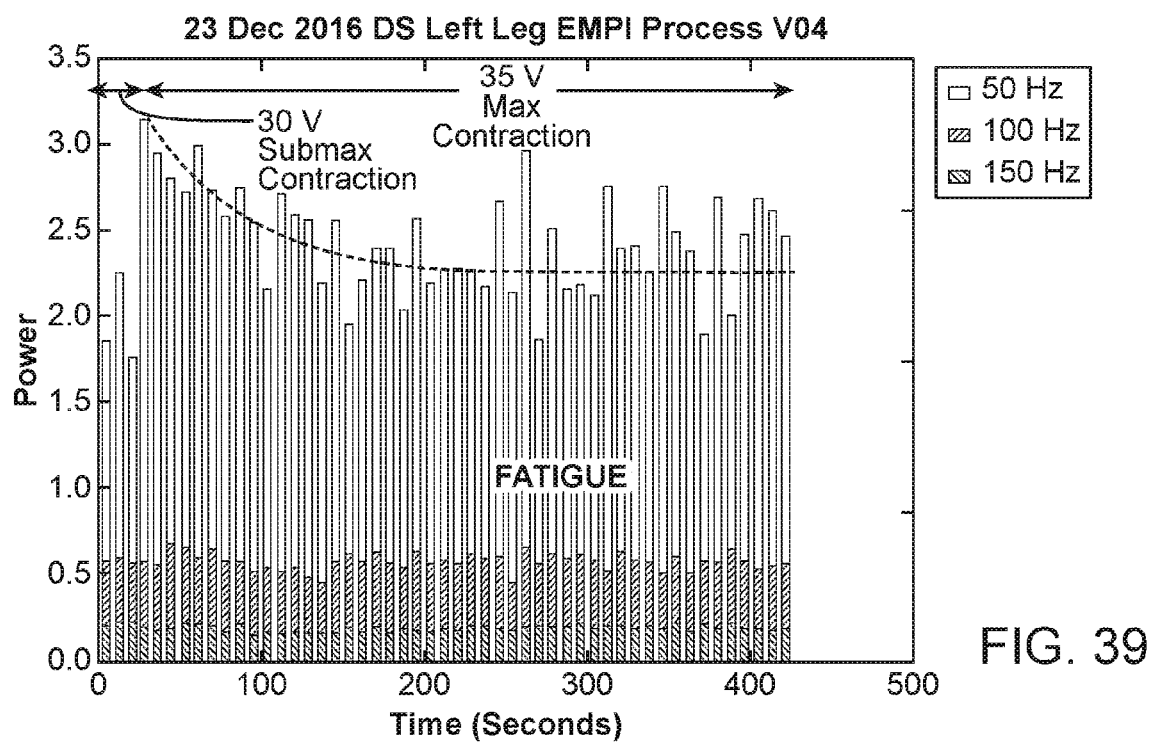
FIG. 39 is the power content of MMG signal at three different frequencies where the MMG signal is collected from the leg muscle of a person during a long stimulation session where the stimulation amplitude was kept above that required for maximal contraction.

FIGS. 38 and 39 show that the signals from the MMG sensor decrease as the strength of the contraction decreases as a result of fatiguing of the muscle. This information can be processed by the control unit to pause or terminate the therapy when a muscle fatigue condition is detected. More specifically, FIG. 38 shows the root mean square (RMS) value of the MMG signal in each cycle of the stimulation experiment, as described above, when the stimulation amplitude was increased up to 35 Volts, resulting in full contraction of the muscle. FIG. 39 shows the power value of the MMG signal during each cycle. As it can be observed from the traces shown in FIGS. 38 and 39, maximal contractions exhibit a decay function that reaches steady state as the muscle fatigues, approximately within two minutes of repeated contractions.

Implantable Muscle Stimulation Systems and Methods

The muscle contraction stimulation system of the preceding embodiments generally are directed to transcutaneous stimulation in which a skin patch is applied to a patient's skin. In alternative embodiments constructed in accordance with the principles of the present invention, pain sensations may be relieved by implanting the electrodes used for stimulating the muscle subcutaneously, with power supplied either via implantable power sources or wirelessly, e.g., by inductive energy transfer.

Figure 40:
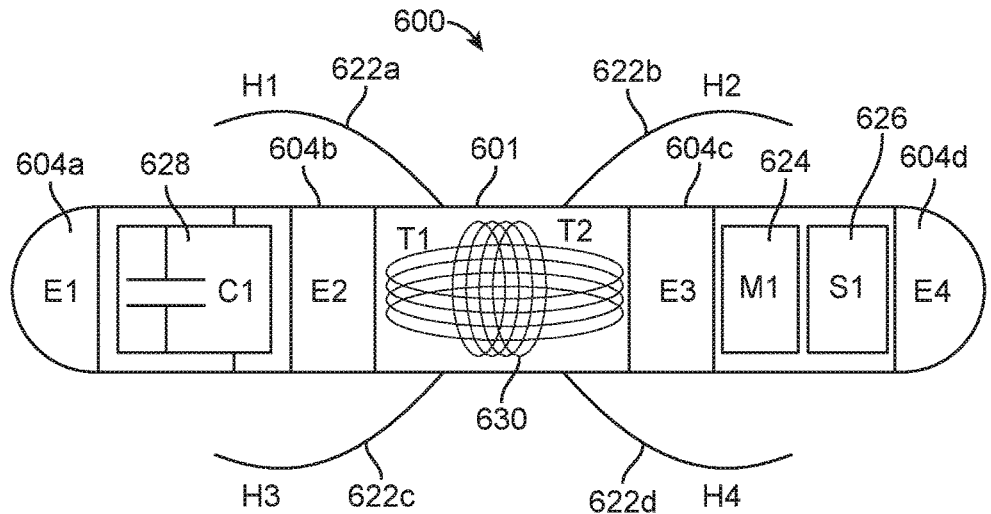
FIG. 40 is an axial cross-sectional view of an implantable muscle contraction stimulator of the present invention.

Referring now to FIG. 40, an implantable device is described. Implantable device 600 includes four electrodes 604a, 604b, 604c and 604d, and may be powered using a battery or via externally applied radio frequency (RF) signals received by circuit 630 having coils T1 and T2. Coils T1 and T2 also may be for communication with external devices, such as a patient interface unit. Coils T1 and T2 may be constructed on different planes, preferably positioned orthogonally, to form a diversity receiver, which improves communications with external devices positioned along different planes. Energy received by the coils is stored on capacitor 628 until it is needed to generate stimulation to be delivered to the tissue. Processor 624 controls operation of implantable device 600, as well as communications with external devices. Once implanted in the tissue, device 600 becomes fixed to targeted tissue using hooks 622a, 622b, 622c and 622d.

In one preferred embodiment, implantable device 600 has a diameter of 4 mm (12 French) and length of 4 cm, although other external dimensions may be used. Implantable device 600 advantageously locates the electrodes in the vicinity of the target motor nerve, thereby reducing the risk of unintentional stimulation of sensory nerves. Furthermore, as migration of implantable device 600 is minimized by the presence of hooks 622a, 622b, 622c and 622d, potential errors caused by the mis-positioning the electrodes are greatly reduced.

Figure 41A:
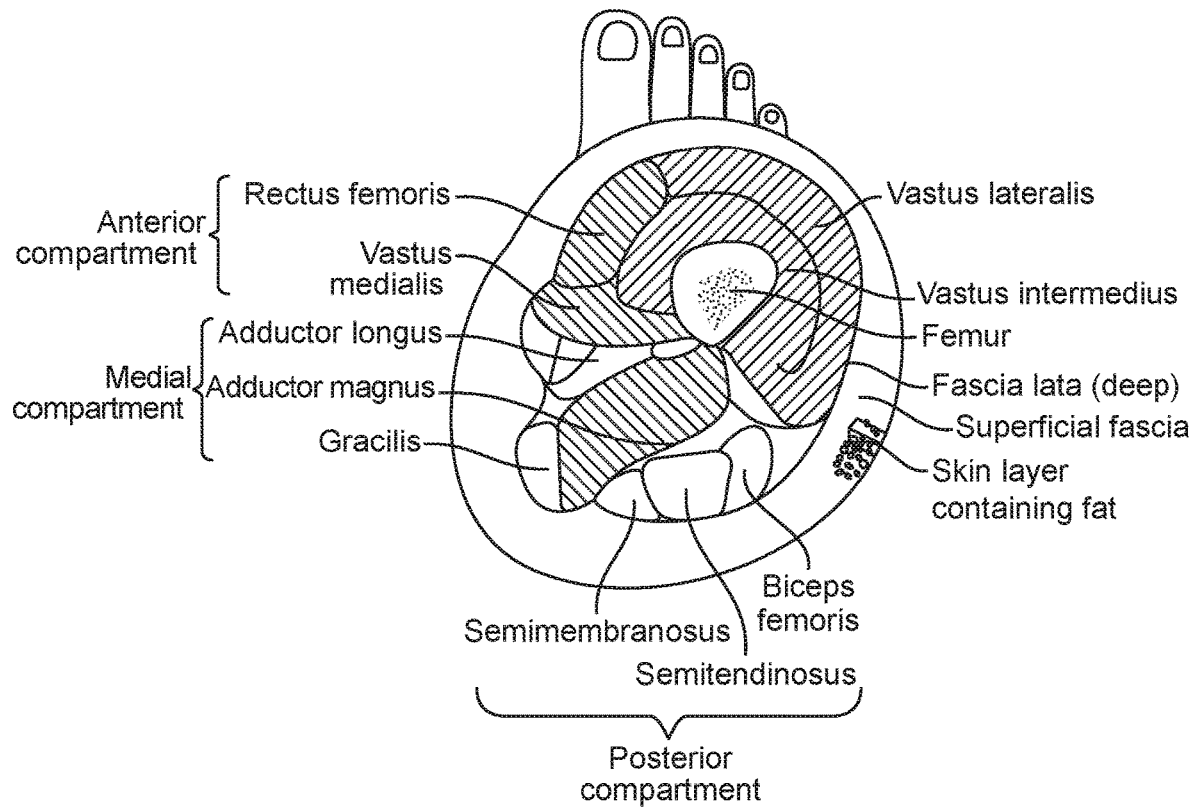
Figure 41B:
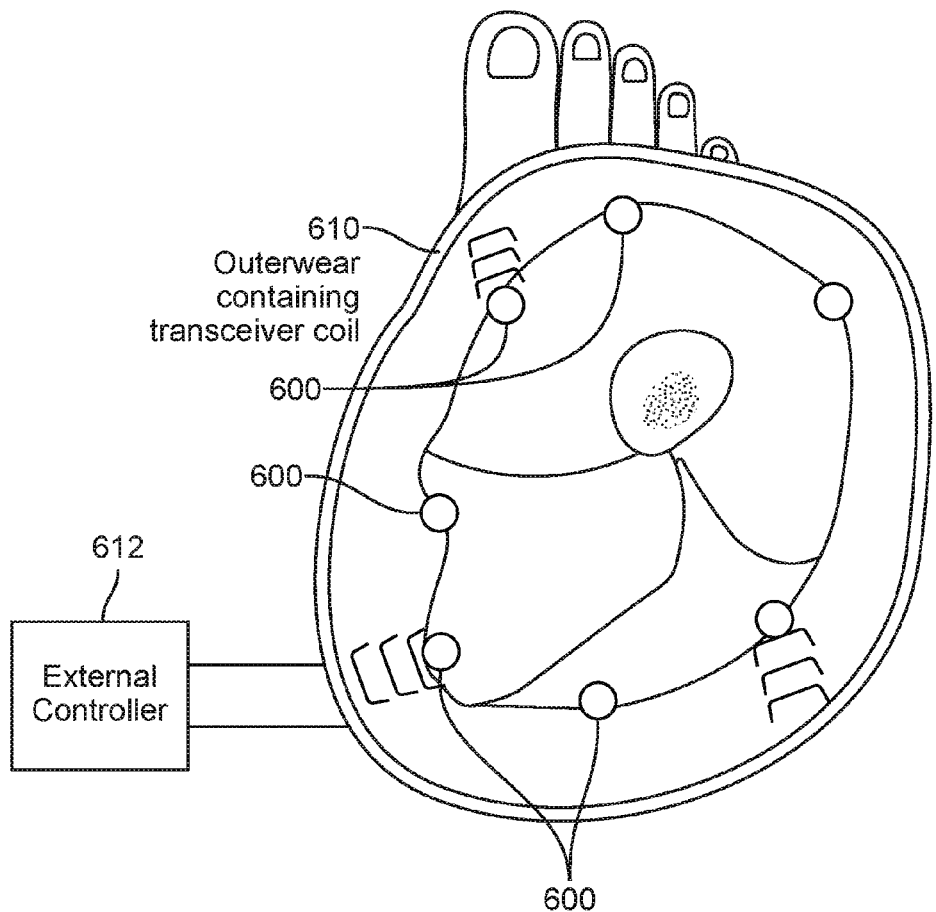
FIG. 41B is a cross sectional view of a leg which is implanted with muscle contraction stimulators configured to be wirelessly coupled to an external electronic controller.
Figure 42:
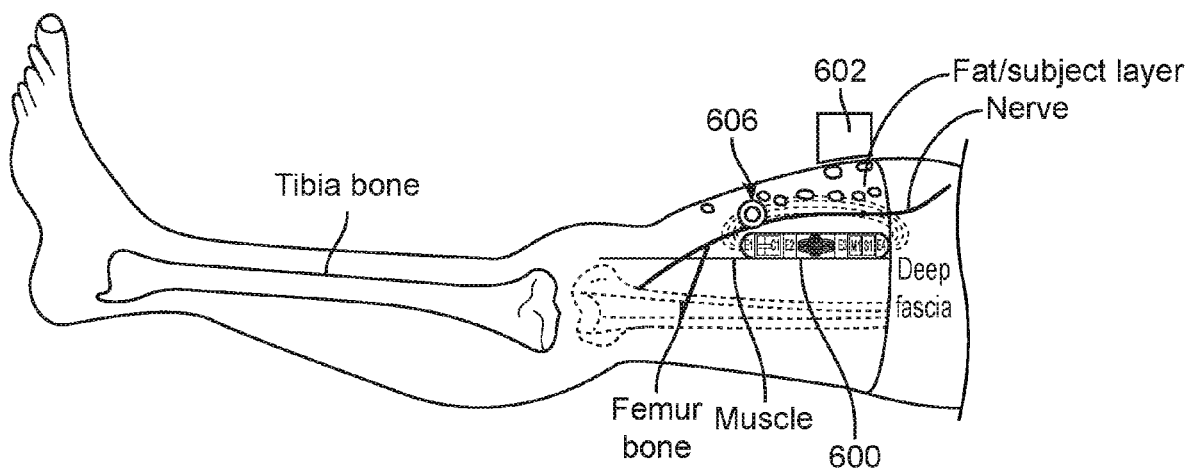
FIG. 42 is a side view of a leg showing an external controller for activating the implantable muscle contraction stimulators of FIG. 40 in accordance with the principles of the present invention.

FIG. 41A depicts a radial cross-section of a human leg while FIG. 41B depicts the same radial cross-section with multiple implanted devices 600. For this embodiment, the external coils used to energize and communicate with implantable device 600 are fixed on garment 610 worn by the patient. The external coils are controlled by external controller 612, which communicates with controller 624 of the implantable device via received 630. FIG. 42 illustrates a patient leg in which he implantable device 600 is implanted as well as transceiver coil 602, which may be kept in place by gravity, a strap or suitable garment. Transceiver coil 602 is coupled to external controller 612, which may supply the stimulation parameters, operational control or energy for implantable device 600.

Figure 43:
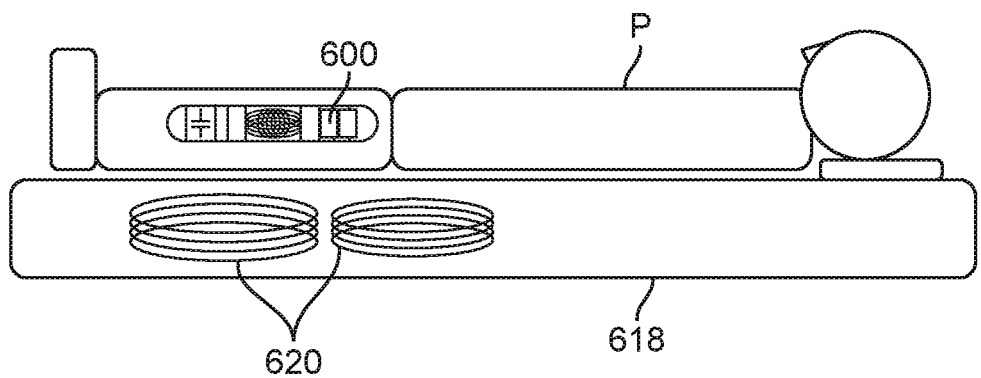
FIG. 43 is a side view of an alternative system for controlling and powering the implantable muscle stimulator system of FIG. 40.

Referring now to FIG. 43, an alternative mode of activation of implanted muscle contraction stimulator 600 in patient P using an external electronic controller is described. In this example, the patient reclines on bed 618 that includes external coils 620, which couple to receiver 630 of implantable device 600. This particular arrangement allows the patients with implantable device 600 to receive therapeutic benefits while they rest or sleep. Although FIG. 43 shows external coils 630 disposed in a bed, it should be understood that the external coils could be included in any other structure that permits a patient to lie or sit, including, but not limited to chairs and couches.

Figure 44:
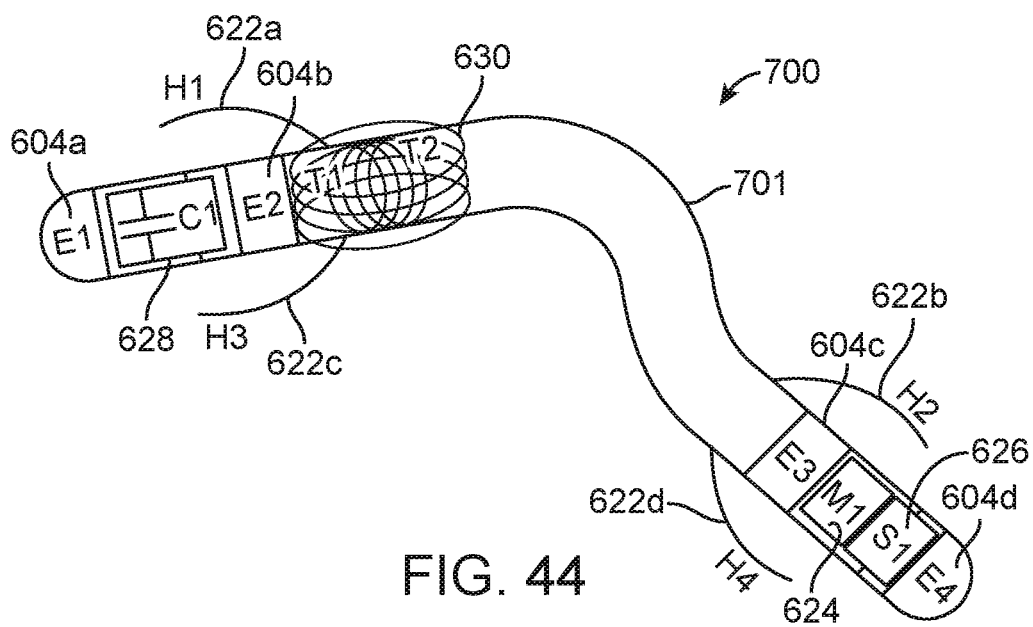
FIG. 44 is an axial cross-sectional view of a flexible implantable muscle contraction stimulator having components similar to that of the implantable muscle stimulator of FIG. 40.

FIG. 44 shows an alternative implantable device embodiment. Implantable device 700 has two ends connected to each other by flexible segment 701. Flexible segment 701 also may be stretchable longitudinally, thereby allowing motion of the device along with the tissue that it is anchored within. Implantable device 700 also reduces the potential for hooks 622a, 622b, 622c and 622d to experiencing excessive force and breakage, or that could cause implantable device 700 to protrude through the skin due to unforeseen motion effects after the implantation.

Figure 45:
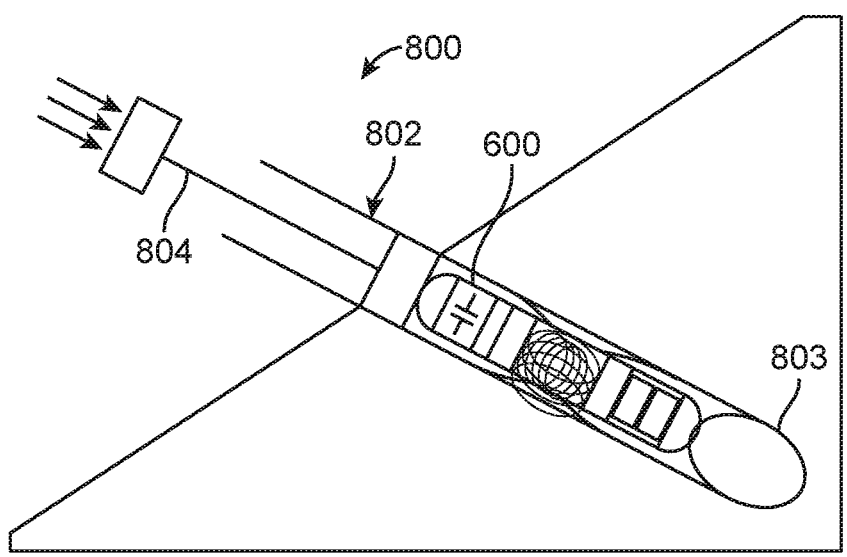
FIG. 45 is an axial cross-sectional view showing implantation of a muscle contraction stimulator depicted in FIG. 40.

FIG. 45 depicts a methods of implanting implantable device 600. Implantable device 600 first is loaded into syringe-type deployment device 802 having distal opening port 803. Once the medical professional determines that distal opening port 803 is located at a desired location, he or she depresses piston 804 to eject implantable device 600 from deployment device 802. Once disposed in the tissue, hooks 622a, 622b, 622c and 622d, expand to fix implantable device 600 in position and prevent subsequent migration.

The foregoing detailed description provides a number of different embodiments and features of muscle contraction stimulation systems, devices and methods constructed in accordance with the principles of the present invention. The description of exemplary embodiments is provided for illustrative purposes and should not be interpreted as limiting the scope of the invention as it is described in the claims. For example, various alterations may be made to a given embodiment, such as a rearrangement of parts, different combinations of components, or the like, without departing from the scope.

What is claimed is:

1. A system for stimulating nervous tissue associated with one or more skeletal muscles of a subject, the system comprising:

a multiplicity of electrodes;
a switching circuit coupled to the multiplicity of electrodes;
a stimulation circuit operatively coupled to the switching circuit;
a physiologic sensor device, configured to generate an output indication of a physiologic parameter based on monitoring by the physiologic sensor device of a physiological parameter of the subject corresponding to a stimulation treatment session;
a processor operatively communicatively coupled to the stimulation circuit and the switching circuit and the physiologic sensor device, the processor programmed to configure the switching circuit to select a subset of the multiplicity of electrodes to provide electrical stimulation to nervous tissue associated with one or more skeletal muscles to improve a disorder comprising at least one of insulin resistance, fatty liver disease, obesity, osteoarthritis, sarcopenia, limb weakness, aerobic deconditioning, cancer, heart failure, chronic venous insufficiency, deep vein thrombosis, peripheral artery disease, lymphedema or hypertension, wherein the processor is programmed to analyze the output indication from the physiologic sensor device to apply one or more criteria to automatically determine whether the output indication from the physiologic sensor device indicates an adverse physiologic response to the stimulation and, when the output indication from the physiologic sensor device indicates the adverse physiologic response to the stimulation, to respond to the indication of the adverse physiologic response to the stimulation; and
a non-transitory medium containing patient interface unit programming, the patient interface unit programming configured for use with a patient interface unit for controlling operation of the processor, switching circuit and stimulation circuit.

2. The system of claim 1, further comprising the physiologic sensor device coupled to the processor to monitor or detect the adverse physiologic response to stimulation comprising at least one of hypoglycemia, skeletal muscle dysfunction, cardiovascular dysfunction, tissue ischemia, or anaerobic muscle activity.

3. The system of claim 1, wherein the physiologic sensor device comprises an ECG sensor providing the output indication, wherein the processor is configured to automatically determine from the output indication the adverse physiologic response to stimulation based on at least one of an elevated heart rate, a QT interval being a shortened QT interval, a "peaked" T-wave, a narrowing of a QRS complex, a lengthening of a PR interval, a loss of P-waves, a widening of a QRS complex, a characteristic morphology of the ECG signal, a "sine wave" morphology, T-wave flattening, T-wave inversion, appearance of a U-wave, prolonged ST interval duration, ST depression, or an ECG indication of at least one of hyperkalemia rhabdomyolysis hypocalcemia, or ischemia.

4. The system of claim 1, wherein the physiologic sensor device comprises a lactate sensor providing the output indication, wherein the processor is configured to automatically determine from the output indication the adverse physiologic response to stimulation based on at least one of a lactate level or a lactic acid level rising beyond a specified threshold level.

5. The system of claim 1, wherein the physiologic sensor device comprises a muscle fatigue sensor providing the output indication, wherein the processor is configured to automatically determine from the output indication the adverse physiologic response to stimulation based on a physiologic parameter indicative of muscle fatigue and the processor adjusts operation of the stimulation circuit responsive to the output indication of muscle fatigue.

6. The system of claim 1, wherein the physiologic sensor device provides the output indication to the processor and the processor is configured to automatically determine from the output indication the adverse physiologic response to stimulation and to control application of electrical stimulation by the stimulation circuit responsive to the output indication of the adverse physiologic response to stimulation.

7. The system of claim 1, wherein the physiologic sensor device comprises a vital signs monitor, providing the output indication, wherein the processor is configured to automatically determine from the output indication the adverse physiologic response to stimulation and to control application of electrical stimulation by the stimulation circuit responsive to the output indication of the adverse physiologic response to stimulation.

8. The system of claim 1, wherein the physiologic sensor device comprises a glucose sensor providing the output indication, and wherein the processor is configured to automatically determine from the output indication the adverse physiologic response to the stimulation based on a change in glucose.

9. The system of claim 1, wherein the multiplicity of electrodes, stimulation circuit and processor are mounted on a skin patch comprising a substrate having a skin contact surface.

10. The system of claim 9, wherein the substrate comprises a disposable portion comprising the multiplicity of electrodes and a reusable portion that supports the switching circuit, the stimulation circuit, and the processor, the disposable portion and the reusable portion configured to be removably coupled together.

11. The system of claim 10, further comprising an RFID component disposed on the disposable portion.

12. The system of claim 9, wherein the multiplicity of electrodes is arranged on the skin contact surface in two groups spaced apart from one another.

13. The system of claim 12, wherein the processor, during selection of a subset of the multiplicity of electrodes, varies a current path established between individual electrodes of a first group and of a second group during application of electrical stimulation.

14. The system of claim 9, wherein the skin patch further comprises a transceiver, the processor programmed to control operation of the transceiver to wirelessly communicate with the patient interface unit when the patient interface unit is running the patient interface unit programming.

15. The system of claim 9, wherein the skin patch further comprises an inductive circuit for wirelessly receiving energy from an external source.

16. The system of claim 9, wherein the multiplicity of electrodes are configured to penetrate a stratum corneum of the subject when the skin patch is applied to the skin of the subject.

17. The system of claim 9, further comprising a stand-alone sensor, configured to be positioned on the subject spaced apart from the skin patch, the stand alone sensor configured to communicate with the processor or the patient interface unit when the patient interface unit is running the patient interface unit programming.

18. The system of claim 9, wherein the system comprises two or more skin patches, the patient interface unit programming configured to coordinate the application of electrical stimulation by the two or more skin patches.

19. The system of claim 9, wherein the substrate is configured to flexibly conform to anatomy of the subject.

20. The system of claim 1, wherein the processor is programmed to automatically determine an adjusted set of stimulation values for use with the stimulation circuit responsive to the adverse physiologic response to the stimulation.

21. The system of claim 1, wherein the physiologic sensor device comprises an ischemia sensor providing the output indication, wherein the processor is configured to automatically determine from the output indication the adverse physiologic response to the stimulation based on an indication of muscle ischemia.

22. The system of claim 1, wherein the physiologic sensor device comprises an oxygen sensor providing the output indication, wherein the processor is configured to automatically determine from the output indication the adverse physiologic response to the stimulation based on an in vivo indication of oxygen.

23. The system of claim 1, wherein the physiologic sensor comprises a blood pressure sensor providing the output indication, wherein the processor is configured to automatically determine from the output indication the adverse physiologic response based on a change in blood pressure.

24. The system of claim 1, wherein the physiologic sensor comprises a body temperature sensor, providing the output indication, wherein the processor is configured to automatically determine from the output indication the adverse physiologic response based on a change in body temperature.

25. The system of claim 1, wherein the physiologic sensor is configured to generate the output indication of the physiological parameter of the subject based on monitoring of a physiological parameter of the subject corresponding to a stimulation treatment session, wherein the physiological parameter is correlative with insulin sensitivity and comprises an indication of at least one of: skin sympathetic nerve activity, motor nerve conduction speed, RR interval, homeostatic model assessment of insulin resistance, or muscle capture threshold.

26. The system of claim 1, further comprising the physiologic sensor device coupled to the processor to monitor or detect the adverse physiologic response to stimulation comprising hypoglycemia.

27. The system of claim 1, further comprising the physiologic sensor device coupled to the processor to monitor or detect the adverse physiologic response to stimulation comprising muscle dysfunction.

28. The system of claim 1, further comprising the physiologic sensor device coupled to the processor to monitor or detect the adverse physiologic response to stimulation comprising cardiovascular dysfunction.

29. The system of claim 1, further comprising the physiologic sensor device coupled to the processor to monitor or detect the adverse physiologic response to stimulation comprising tissue ischemia.

30. The system of claim 1, further comprising the physiologic sensor device coupled to the processor to monitor or detect the adverse physiologic response to stimulation comprising anaerobic muscle activity.

31. The system of claim 1, wherein the physiologic sensor device comprises an impedance device providing the output indication, wherein the processor is configured to automatically determine from the output indication the adverse physiologic response to stimulation and to control application of electrical stimulation by the stimulation circuit responsive to the output indication of the adverse physiologic response to stimulation.

32. The system of claim 1, wherein the physiologic sensor device comprises an MMG device providing the output indication, wherein the processor is configured to automatically determine from the output indication the adverse physiologic response to stimulation and to control application of electrical stimulation by the stimulation circuit responsive to the output indication of the adverse physiologic response to stimulation.

33. The system of claim 1, wherein the physiologic sensor device comprises an infrared sensor providing the output indication, wherein the processor is configured to automatically determine from the output indication the adverse physiologic response to stimulation and to control application of electrical stimulation by the stimulation circuit responsive to the output indication of the adverse physiologic response to stimulation.

34. The system of claim 1, wherein the physiologic sensor device comprises an EMG device providing the output indication, wherein the processor is configured to automatically determine from the output indication the adverse physiologic response to stimulation and to control application of electrical stimulation by the stimulation circuit responsive to the output indication of the adverse physiologic response to stimulation.

35. A system for stimulating nervous tissue associated with one or more skeletal muscles of a subject, the system comprising:
- a multiplicity of electrodes;
- a switching circuit coupled to the multiplicity of electrodes;
- a stimulation circuit operatively coupled to the switching circuit;
- a physiologic sensor device, configured to generate an output indication of an adverse physiologic response corresponding to a stimulation treatment session;
- a processor operatively communicatively coupled to the stimulation circuit and the switching circuit and the physiologic sensor device; the processor programmed to analyze the output indication and, when the output indication from the physiologic sensor device indicates the adverse physiologic response to the stimulation, to respond to the indication of the adverse physiologic response to the stimulation by terminating or otherwise adjusting the stimulation treatment session; and
- a non-transitory medium containing patient interface unit programming, the patient interface unit programming configured for use with a patient interface unit for controlling operation of the processor, switching circuit and stimulation circuit.

* * * * *